US011361853B2

(12) United States Patent
Stern

(10) Patent No.: US 11,361,853 B2
(45) Date of Patent: **\*Jun. 14, 2022**

(54) METHOD AND SYSTEM FOR AUTOMATED MEDICAL RECORDS PROCESSING WITH TELEMEDICINE

(71) Applicant: David E. Stern, Rockford, IL (US)

(72) Inventor: David E. Stern, Rockford, IL (US)

(73) Assignee: Practice Velocity, LLC, Machesney Park, IL (US)

( * ) Notice: Subject to any disclaimer, the term of this patent is extended or adjusted under 35 U.S.C. 154(b) by 192 days.

This patent is subject to a terminal disclaimer.

(21) Appl. No.: 16/926,898

(22) Filed: Jul. 13, 2020

(65) Prior Publication Data

US 2020/0342966 A1    Oct. 29, 2020

Related U.S. Application Data

(63) Continuation of application No. 15/837,799, filed on Dec. 11, 2017, now Pat. No. 10,714,213, which is a
(Continued)

(51) Int. Cl.
    *G16H 10/60*      (2018.01)
    *G16H 40/67*      (2018.01)
(Continued)

(52) U.S. Cl.
    CPC ......... *G16H 10/60* (2018.01); *G06F 16/9538* (2019.01); *G06Q 10/04* (2013.01);
(Continued)

(58) Field of Classification Search
    CPC ........ G16H 10/60; G16H 15/00; G16H 40/20; G16H 40/67; G16H 50/20; G16H 50/70;
(Continued)

(56) References Cited

U.S. PATENT DOCUMENTS

| | | |
|---|---|---|
| 3,714,486 A | 1/1973 | McCrary |
| 3,783,251 A | 1/1974 | Pavkovich |

(Continued)

OTHER PUBLICATIONS

Brown et al. "VistaA—U.S. Dept. of Veterans Affairs national-scale HIS"; International Journal of Medical Informatics; 2003; pp. 135-156. (Year: 2003).*

(Continued)

*Primary Examiner* — Jason S Tiedeman
(74) *Attorney, Agent, or Firm* — Lesavich High-Tech Law Group, S.C.; Stephen Lesavich

(57) ABSTRACT

A method and system for automated medical records processing with telemedicine is presented. The method and system includes plural electronic medical templates specifically designed such that they reduce the complexity and risk associated with collecting virtual patient encounter information, creating a medical diagnosis, tracking the patient through the medical processes during a telemedicine session and generate the appropriate number and type medical codes for a specific type of medical practice when processed. The medical codes and other types of processed virtual patient encounter information are displayed in real-time on electronic medical records and invoices immediately after a virtual patient encounter from a telemedicine visit.

20 Claims, 48 Drawing Sheets

Related U.S. Application Data continuation-in-part of application No. 14/098,761, filed on Dec. 6, 2013, now Pat. No. 9,842,188, which is a continuation-in-part of application No. 12/622,497, filed on Nov. 20, 2009, now Pat. No. 8,606,594, which is a continuation-in-part of application No. 10/692,976, filed on Oct. 24, 2003, now Pat. No. 7,624,027.

(60) Provisional application No. 60/422,083, filed on Oct. 29, 2002.

(51) Int. Cl.

| | | |
|---|---|---|
| *G06Q 10/06* | (2012.01) | |
| *G16H 40/20* | (2018.01) | |
| *G16H 80/00* | (2018.01) | |
| *G16H 50/20* | (2018.01) | |
| *G16H 50/70* | (2018.01) | |
| *G16H 70/20* | (2018.01) | |
| *G06Q 30/04* | (2012.01) | |
| *G06Q 40/08* | (2012.01) | |
| *G16H 15/00* | (2018.01) | |
| *G06Q 10/04* | (2012.01) | |
| *G16H 70/60* | (2018.01) | |
| *G06Q 10/10* | (2012.01) | |
| *H04L 67/12* | (2022.01) | |
| *G06F 16/9538* | (2019.01) | |
| *A61B 5/00* | (2006.01) | |
| *G06Q 30/00* | (2012.01) | |

(52) U.S. Cl.
CPC ... *G06Q 10/0635* (2013.01); *G06Q 10/06315* (2013.01); *G06Q 10/10* (2013.01); *G06Q 30/04* (2013.01); *G06Q 40/08* (2013.01); *G16H 15/00* (2018.01); *G16H 40/20* (2018.01); *G16H 40/67* (2018.01); *G16H 50/20* (2018.01); *G16H 50/70* (2018.01); *G16H 70/20* (2018.01); *G16H 70/60* (2018.01); *G16H 80/00* (2018.01); *H04L 67/12* (2013.01); *A61B 5/002* (2013.01); *G06Q 30/0185* (2013.01)

(58) Field of Classification Search
CPC ........ G16H 70/20; G16H 70/60; G16H 80/00; G06F 16/9538; G06Q 10/04; G06Q 10/06315; G06Q 10/0635; G06Q 10/10; G06Q 30/04; G06Q 40/08; G06Q 30/0185; H04L 67/12; A61B 5/002
USPC .......................................................... 705/2, 3
See application file for complete search history.

(56) References Cited

U.S. PATENT DOCUMENTS

| | | |
|---|---|---|
| 3,783,288 A | 1/1974 | Barbour |
| 3,839,708 A | 10/1974 | Bredesen |
| 3,946,236 A | 3/1976 | Roberts |
| 4,051,522 A | 9/1977 | Healy et al. |
| 4,290,114 A | 9/1981 | Sinay |
| 4,315,309 A | 2/1982 | Coli |
| 4,408,181 A | 10/1983 | Nakayama |
| 4,489,387 A | 12/1984 | Lamb |
| 4,491,725 A | 1/1985 | Pritchard |
| 4,553,206 A | 11/1985 | Smutek |
| 4,630,274 A | 12/1986 | Schafer |
| 4,658,370 A | 4/1987 | Erman |
| 4,667,292 A | 5/1987 | Mohlenbrock |
| 4,711,996 A | 12/1987 | Drexler |
| 4,745,268 A | 5/1988 | Drexler |
| 4,803,641 A | 2/1989 | Hardy |
| 4,835,372 A | 5/1989 | Gombrich |
| 4,857,713 A | 8/1989 | Brown |
| 4,857,716 A | 8/1989 | Gombrich |
| 4,858,121 A | 8/1989 | Barber |
| 4,878,175 A | 10/1989 | Norden-Paul |
| 4,937,743 A | 6/1990 | Rassman |
| 4,987,538 A | 1/1991 | Johnson |
| 5,001,630 A | 3/1991 | Wiltfong |
| 5,002,630 A | 3/1991 | Kermani |
| 5,018,067 A | 5/1991 | Mohlenbrock |
| 5,065,315 A | 11/1991 | Garcia |
| 5,070,452 A | 12/1991 | Doyle |
| 5,072,383 A | 12/1991 | Brimm |
| 5,077,666 A | 12/1991 | Brimm |
| 5,099,424 A | 3/1992 | Schneiderman |
| 5,148,366 A | 9/1992 | Buchanan |
| 5,225,976 A | 7/1993 | Tawil |
| 5,235,507 A | 8/1993 | Sackler |
| 5,235,702 A | 8/1993 | Miller |
| 5,253,164 A | 10/1993 | Holloway |
| 5,301,105 A | 4/1994 | Cummings |
| 5,307,262 A | 4/1994 | Ertel |
| 5,319,543 A | 6/1994 | Wilhelm |
| 5,324,077 A | 6/1994 | Kessler |
| 5,325,293 A | 6/1994 | Dorne |
| 5,359,509 A | 10/1994 | Little |
| 5,365,425 A | 11/1994 | Torma |
| 5,392,209 A | 2/1995 | Eason |
| 5,404,292 A | 4/1995 | Hendrickson |
| 5,420,409 A | 5/1995 | Longacre |
| 5,465,082 A | 11/1995 | Chaco |
| 5,467,268 A | 11/1995 | Sisley |
| 5,471,382 A | 11/1995 | Tallman |
| 5,482,008 A | 1/1996 | Stafford |
| 5,483,443 A | 1/1996 | Milstein |
| 5,486,999 A | 1/1996 | Mebane |
| 5,490,196 A | 2/1996 | Rudich |
| 5,504,796 A | 4/1996 | Da Silveria |
| 5,510,606 A | 4/1996 | Worthington |
| 5,519,607 A | 5/1996 | Tawil |
| 5,557,514 A | 9/1996 | Seare |
| 5,583,758 A | 12/1996 | McIlroy |
| 5,583,759 A | 12/1996 | Rensimer et al. |
| 5,583,760 A | 12/1996 | Klesse |
| 5,621,779 A | 4/1997 | Hughes |
| 5,644,778 A | 7/1997 | Burks |
| 5,661,291 A | 8/1997 | Ahearn |
| 5,663,999 A | 9/1997 | Siochi |
| 5,664,109 A | 9/1997 | Johnson |
| 5,664,207 A | 9/1997 | Crumpler |
| 5,671,282 A | 9/1997 | Wolff |
| 5,672,154 A | 9/1997 | Sillen |
| 5,700,998 A | 12/1997 | Palti |
| 5,724,379 A | 3/1998 | Perkins |
| 5,754,622 A | 5/1998 | Hughes |
| 5,772,585 A | 6/1998 | Lavin |
| 5,819,228 A | 10/1998 | Spiro |
| 5,832,447 A | 11/1998 | Rieker |
| 5,835,897 A | 11/1998 | Dang |
| 5,842,976 A | 12/1998 | Williamson |
| 5,845,253 A | 12/1998 | McIlroy et al. |
| 5,845,254 A | 12/1998 | Lockwood |
| 5,845,269 A | 12/1998 | Kortge |
| 5,848,426 A | 12/1998 | Wang |
| 5,867,553 A | 2/1999 | Gordon |
| 5,915,241 A | 6/1999 | Giannini |
| 5,923,014 A | 7/1999 | Szymusiak |
| 5,924,074 A | 7/1999 | Evans |
| 5,930,759 A | 7/1999 | Moore |
| 5,953,704 A | 9/1999 | McIlroy |
| 5,970,463 A | 10/1999 | Cave |
| 5,971,279 A | 10/1999 | Raistrick |
| 5,979,757 A | 11/1999 | Tracy |
| 6,159,013 A | 12/2000 | Parienti |
| 6,192,400 B1 | 2/2001 | Hanson |
| 6,208,973 B1 | 3/2001 | Boyer |
| 6,222,452 B1 | 4/2001 | Ahlstrom |
| 6,342,839 B1 | 1/2002 | Curkendall |

(56) References Cited

U.S. PATENT DOCUMENTS

| | | |
|---|---|---|
| 6,347,329 B1 | 2/2002 | Evans |
| 6,366,651 B1 | 4/2002 | Griffith |
| 6,370,511 B1 | 4/2002 | Dang |
| 6,393,404 B2 | 5/2002 | Waters |
| 6,464,136 B2 | 10/2002 | Walsh |
| 6,497,358 B1 | 12/2002 | Walsh |
| 6,529,876 B1 | 3/2003 | Dart |
| 6,629,876 B1 | 3/2003 | Dart |
| 6,592,517 B2 | 7/2003 | Pratt |
| 6,597,948 B1 | 7/2003 | Rockwell |
| 6,603,464 B1 | 8/2003 | Rabin |
| 6,637,649 B2 | 10/2003 | Walsh |
| 6,655,583 B2 | 12/2003 | Walsh |
| 6,824,052 B2 | 11/2004 | Walsh |
| 6,830,180 B2 | 12/2004 | Walsh |
| 7,624,027 B1 | 11/2009 | Stern et al. |
| 8,341,141 B2 | 12/2012 | Krislov |
| 8,412,147 B2 | 4/2013 | Hunter |
| 8,463,765 B2 | 6/2013 | Lesavich |
| 8,533,015 B2 | 9/2013 | Meegan |
| 8,542,809 B2 | 9/2013 | Bookstaff |
| 8,589,372 B2 | 11/2013 | Krislov |
| 8,606,594 B2 | 12/2013 | Stern |
| 8,738,396 B2 | 5/2014 | Green |
| 9,137,250 B2 | 9/2015 | Lesavich et al. |
| 9,361,479 B2 | 6/2016 | Lesavich et al. |
| 9,569,771 B2 | 2/2017 | Lesavich et al. |
| 9,842,188 B2 | 12/2017 | Stern |
| 10,249,388 B2 | 4/2019 | Zabetian et al. |
| 10,595,887 B2* | 3/2020 | Shelton, IV ............ A61B 90/37 |
| 10,713,243 B2 | 7/2020 | Stern |
| 2002/0145634 A1 | 10/2002 | Gueramy et al. |
| 2007/0214002 A1 | 9/2007 | Smith et al. |
| 2010/0094657 A1 | 4/2010 | Stern et al. |
| 2011/0078303 A1* | 3/2011 | Li ........................ G06F 9/5072 |
| | | 718/1 |
| 2011/0020871 A1 | 8/2011 | Lesavich |
| 2012/0166221 A1* | 6/2012 | Phillips ................. G16H 40/67 |
| | | 705/2 |
| 2012/0278622 A1 | 11/2012 | Lesavich et al. |
| 2013/0231947 A1 | 9/2013 | Shusterman |
| 2014/0189792 A1 | 7/2014 | Lesavich et al. |
| 2015/0379209 A1* | 12/2015 | Kusuma ................ G16H 30/40 |
| | | 705/3 |
| 2015/0379301 A1 | 12/2015 | Lesavich et al. |
| 2016/0321654 A1 | 11/2016 | Lesavich et al. |
| 2017/0193182 A1* | 7/2017 | Mihai .................... G16H 80/00 |
| 2018/0114595 A1 | 4/2018 | Stern |
| 2019/0216312 A1* | 7/2019 | Brocwell ............. A61B 3/0033 |
| 2020/0244605 A1* | 7/2020 | Nagaraja ............... G16H 50/20 |
| 2020/0398062 A1* | 12/2020 | Ibarrola ............. A61N 1/36139 |
| 2020/0402674 A1* | 12/2020 | DeBates ................ G16H 40/67 |

OTHER PUBLICATIONS

Bellazzi, Web-based telemedicine systems for home-care; technical issues and experiences, Computer Methods and Programs in Biomedicine, vol. 64, Issue 3, Mar. 1, 2001, pp. 175-187. (Year: 2001).*

Abo-Zahhad et al., "A Wireless Emergency Telemedicine System for Patients Monitoring and Diagnosis," International Journal of Telemedicine and Applications, vol. 2014 (2014), Article ID 380787, 9 pages. (Year: 2014).*

Newman, William, "A desk supporting computer-based interaction with paper documents," Conference on Human Factors in Computing Systems, Proceedings of the SIGCHI conference on Human factors in computing systems, Monterey, California, United States, pp. 587-592, May 3, 1992, ISBN: 0-89791-513-5.

Mathijs, Vogelzang, Felix Zijlstra and Maarten WM Nijsten, "Design and implementation of GRIP: a computerized glucose control system at a surgical care unit," BioMed Central (BMC) Medical Informatics and Decision Making vol. 5, No. 38, Dec. 19, 2005.

* cited by examiner

Copyright © 2002, 2003 by Practice Velocity, LLC

FIG. 3

```
                                    NECK  — 40                    — 48
   — 44  — 46
  ● ☐  ☐ EXAM (MASS, APPEARANCE, SYMMERTY, TRACHEA, CREPITUS)
  ● ☐  ☐ THYROID (ENGLARGEMENT, TENDERNESS, MASS) — 50
    GREEN RED
```

42

DIAGNOSES — 41

☐ NEW (W/U PENDING)

☐ NEW (W/U COMPLETE)

EST ☐ RECUR   ☐ EXAC

EST ☐ RECUR   ☐ EXAC

☐ EST (STABLE)

☐ EST (STABLE)

☐ EST (STABLE)

☐ MINOR   ☐ NEW/RECUR

☐ MINOR
(e.g, cold, tinea, or insect bite)

FIG. 8

HX _____ (pick lowest)    124

|      | CC | HPI | PFMSH | ROS |
|------|----|-----|-------|-----|
| PF   |    | 0   | 0     | 0   |
| EXPF |    | 1   | 1     | 1   |
| DET  |    |     |       | 2   |
| COMP | 1  | 4   | 2,3   | 10  |

| PF   | 1 bullet |
|------|----------|
| EXPF | 6 bullets |
| DET  | 12 bullets (2 systems) |
| COMP | ≥2 bullets each in ≥9 systems |

FIG. 10

CX _____ (pick lowest)    128

|      | DX | RISK |
|------|----|----|
| HIGH | 4  | 4  |
| MOD  | 3  | 3  |
| LOW  | 2  | 2  |
| SF   | 1  | 1  |

FIGS. 8-10 Copyright © 2002, 2003 by Practice Velocity, LLC

Final E/M NEW OUTPATIENT

|    | 99201 | 99202 | 99203 | 99204 | 99205 |
|----|-------|-------|-------|-------|-------|
| HX | PF    | EXPF  | DET   | COMP  | COMP  |
| PX | PF    | EXPF  | DET   | COMP  | COMP  |
| CX | SF    | SF    | LOW   | MOD   | HIGH  |

Final E/M ESTABLISHED OUTPATIENT

|    | 99212 | 99213 | 99214 | 99215 |
|----|-------|-------|-------|-------|
| HX | PF    | EXPF  | DET   | COMP  |
| PX | PF    | EXPF  | DET   | COMP  |
| CX | SF    | LOW   | MOD   | HIGH  |

FIGS. 11-12 Copyright © 2002, 2003 by Practice Velocity, LLC

FIG. 18

Copyright © by Practice Velocity, LLC

Image on smartphone Copyright © by Practice Velocity, LLC

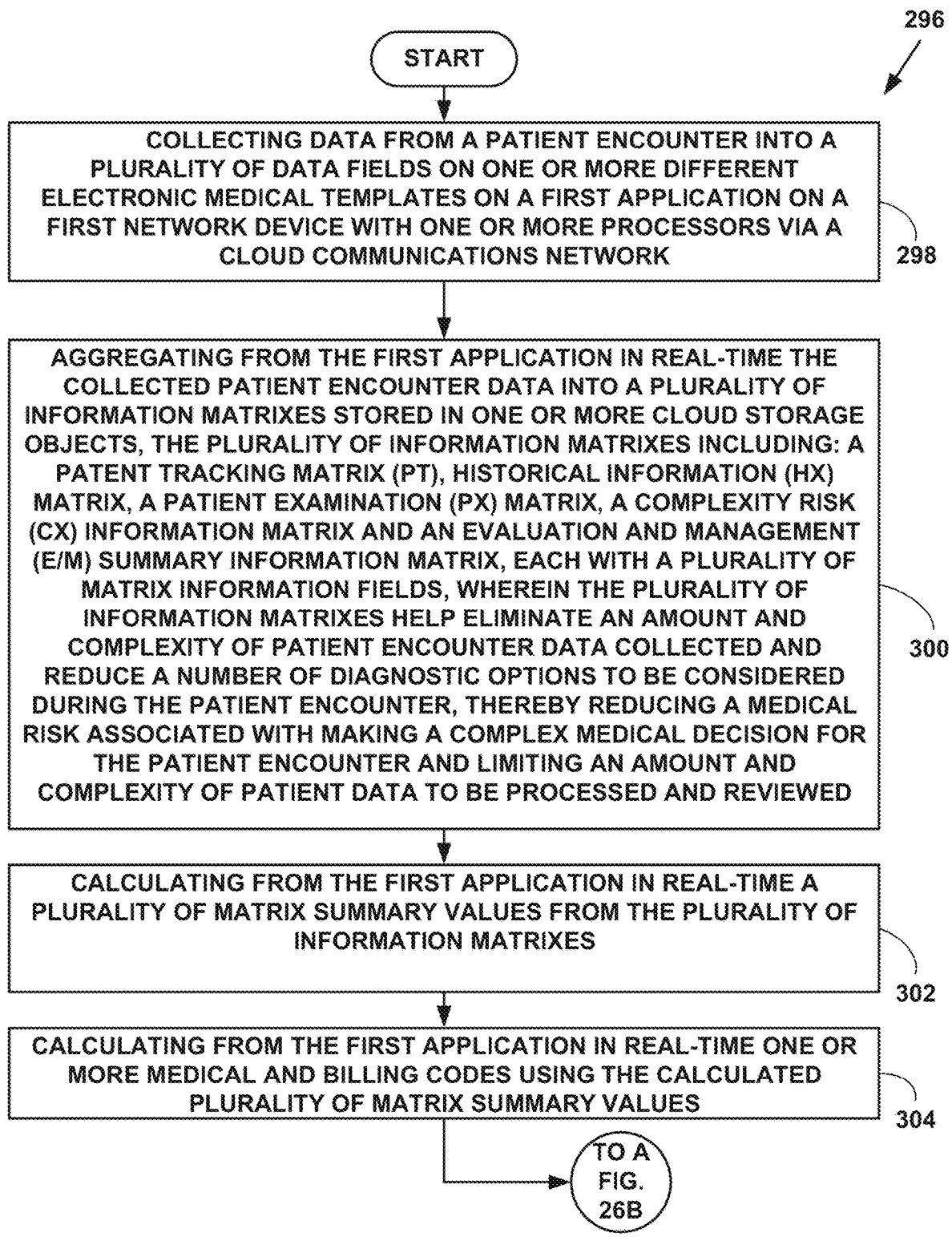

Copyright © by Practice Velocity, LLC

Copyright © by Practice Velocity, LLC

```
START
```

480 — PLURAL CLOUD SERVER NETWORK DEVICES EACH WITH A TELEMEDICINE APPLICATION AND ONE OR MORE PROCESSORS ON A CLOUD COMMUNICATIONS NETWORK, CREATE PLURAL POOLED CLOUD HARDWARE RESOURCES COMPRISING: (1) AUTOMATIC PROVISIONING OF PLURAL POOLED CLOUD HARDWARE RESOURCES USABLE IN ANY AMOUNT AT ANY TIME AS NEEDED AND AVAILABLE VIA PLURAL CLOUD BROADBAND NETWORK ACCESS COMPONENTS ON THE PLURAL CLOUD SERVER NETWORK DEVICES; (2) AUTOMATIC SCALING OF THE PLURAL POOLED CLOUD HARDWARE RESOURCES TO OBTAIN AND RELEASE ONE OR MORE OF THE PLURAL POOLED CLOUD HARDWARE RESOURCES AS REQUIRED; (3) AUTOMATIC CONTROLLING AND OPTIMIZING THE PLURAL POOLED CLOUD HARDWARE RESOURCES WITH A METERING METHOD; (4) PLURAL CLOUD SOFTWARE SERVICES FOR AUTOMATED PROCESSING OF MEDICAL INFORMATION INCLUDING A CLOUD PLATFORM AS A SERVICE (PAAS), A CLOUD COMPUTING INFRASTRUCTURE AS A SERVICE (IAAS), AND PLURAL AVAILABLE CLOUD SOFTWARE SERVICES AS A SERVICE (SAAS) INCLUDING A PLURAL DIFFERENT SOFTWARE SERVICES FOR AUTOMATED RISK REDUCTION IN PROCESSING OF MEDICAL RECORDS INFORMATION AFTER VIRTUAL PATIENT ENCOUNTERS VIA TELEMEDICINE VISITS, THE PLURAL CLOUD SOFTWARE SERVICES FOR AUTOMATED PROCESSING OF MEDICAL INFORMATION COMPRISING: CLOUD NETWORKING SERVICES, STORAGE SERVICES, VIRTUALIZATION SERVICES, OPERATING SYSTEM SERVICES, RUN-TIME SERVICES, DATA SERVICES AND APPLICATION SERVICES EXECUTED WITH THE PLURAL POOLED CLOUD HARDWARE RESOURCES

482 — A FIRST TELEMEDICINE APPLICATION ON A FIRST CLOUD NETWORK DEVICE WITH ONE OR MORE PROCESSOR RECEIVES A REQUEST FOR A TELEMEDICINE VISIT AND VIRTUAL PATIENT ENCOUNTER FROM A CLIENT TELEMEDICINE APPLICATION ON A CLIENT NETWORK DEVICE WITH ONE OR MORE CLIENT NETWORK DEVICE PROCESSORS

THE FIRST TELEMEDICINE APPLICATION ON THE FIRST CLOUD SERVER NETWORK DEVICE APPLIES ONE OR MORE BALANCING METHODS CREATING A BALANCING SELECTION INCLUDING: (1) BALANCING TELEMEDICINE VISIT WORKFLOW ACROSS THE PLURAL OTHER TELEMEDICINE APPLICATIONS ON THE PLURAL CLOUD SERVER NETWORK DEVICES AND ACROSS THE PLURAL POOLED CLOUD HARDWARE RESOURCES AND THE PLURAL CLOUD SOFTWARE SERVICES, AND (2) BALANCING TELEMEDICINE PATIENT LOAD ACROSS A PLURAL MEDICAL FACILITIES INCLUDING AN AVAILABILITY OF PLURAL MEDICAL PERSONNEL AT THE PLURAL MEDICAL FACILITIES AND A CURRENT ACTUAL PATIENT LOAD AND CURRENT TELEMEDICINE PATIENT LOAD AT THE PLURAL MEDICAL FACILITIES — 484

THE FIRST TELEMEDICINE APPLICATION ON THE FIRST CLOUD SERVER NETWORK DEVICE SELECTS WITH THE BALANCING SELECTION FROM THE ONE OR MORE BALANCING METHODS A SELECTED TELEMEDICINE APPLICATION ON A SELECTED CLOUD SERVER NETWORK DEVICE TO ACCEPT THE REQUEST FOR THE TELEMEDICINE VISIT AND THE VIRTUAL PATIENT ENCOUNTER — 486

A SELECTION MESSAGE IS SENT FROM THE FIRST TELEMEDICINE APPLICATION ON THE FIRST CLOUD SERVER NETWORK DEVICE VIA THE CLOUD COMMUNICATIONS NETWORK TO THE SELECTED TELEMEDICINE APPLICATION ON THE SELECTED CLOUD SERVER NETWORK DEVICE INDICATING THE SELECTED TELEMEDICINE APPLICATION ON THE SELECTED CLOUD SERVER NETWORK DEVICE HAS BEEN SELECTED TO ACCEPT THE TELEMEDICINE VISIT AND THE VIRTUAL PATIENT ENCOUNTER — 488

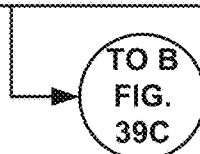

THE SELECTED TELEMEDICINE APPLICATION ON THE SELECTED CLOUD SERVER NETWORK DEVICE SELECTS A PAAS AND AN IAAS PROVIDED BY THE PLURAL POOLED CLOUD HARDWARE RESOURCES ON THE CLOUD COMMUNICATIONS NETWORK — 490

↓

THE SELECTED TELEMEDICINE APPLICATION ON THE SELECTED CLOUD SERVER NETWORK DEVICE SELECTS VIA THE CLOUD COMMUNICATIONS NETWORK A FIRST SET OF SAAS CLOUD SERVICES FROM THE PLURAL AVAILABLE CLOUD SAAS SERVICES FOR AUTOMATED ELECTRONIC MEDICAL RECORDS PROCESSING INCLUDING REDUCING RISK AND REDUCING A NUMBER OF POSSIBLE DIAGNOSTIC DECISIONS WHEN PROCESSING MEDICAL RECORDS FROM THE VIRTUAL PATIENT ENCOUNTER VIA THE TELEMEDICINE VISIT — 492

↓

THE SELECTED TELEMEDICINE APPLICATION ON THE SELECTED CLOUD SERVER NETWORK DEVICE SELECTS VIA THE CLOUD COMMUNICATIONS NETWORK, ONE OR MORE SAAS SERVICES FROM THE SELECTED FIRST SET OF SAAS CLOUD SERVICES, PLURAL INDIVIDUAL DATA STRUCTURES COMPRISING A PLURAL MEDICAL INFORMATION MATRIXES INCLUDING A PATIENT TRACKING (PT) MATRIX, HISTORICAL INFORMATION (HX) MATRIX, PATIENT EXAMINATION (PX) MATRIX, COMPLEXITY RISK (CX) INFORMATION MATRIX AND AN EVALUATION AND MANAGEMENT (E/M) SUMMARY INFORMATION MATRIX, EACH WITH PLURAL UNIQUE MATRIX INFORMATION FIELDS, THE PLURAL INDIVIDUAL DATA STRUCTURES STORED IN ONE OR MORE CLOUD STORAGE OBJECTS ON THE CLOUD COMMUNICATIONS NETWORK AND AVAILABLE TO FIRST SET OF SAAS CLOUD SERVICES SELECTED BY THE SELECTED TELEMEDICINE APPLICATION ON THE SELECTED CLOUD SERVER NETWORK DEVICE — 494

```
THE SELECTED TELEMEDICINE APPLICATION ON THE SELECTED
CLOUD SERVER NETWORK DEVICE VIA THE CLOUD COMMUNICATIONS
NETWORK SECURELY COLLECTS DATA FROM THE CLIENT
TELEMEDICINE APPLICATION ON THE CLIENT NETWORK DEVICE FOR       496
THE VIRTUAL PATIENT ENCOUNTER DURING THE TELEMEDICINE VISIT
INTO PLURAL OF DATA FIELDS ON ONE OR MORE DIFFERENT
ELECTRONIC MEDICAL TEMPLATES WITH ONE OR MORE SAAS
SERVICES FROM THE SELECTED FIRST SET OF SAAS CLOUD SERVICES
```

```
THE SELECTED TELEMEDICINE APPLICATION ON THE SELECTED CLOUD
SERVER NETWORK DEVICE AGGREGATES WITH ONE OR MORE SAAS
SERVICES FROM THE SELECTED FIRST SET OF SAAS CLOUD SERVICES
IN REAL-TIME ONLY SELECTED ONES OF DATA ITEMS FROM THE
PLURAL DATA FIELDS FROM THE ONE OR MORE DIFFERENT
ELECTRONIC MEDICAL TEMPLATES STORING THE COLLECTED
VIRTUAL PATIENT ENCOUNTER DATA FROM THE TELEMEDICINE VISIT
INTO THE PLURAL INFORMATION MATRIXES STORED IN THE ONE OR     498
MORE CLOUD STORAGE OBJECTS, THE PLURAL INFORMATION
MATRIXES INCLUDING: THE PATIENT TRACKING (PT) MATRIX,
HISTORICAL INFORMATION (HX) MATRIX, PATIENT EXAMINATION (PX)
MATRIX, COMPLEXITY RISK (CX) INFORMATION MATRIX AND THE
EVALUATION AND MANAGEMENT (E/M) SUMMARY INFORMATION
MATRIX, EACH WITH THE PLURAL UNIQUE MATRIX INFORMATION DATA
FIELDS
```

```
THE SELECTED TELEMEDICINE APPLICATION ON THE SELECTED CLOUD
SERVER NETWORK DEVICE VIA THE CLOUD COMMUNICATIONS
NETWORK ELIMINATES WITH ONE OR MORE SAAS SERVICES FROM
THE SELECTED FIRST SET OF SAAS CLOUD SERVICES WITH THE ONLY
SELECTED ONES OF DATA ITEMS AGGREGATED INTO THE PLURAL
INFORMATION MATRIXES AN AMOUNT AND COMPLEXITY OF THE          500
VIRTUAL PATIENT ENCOUNTER DATA FROM THE TELEMEDICINE VISIT
COLLECTED TO BE REVIEWED DURING THE VIRTUAL PATIENT
ENCOUNTER FROM THE TELEMEDICINE VISIT
```

502 — THE SELECTED TELEMEDICINE APPLICATION ON THE SELECTED CLOUD SERVER NETWORK DEVICE VIA THE CLOUD COMMUNICATIONS NETWORK WITH ONE OR MORE SAAS SERVICES FROM THE SELECTED FIRST SET OF SAAS CLOUD SERVICES WITH THE SELECTED DATA ITEMS AGGREGATED INTO THE PLURAL INFORMATION MATRIXES REDUCES A NUMBER OF DIAGNOSTIC OPTIONS TO BE CONSIDERED DURING THE VIRTUAL PATIENT ENCOUNTER VIA THE TELEMEDICINE VISIT, THEREBY REDUCING A MEDICAL RISK ASSOCIATED WITH MAKING A COMPLEX MEDICAL DECISION FOR THE VIRTUAL PATIENT ENCOUNTER VIA THE TELEMEDICINE VISIT AND LIMITING AN AMOUNT AND COMPLEXITY OF PATIENT DATA TO BE PROCESSED AND REVIEWED AFTER THE VIRTUAL PATIENT ENCOUNTER VIA THE TELEMEDICINE VISIT

504 — THE SELECTED TELEMEDICINE APPLICATION ON THE SELECTED CLOUD SERVER NETWORK DEVICE VIA THE CLOUD COMMUNICATIONS NETWORK WITH ONE OR MORE SAAS SERVICES FROM THE SELECTED FIRST SET OF SAAS CLOUD SERVICES CALCULATES IN REAL-TIME PLURAL MATRIX SUMMARY VALUES FROM THE PLURAL INFORMATION MATRIXES

506 — THE SELECTED TELEMEDICINE APPLICATION ON THE SELECTED CLOUD SERVER NETWORK DEVICE VIA THE CLOUD COMMUNICATIONS NETWORK WITH ONE OR MORE SAAS SERVICES FROM THE SELECTED FIRST SET OF SAAS CLOUD SERVICES CALCULATES IN REAL-TIME ONE OR MORE MEDICAL AND BILLING CODES USING THE CALCULATED PLURAL MATRIX SUMMARY VALUES

THE SELECTED TELEMEDICINE APPLICATION ON THE SELECTED CLOUD SERVER NETWORK DEVICE VIA THE CLOUD COMMUNICATIONS NETWORK WITH ONE OR MORE SAAS SERVICES FROM THE SELECTED FIRST SET OF SAAS CLOUD SERVICES GENERATES AUTOMATICALLY IN REAL-TIME AN ELECTRONIC PATIENT MEDICAL RECORD WITH A PLURAL DATA FIELDS FROM THE CALCULATED PLURAL MATRIX SUMMARY VALUES AND THE ONE OR MORE CALCULATED MEDICAL AND BILLING CODES — 508

↓

THE SELECTED TELEMEDICINE APPLICATION ON THE SELECTED CLOUD SERVER NETWORK DEVICE VIA THE CLOUD COMMUNICATIONS NETWORK WITH ONE OR MORE SAAS SERVICES FROM THE SELECTED FIRST SET OF SAAS CLOUD SERVICES GENERATES AUTOMATICALLY IN REAL-TIME A PATIENT INVOICE FOR THE VIRTUAL PATIENT ENCOUNTER VIA THE TELEMEDICINE VISIT FROM THE GENERATED ELECTRONIC MEDICAL RECORD — 510

↓

THE SELECTED TELEMEDICINE APPLICATION ON THE SELECTED CLOUD SERVER NETWORK DEVICEDEVICE VIA THE CLOUD COMMUNICATIONS NETWORK WITH ONE OR MORE SAAS SERVICES FROM THE SELECTED FIRST SET OF SAAS CLOUD SERVICES DISPLAYS SECURELY IN REAL-TIME ON THE SELECTED CLOUD SERVER NETWORK DEVICE ON A DISPLAY COMPONENT VIA A GRAPHICAL USER INTERFACE (GUI) SELECTED ONES OF THE PLURAL DATA FIELDS FROM THE GENERATED ELECTRONIC PATIENT MEDICAL RECORD, INCLUDING COMPLEXITY RISK INFORMATION FOR THE VIRTUAL PATIENT ENCOUNTER VIA THE TELEMEDICINE VISIT AND THE GENERATED PATIENT INVOICE. THE GENERATED ELECTRONIC MEDICAL RECORD PROVIDES A THREE HUNDRED-SIXTY DEGREE VIEW OF MEDICAL, BILLING, INSURANCE AND OTHER INFORMATION COLLECTED AND GENERATED FROM THE VIRTUAL PATIENT ENCOUNTER VIA THE TELEMEDICINE VISIT. DISPLAYING THE THREE HUNDRED SIXTY DEGREE VIEW COMPRISES DISPLAYING MEDICAL, BILLING, INSURANCE AND OTHER INFORMATION ON THE GUI SURROUNDING A PATIENT AVATAR FOR THE VIRTUAL PATIENT ENCOUNTER VIA THE TELEMEDICINE VISIT — 512

↓

( END )

Copyright © by Practice Velocity, LLC

METHOD AND SYSTEM FOR AUTOMATED MEDICAL RECORDS PROCESSING WITH TELEMEDICINE

CROSS REFERENCES TO RELATED APPLICATIONS

This U.S. Utility patent application is a Continuation-In-Part (CIP) of U.S. Utility patent application Ser. No. 15/837,799, filed on Dec. 11, 2017, which issued as U.S. Pat. No. 10,714,213, on Jul. 14, 2020, which is a CIP of Ser. No. 14/098,761, filed Dec. 6, 2013, which issued as U.S. Pat. No. 9,842,188, on Dec. 12, 2017, which is a CIP of U.S. Utility patent application Ser. No. 12/622,497, filed Nov. 20, 2009, which issued as U.S. Pat. No. 8,606,594, on Dec. 10, 2013, which is a CIP of U.S. Utility patent application Ser. No. 10/692,976, filed on Oct. 24, 2003, which issued as U.S. Pat. No. 7,624,027, on Nov. 24, 2009, that claims priority from U.S. Provisional patent application No. 60/422,083, filed on Oct. 29, 2002, the contents of all of which are incorporated herein by reference.

COPYRIGHT NOTICE

Pursuant to 37 C.F.R. 1.71(e), applicants note that a portion of this disclosure contains material that is subject to, for which is claimed copyright protection, such as, but not limited to, copies of paper forms, screen shots, user interfaces, electronic medical record formats, or any other aspects of this submission for which copyright protection is or may be available in any jurisdiction. The copyright owner has no objection to the facsimile reproduction by anyone of the patent document or patent disclosure, as it appears in the Patent Office patent file or records. All other rights are reserved, and all other reproduction, distribution, creation of derivative works based on the contents, public display, and public performance of the application or any part thereof are prohibited by applicable copyright law.

FIELD OF THE INVENTION

This invention relates to medical records and information. More specifically, it relates to a method and system for automated medical records processing with cloud computing including telemedicine.

BACKGROUND OF THE INVENTION

There are many different types of medical information that are routinely collected when a patient has an emergency or non-emergency medical problem, or visit a provider for a routine visit or annual physical. The medical information includes such information as current symptoms the patient is feeling, any medication the patient is currently taking, any past medical problems or surgeries the patient has, known allergies, family history, prescribed medications, etc.

Such medical information is typically recorded manually on paper forms by medical staff, nurses and/or providers. The medical information may also be dictated by a provider and later transcribed to another form by a medical transcriptionist.

The American Medical Association ("AMA") has developed a system of codes for medical and surgical procedures, diagnostic tests, laboratory studies, and other provider medical services rendered to patients. This system of codes is referred to as Current Procedural Terminology, ("CPT") codes. CPT codes provide a uniform language that details medical, surgical, and diagnostic services utilized by providers to communicate to third-party payors for the services that are rendered.

The CPT codes were first developed by the AMA in 1966. Each year, an annual publication is prepared by the AMA that includes CPT code changes corresponding with updates in medical technology and practice. The 2003 version of CPT codes, for example, CPT 2003, includes over 8,000 codes and descriptors. The CPT code set also include a set of modifiers that may be used to further define CPT codes.

Evaluation and Management (E/M) codes are a sub-set of the CPT codes that are used to describe a patient's encounter in a provider's office, hospital or other medical setting. E/M codes are used to describe the level of care a provider renders to a patient.

The CPT and E/M codes are assigned numeric codes that used to classify the information, categorize and organize the information and used to generate revenue for the organization that employs the medical personnel. The numeric codes may also include codes used by insurance companies or other types of organizations such as health organizations such as those responsible for communicable diseases.

SNOMED Clinical Terms or SNOMED CT is a systematically organized computer processed collection of medical terms providing codes, terms, synonyms and definitions used in clinical documentation and reporting. SNOMED CT is considered to be the most comprehensive, multilingual clinical healthcare terminology in the world.

The Health Care Finance Administration ("HCFA"), a U.S. government agency responsible for the operation of oversight of medical insurance programs such as Medicare and Medicaid, has also developed a set of medical codes and modifiers. The HCFA developed a set of medical codes called Health Care Procedural Coding System ("HCPCS") codes to help relate CPT codes to medical billing. The HCFA was renamed the Centers for Medicare & Medicaid Services (CMS) on Jun. 14, 2001.

In addition, the World Health Organization ("WHO") also developed a similar set of codes to identify medical diagnoses, conditions and injuries. These codes are called International Classification of Diseases 9th edition Clinical Modification ("ICD-9") codes and International Classifications 10th edition Clinical Modification ("ICD-10"). ICD-10 codes for both diagnoses and procedures have been developed, but are not yet used in the USA.

Accurate and proper coding of medical information is important because it helps determine financial reimbursement for physician services. It is also important to ensure compliance with state and federal regulations as well as help protect physicians from the financial and legal ramifications of government, insurance company and other types of audits.

"Cloud computing" is a term used to identify the delivery of computing requirements as a service to a heterogeneous community of end-recipients. The term cloud theoretically signifies abstraction of technology, resources and locations that are used in building an integrated computing infrastructure (including networks, systems, applications, etc.). All Cloud computing models rely heavily on sharing of resources to achieve coherence and economies of scale similar to a utility (like a grid for electricity) over a network.

Cloud computing provides services with a user's data, software and computation on over multiple networks. End users access cloud based applications through a web browser or a light weight desktop or mobile application while the rest of the application software and data are stored on servers at remote locations. Cloud computing provides a same or better service and performance with cloud software programs as if al the cloud software programs were actually installed locally on end-user devices.

At the foundation of cloud computing is the broader concept of infrastructure convergence and shared services. This type of cloud computing environment allows enterprises to get their applications up and running faster, with easier manageability and less maintenance, and enables the enterprise to more rapidly adjust resources (such as servers, storage, and networking) to meet fluctuating and unpredictable business demand.

With the recent events including a global pandemic caused by the Covid-19 virus, telemedicine is becoming increasingly important. Telemedicine includes remote clinical medical services, such as diagnosis and monitoring. When a global pandemic, rural and urban settings, lack of transport, lack of mobility, decreased funding, or a lack of staff restrict access to care, telemedicine bridges the patient care gap as well as providing distance-learning; meetings, supervision, online information and health data management and healthcare, system integration.

There are many problems associated with the collection and recording medical information when telemedicine is used. One problem is that incorrect medical coding creates both a revenue generation problem and a compliance problem for many physician practices.

For example, one study by Mitchell S. King, Lisa Sharp, and Martin S. Lipsky, entitled "Accuracy of CPT evaluation and management coding by family physicians," and published in the Journal of American Board of Family Practice 14(3):184-192, 2001, has shown that family physicians tend to generate lower-level E/M codes for established patients, thereby "undercoding" the established patient visit. The undercoding results in a loss of potential revenues. Investigative agencies may also classify this practice as fraudulent, in that it may be construed to indicate that the provider is reducing fees by undercoding, and thereby attempting to entice patients to visit more frequently.

These same family physicians also tend to generate higher-level E/M codes than necessary for new patients, thereby "overcoding" the new patient visit. This results in rejection of insurance payments and could result in loss of revenue, insurance audits and potential prosecution under the Federal False Claims Act ("FFCA"), 31 U.S.C. 3729 or other Federal and state laws used prevent fraudulent insurance claims.

Another problem is that incorrect or improper coding of medical information could result in non-compliance with the Health Insurance Portability and Accountability Act ("HIPAA") 42 U.S.C. 1320d, et. seq. and other Federal and state laws enacted to protect privacy.

Another problem is that medical organizations use many different types of medical codes from many different types of medical organizations on many different types of proprietary and public medical forms. The medical information is typically manually re-handled several times by several different types of people (e.g., providers, nurses, medical billing specialist, etc.) with different expertise levels with respect to coding of medical information. This handling may introduce errors for the coding of medical information at many different levels.

Another problem is that the medical information is often manually entered into a data processing system. A medical technician with knowledge of medical information and medical codes must process the information to assign the proper codes. As was described above, there are typically multiple sets of medical codes such as those used for diagnosis, billing, insurance, etc. that are routinely used and changed on a periodic basis. This may also introduce errors for the coding of medical information at many different levels.

Another problem is that it typically takes a significant amount of time to process medical information and create the proper medical codes from a patient encounter. This often leads to a very slow revenue stream for physicians and a large amount of frustration for patients.

Another problem is that when a patient enters a medical facility their location within the medical facility and the time since arrival is not accurately tracked. This can increase a medical risk associated with the patient if the patient currently has a life threatening medical condition.

There have been attempts to solve one or more of the problems associated with coding medical information. For example, U.S. Pat. No. 6,529,876 to Dart et al. entitled "Electronic template medical records coding system" describes a method and a computer program for use by health care providers for the production of accurate billing coding for care entered using established E/M codes."

U.S. Pat. No. 6,393,404 to Waters, et al. entitled "System and method for optimizing medical diagnosis, procedures and claims using a structured search space" describes a system and method for optimizing medical diagnosis, procedures and reimbursement claims using a structured search space."

U.S. Pat. No. 6,208,973 to Boyer, et al. entitled "Point of service third party financial management vehicle for the healthcare industry" describes a point of service third party adjudicated payment system and method which provides for the creation of an adjudicated settlement transaction at a point of service which designates the portion of the service to be paid by the third party payor and the portion to be paid by the customer."

U.S. Pat. No. 5,664,109, to Johnson et al. entitled "Method for extracting pre-defined data items from medical service records generated by health care providers," described "a central medical record repository for a managed health care organization accepts and stores medical record documents in any format from medical service providers. The repository then identifies the document using information automatically extracted from the document and stores the extracted data in a document database. The repository links the document to a patient by extracting from the document demographic data identifying the patient and matching it to data stored in a patient database. Data is extracted automatically from medical records containing 'unstructured' or free-form text by identifying conventional organization components in the text and is organized by executing rules that extract data with the aid of such information. Documents for a patient are retrieved by identifying the patient using demographic data."

U.S. Pat. No. 5,483,443 to Milstein, et al. entitled "Method for computing current procedural terminology codes from physician generated documentation" describes a process for calculating a Current Procedural Terminology ("CPT") code from input received from a physician or other medical professional."

Newman and Weller in a paper entitled "A Desk Supporting Computer-based Interaction with Paper Documents," ACM 0-89791-513-5/92/005-0587, Chicago, May 3-7, 1992, teaches accepting input from paper forms into a computer via an interface apparatus.

However, these inventions do not solve all of the problems associated with processing medical information when telemedicine is used. Thus, it would be desirable to help reduce the complexity of collecting patient encounter information and allow easy automated collection, processing and recording of medical information codes such as diagnosis codes, billing codes, insurance codes, etc. with telemedicine. It is also desirable to provide such medical codes in real-time during or shortly after an encounter with a patient from a telemedicine session.

SUMMARY OF THE INVENTION

In accordance with preferred embodiments of the present invention, some of the problems associated with processing medical records from telemedicine sessions are overcome. A method and system for automated medical records processing with telemedicine is presented.

The method and system includes plural electronic medical templates specifically designed such that they reduce the complexity and risk associated with collecting virtual patient encounter information, creating a medical diagnosis, tracking the patient through the medical processes during a telemedicine session and generate the appropriate number and type medical codes for a specific type of medical practice when processed. The medical codes and other types of processed virtual patient encounter information are displayed in real-time on electronic medical records and invoices immediately after a virtual patient encounter from a telemedicine visit.

The method and system also includes real-time processing applications that may allow easy and automated collection, processing, displaying and recording of medical codes (e.g., diagnosis codes, billing codes, insurance codes, etc.) with cloud computing including patient tracking for virtual patient encounters via telemedicine.

The foregoing and other features and advantages of preferred embodiments of the invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIGS. 2A and 2B are block diagrams illustrating a front side and a back side of an exemplary paper medical information template;

FIGS. 2A-2D, FIGS. 8-12 are copyright © 2001-2003 by Practice Velocity, LLC. All rights reserved;

FIG. 3 is a block diagram illustrating portions of the exemplary paper medical information template of FIG. 2;

FIG. 8 is a block diagram illustrating an exemplary HX matrix;

FIG. 9 is a block diagram illustrating an exemplary PX matrix;

FIG. 10 is a block diagram illustrating an exemplary CX matrix;

FIG. 11 is a block diagram illustrating an exemplary final E/M matrix for a new outpatient;

FIG. 12 is a block diagram illustrating an exemplary final E/M matrix for an established outpatient;

FIGS. 17-23 are copyright © by Practice Velocity, LLC. All rights reserved;

FIG. 17 is a block diagram of a screen shot of a first portion of an exemplary electronic medical information template;

FIG. 18 is a block diagram of a screen shot of a second portion of an exemplary electronic medical information template;

FIG. 19 is a block diagram of a screen shot of a third portion of an exemplary electronic medical information template;

FIG. 20 is a block diagram of a screen shot of a fourth portion of an exemplary electronic medical information template;

FIG. 21 is a block diagram of a screen shot of a fifth portion of an exemplary electronic medical information template;

FIG. 22 is a block diagram of a screen shot of a sixth portion of an exemplary electronic medical information template;

FIG. 23 is a block diagram of screen shot illustrating an exemplary first portion of a medical information template on a smart phone;

FIGS. 26A and 26B are a flow diagram illustrating a method for automated processing of electronic medical records with cloud computing;

FIGS. 35-37 are copyright © by Practice Velocity, LLC. All rights reserved;

FIG. 36 is a block diagram illustrating a Patients Note field from the Patient Demographics component of the PT matrix;

FIG. 37 is a block diagram illustrating an Edit Work Queues component;

FIGS. 39A, 39B, 39C, 39D, 39E and 39F are a flow diagram illustrating a method for automated processing of electronic medical records with telemedicine;

FIG. 40 is a block diagram illustrating an exemplary telemedicine patient tracking board screen;

FIG. 42 is a block diagram illustrating an exemplary telemedicine Documents screen.

DETAILED DESCRIPTION OF PREFERRED EMBODIMENTS

Medical Records System

Figure 1:
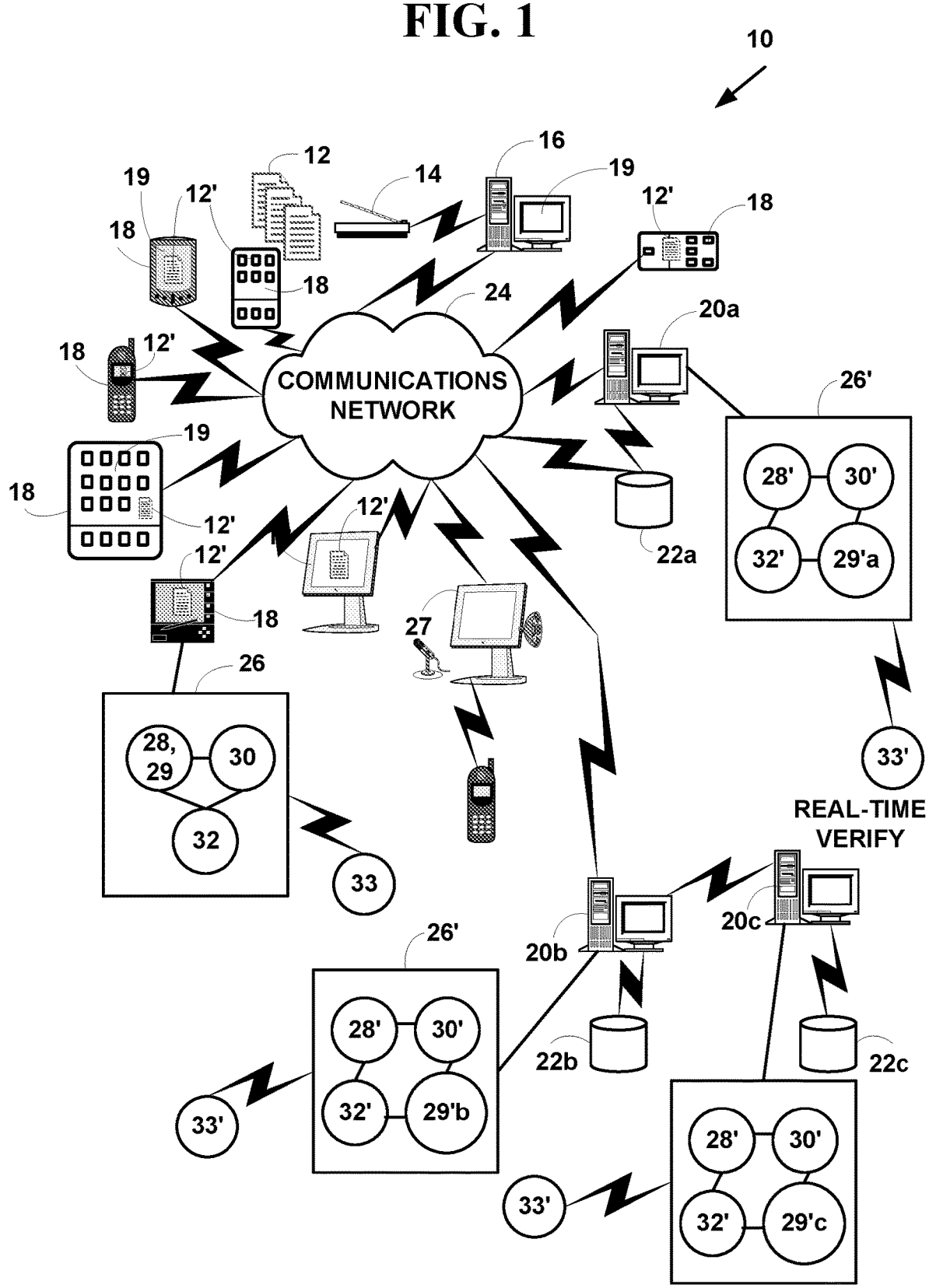
FIG. 1 is a block diagram illustrating an exemplary medical records system.
Figure 24:
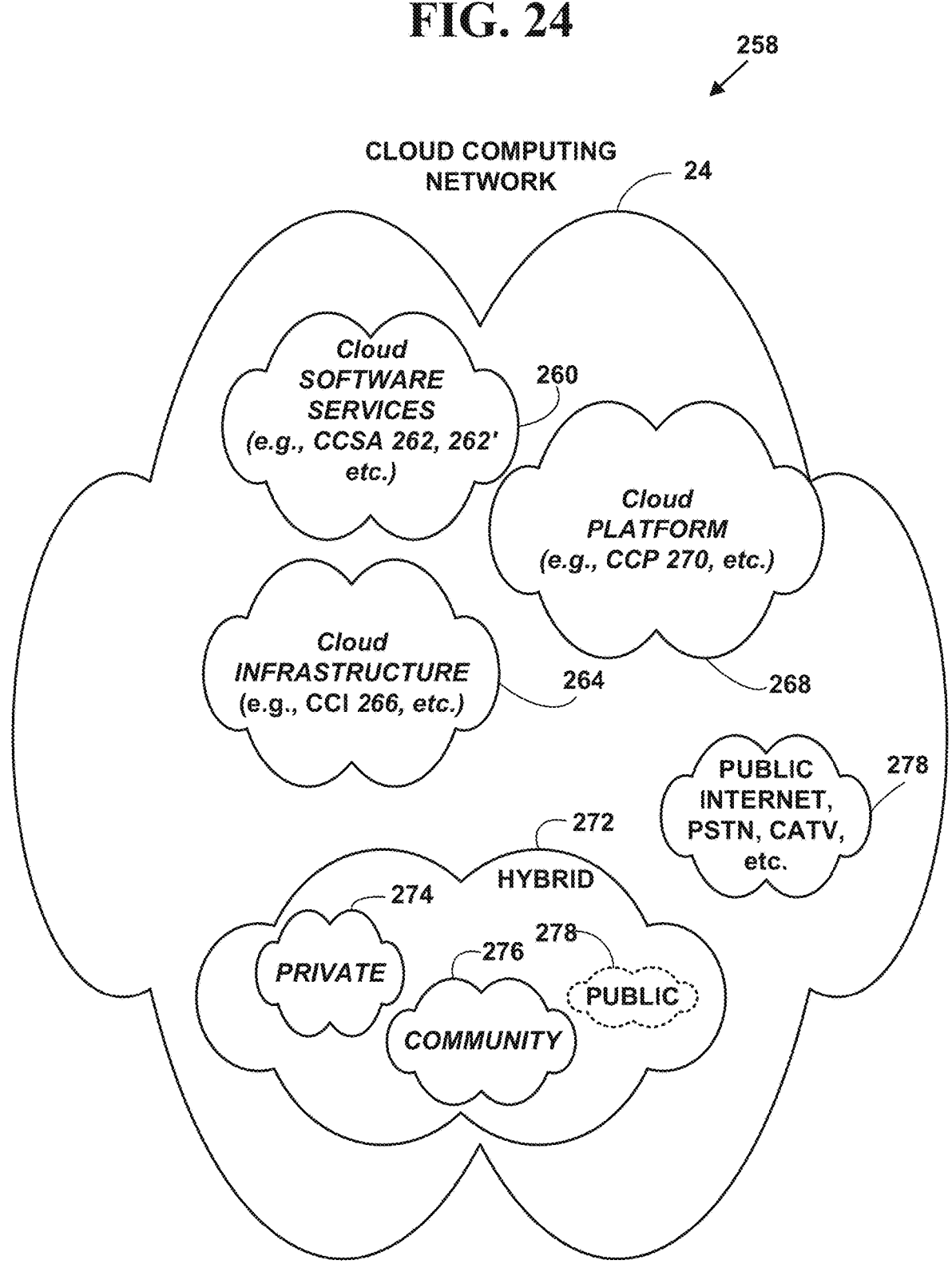
FIG. 24 is a block diagram illustrating an exemplary cloud computing network.

FIG. 1 is a block diagram illustrating an exemplary medical records system 10. The medical records system 10 includes plural medical information templates, including plural paper 12 medical information templates and plural electronic medical information templates 12', one or more electronic scanners 14 (one illustrated), one or more client computers 16 (one illustrated), one or more client network devices 18 each with a display component including a graphical user interface (GUI) 19, one or more server network devices 20a, 20b, 20c, and one or more databases 22a, 20b, 20c. The components of the medical records system 10 communicate via a communications network 24. The communications network 24 includes a cloud computing/communications network (FIG. 24).

The one or more different electronic medical information templates 12' are periodically, automatically and dynamically updated via the communications network 24 to reflect changes in medical, insurance and/or billing practices and/or codes. However, the present invention is not limited to these components, and more, fewer or other components can also be used to practice the invention.

The one or more client network devices 18 include plural software applications 26 (28, 29, 30, 32, 33, etc.) for displaying an electronic medical information template 12', collecting digital information from the electronic medical information templates 12', encrypting the collected digital information, for compressing and packaging the encrypted digital information and for securely transmitting the encrypted, compressed and packaged digital information.

The one or more client network devices 18 may include the information template reader application 28, a telemedicine application 29, a medical code processing engine 30, a medical data presentation application 32, and/or the digital image/data verification application 33, described below. However, the one or more client network devices 18 are not limited to these, and more, fewer or other applications and components can also be used on the one or more client network devices 18.

The client computers 16 include plural software applications 26 for scanning in paper medical information templates 12 from scanner 14 and creating one or more digital images, for encrypting the digital images created, for compressing and packaging the encrypted digital images and for securely transmitting the encrypted, compressed and packaged digital images. The client computers 16 may also include the medical information template reader application 28, a telemedicine application 29, a medical code processing engine 30, a medical data presentation application 32, and digital image/data verification application 33 described below. However, the client computers 16 are not limited to these, and more, fewer or other components can also be used on the client computers 16. The client computers 16 may be local or remotely located with respect to the scanner 14.

The client computers 16, client network devices 18 and/or server computers 20a, 20b, 20c include comprising plural processing applications 26. The plural processing applications 26 include, but are not limited to, a medical information template reader application 28, a telemedicine application 29, a medical code processing engine 30, a medical data presentation application 32 and a digital image/data verification application 33.

In one embodiment, applications 26 (28, 29, 30, 32 and 33) are applications for smart phones such as the iPhone by Apple, Inc., Blackberry Storm, by Research In Motion, Inc., Droid by Motorola, Inc., other types of smart phones, other types of mobile and non-mobile phones, etc. However, the present invention is not limited to such applications, and more, fewer or other software applications can also be used on the server computer 20a, 20b, 20c.

In one embodiment of the invention, the plural processing applications are software applications. However, the plural processing applications 26 can also include plural software, firmware, hardware applications and/or combinations thereof and the present invention is not limited to software processing applications. One or more applications (e.g., 28', 29', 30', 32', 33' etc.) on the server computers 20a, 20b, 20c continuously and dynamically updates electronic medical templates 12' on the client network devices 18 and the client computers 16. The server computers 20a, 20b, 20c may be local or remote to the client computers 16 and client network devices 18.

The database 22a, 22b, 22c comprise a relational database. However, the present invention is not limited to a relational database and other types of databases can also be used.

The communications network 24 includes a wired or wireless communications network including components of the Public Switched Telephone Network ("PSTN"), the Internet, intranets, or types of wired or wireless, including voice and data communications networks, and including local area networks ("LAN") and wide area networks ("WAN").

The server computers 20a, 20b, 20c, the client computers 16 and client network devices 18 include wired and wireless interfaces to communicate with the communication network 24. The communications network 24 includes a wire or wireless, telecommunications network and/or a wired and/or wireless data network (e.g., Internet Protocol (IP) suite of protocols including Transmission Control Protocol (TCP), User Datagram Protocol (UDP), etc.).

In one embodiment of the present invention, the wired interfaces corresponding networking protocols for wired connections to the Public Switched Telephone Network (PSTN) or a cable television network (CATV) including HDTV or the Internet that connect the computers and network devices via one or more twisted pairs of copper wires, digital subscriber lines (e.g. DSL, ADSL, VDSL, etc.) coaxial cable, fiber optic cable, other connection media or other connection interfaces. The PSTN is any public switched telephone network provided by AT&T, GTE, Sprint, MCI, SBC, Verizon and others.

In one embodiment, of the invention, the wireless interfaces include WPAN wireless personal area network (WPAN) interfaces. WPAN is a personal area network for interconnecting devices centered around an individual person's devices in which the connections are wireless. A WPAN interconnects all the ordinary computing and communicating devices that a person has on their desk (e.g. computer, etc.) or carry with them (e.g., PDA, mobile phone, two-way pager, etc.)

Typically, a wireless personal area network uses some technology that permits communication only within about 10 meters. One such technology is "Bluetooth." Another such technology is "Zigbee."

A key concept in WPAN technology is known as "plugging in." In the ideal scenario, when any two WPAN-equipped devices come into close proximity (within several meters of each other) or within a few kilometers of a central server (not illustrated), they can communicate via wireless communications as if connected by a cable. WPAN devices can also lock out other devices selectively, preventing needless interference or unauthorized access to secure information.

In one embodiment of the present invention, the wireless interfaces include but are not limited to, an IEEE 802.11a, 802.11b, 802.11g, 802.11n, 802.15.4 (ZigBee), 802.16a, 802.16g, Wireless Fidelity (Wi-Fi), Worldwide Interoperability for Microwave Access (WiMAX), ETSI High Performance Radio Metropolitan Area Network (HIPERMAN), Z-wave, Bluetooth, Infrared, Industrial, Scientific and Medical ("SM"), Radio Frequency Identifier (RFID), Near field communication (NFC), Machine-2-Machine (M2M), or other types of wireless interfaces. However, the present invention is not limited to such wireless interface and other types of wireless interfaces can also be used.

In another embodiment of the present invention, the wireless interface includes a wireless sensor device that comprises an integral or separate Bluetooth and/or infra data association (IrDA) module for wireless Bluetooth or wireless infrared communications.

802.11b is a short-range wireless network standard. The IEEE 802.11b standard defines wireless interfaces that provide up to 11 Mbps wireless data transmission to and from wireless devices over short ranges. 802.11a is an extension of the 802.11b and can deliver speeds up to 54M bps. 802.11g deliver speeds on par with 802.11a. However, other 802.11xx interfaces can also be used and the present invention is not limited to the 802.11 protocols defined. The IEEE 802.11a, 802.11b and 802.11g standards are incorporated herein by reference.

Wi-Fi is a type of 802.11xx interface, whether 802.11b, 802.11a, dual-band, etc. Wi-Fi devices include an RF interfaces such as 2.4 GHz for 802.11b or 802.11g and 5 GHz for 802.11a.

802.15.4 (Zigbee) is low data rate network standard used for mesh network devices such as sensors, interactive toys, smart badges, remote controls, and home automation. The 802.15.4 standard provides data rates of 250 kbps, 40 kbps, and 20 kbps., two addressing modes; 16-bit short and 64-bit IEEE addressing, support for critical latency devices, such as joysticks, Carrier Sense Multiple Access/Collision Avoidance, (CSMA-CA) channel access, automatic network establishment by a coordinator, fully handshaked protocol for transfer reliability, power management to ensure low power consumption for multi-month to multi-year battery usage and up to 16 channels in the 2.4 GHz ISM band (Worldwide), 10 channels in the 915 MHz (US) and one channel in the 868 MHz band (Europe). The IEEE 802.15.4-2003 standard is incorporated herein by reference.

WiMAX is an industry trade organization formed by leading communications component and equipment companies to promote and certify compatibility and interoperability of broadband wireless access equipment that conforms to the IEEE 802.16XX and ETSI HIPERMAN. HIPERMAN is the European standard for metropolitan area networks (MAN).

The IEEE The 802.16a and 802.16g standards are wireless MAN technology standard that provides a wireless alternative to cable, DSL and T1/E1 for last mile broadband access. It is also used as complimentary technology to connect IEEE 802.11XX hot spots to the Internet.

The IEEE 802.16a standard for 2-11 GHz is a wireless MAN technology that provides broadband wireless connectivity to fixed, portable and nomadic devices. It provides up to 50-kilometers of service area range, allows users to get broadband connectivity without needing direct line of sight with the base station, and provides total data rates of up to 280 Mbps per base station, which is enough bandwidth to simultaneously support hundreds of businesses with T1/E1-type connectivity and thousands of homes with DSL-type connectivity with a single base station. The IEEE 802.16g provides up to 100 Mbps.

The IEEE 802.16e standard is an extension to the approved IEEE 802.16/16a/16g standard. The purpose of 802.16e is to add limited mobility to the current standard which is designed for fixed operation.

The ESTI HIPERMAN standard is an interoperable broadband fixed wireless access standard for systems operating at radio frequencies between 2 GHz and 11 GHz.

The IEEE 802.16a, 802.16e and 802.16g standards are incorporated herein by reference. WiMAX can be used to provide a WLP.

The ETSI HIPERMAN standards TR 101 031, TR 101 475, TR 101 493-1 through TR 101 493-3, TR 101 761-1 through TR 101 761-4, TR 101 762, TR 101 763-1 through TR 101 763-3 and TR 101 957 are incorporated herein by reference. ETSI HIPERMAN can be used to provide a WLP.

Z-wave is a wireless communications protocol used primarily for mesh networks. It is a mesh network protocol using low-energy radio waves to communicate between Internet of Things (IoT) network devices, allowing for wireless control of IoT devices. Z-Wave uses Part 15 of the ISM band. It operates at 908.42 MHz in the U.S. and Canada and as other frequencies in other countries. Recently, the International Telecommunications Union (ITU) included the Z-Wave physical and media access control (MAC) layers as an option in its new G.9959 standard, which defines a set of guidelines for sub-1-GHz narrowband wireless devices. The ITU G.9959 standard is incorporated by reference.

The Internet of things (IoT) is an inter-networking of physical devices, appliances, controllers buildings, and other items embedded with electronics, software, sensors, actuators, and network connectivity that enable these objects to collect and exchange data and interact with a communications network like the Internet, etc.

In 2013, the Global Standards Initiative on Internet of Things (IoT-GSI) defined the IoT as "an infrastructure of an information society." The IoT allows objects to be sensed or controlled remotely across existing network infrastructure, creating opportunities for more direct integration of the physical world into computer-based systems, and resulting in improved efficiency, accuracy and economic benefit in addition to reduced human intervention.

Each IoT "thing" is uniquely identifiable through its embedded computing system but is able to interoperate within the existing Internet infrastructure. Experts estimate that the IoT will comprise almost 50 billion devices by 2020.

In a preferred embodiment, the network devices 18 include an Internet of Things (IoT) network device with one or more processors, one or more sensors and/or one or more actuators and a network connection interface.

An "actuator" is a component of the IoT network device 18 that is responsible for moving or controlling a mechanism or system.

An actuator requires a control signal and a source of energy. The control signal is relatively low energy and may be electric voltage or current, pneumatic or hydraulic pressure, or even human power. The supplied main energy source may be electric current, hydraulic fluid pressure, pneumatic pressure or other energy source. When the control signal is received, the actuator responds by converting the energy into mechanical motion.

A "sensor" an electronic component, or subsystem whose purpose is to detect events or changes in its environment (e.g., temperature, pressure, altitude, elevation, speed, acceleration, etc.) and send the information to other electronics and one or more processors.

The IoT network devices 18, include but are not limited to, security cameras, doorbells with real-time video cameras, baby monitors, televisions, set-top boxes, lighting, heating (e.g., smart thermostats, etc.), ventilation, air conditioning (HVAC) systems, and appliances such as washers, dryers, robotic vacuums, air purifiers, ovens, refrigerators, freezers, toys, game platform controllers, game platform attachments (e.g., guns, googles, sports equipment, etc.), and/or other IoT devices 18.

In one embodiment, the IoT devices 18 include medical equipment network devices as radiology devices, lab test devices, scanning devices (e.g., CAT, etc.).

Bluetooth (IEEE 802.15.1a) is a short-range radio frequency technology aimed at simplifying communications among network devices and between network devices. Bluetooth wireless technology supports both short-range point-to-point and point-to-multipoint connections. The Bluetooth Specification, GL 11r02, March 2005, prepared by the Bluetooth SIG, Inc. and the IEEE 802.15.1a standard are incorporated herein by reference.

Infra data association (IrDA) is a short-range radio wireless Bluetooth or wireless infrared communications.

Industrial, Scientific and Medical (ISM) are short-range radio wireless communications interfaces operating at 400 MHz, 800 MHz, and 900 Mhz. ISM sensors may be used to provide wireless information to practice the invention.

An RFID is an automatic identification method, relying on storing and remotely retrieving data using devices called RFID tags or transponders. An RFID tag is a small object that can be attached to or incorporated into a product, animal, or person. RFID tags contain antennas to enable them to receive and respond to radio-frequency queries from an RFID transceiver. Passive tags require no internal power source, whereas active tags require a power source 31. RFID sensors and/or RFID tags are used to provide wireless information to practice the invention.

Passive tags are powered by received radiation from a reading device and require no internal source of power; thus, they can be manufactured at very low cost and require no ongoing maintenance as long as they are not removed or physically damaged. Passive tags can only be read by a reader device in close proximity to the tag.

RFID Passive tags can be manufactured in a sticker-like form factor and held in place by adhesive, providing very low installation cost; however, such an arrangement is not heat-resistant, and conventional mechanical mounting employing screws or cover plates is advisable for at least a minimal subset of all installed tags.

RFID Passive tags are typically capable of providing a 96-bit number to a tag reader: 96 bits allow $2^{96}=10^{29}$ (100 billion billion billion) possible codes, ample to allow unique identification.

RFID active tags may also be employed for location awareness. Active tags have longer range and can include more sophisticated functionality.

RFID Active tags are also deployed in a mesh network that would allow information to pass from tag to tag. This type of network would allow tag and reader information to be passed from location to location and possibly from floor to floor to move the information to a central location or to the building wall ultimately making it easier to access. Active tag networks have significant functional advantages, but are relatively expensive and maintenance-intensive compared to passive tags.

In one embodiment, the apparatus 12 communicates with other network devices with near field communications (NFC) and/or machine-to-machine (M2M) communications.

"Near field communication (NFC)" is a set of standards for smartphones and similar devices to establish radio communication with each other by touching them together or bringing them into close proximity, usually no more than a few centimeters. Present and anticipated applications include contactless transactions, data exchange, and simplified setup of more complex communications such as Wi-Fi. Communication is also possible between an NFC device and an unpowered NFC chip, called a "tag" including radio frequency identifier (RFID) tags.

NFC standards cover communications protocols and data exchange formats, and are based on existing radio-frequency identification (RFID) standards including ISO/IEC 14443 and FeliCa. These standards include ISO/IEC 1809 and those defined by the NFC Forum, all of which are incorporated by reference.

"Machine to machine (M2M)" refers to technologies that allow both wireless and wired systems to communicate with other devices of the same ability. M2M uses a device to capture an event (such as option purchase, etc.), which is relayed through a network (wireless, wired cloud, etc.) to an application (software program), that translates the captured event into meaningful information. Such communication was originally accomplished by having a remote network of machines relay information back to a central hub for analysis, which would then be rerouted into a system like a personal computer.

However, modern M2M communication has expanded beyond a one-to-one connection and changed into a system of networks that transmits data many-to-one and many-to-many to plural different types of devices and appliances. The expansion of IP networks across the world has made it far easier for M2M communication to take place and has lessened the amount of power and time necessary for information to be communicated between machines.

In one embodiment, of the invention, the wireless interfaces include: a wireless messaging, wireless cellular telephone, wireless cellular telephone data, Packet Cellular Network (PCN), Global System for Mobile Communications, (GSM), Generic Packet Radio Services (GPRS), Personal Communications Services network (PCS), Cellular Digital Packet Data (CDPD), Wireless Application Protocol (WAP), Digital Audio Broadcasting (DAB) network, Voice over IP (VoIP) network or other types of wireless networks.

The wireless cellular telephone network includes, but is not limited to Code Division Multiple Access (CDMA), Time Division Multiple Access (TDMA), or other wireless technologies.

PCS networks include network that cover a range of wireless, digital communications technologies and services, including cordless phones, mobile phones, voice mail, paging, faxing, mobile personal digital/data assistants (PDAs), etc. PCS devices are typically divided into narrowband and broadband categories.

Narrowband devices, which operates in the 900 MHz band of frequencies, typically provide paging, data messaging, faxing, and one- and two-way electronic messaging capabilities. Broadband devices, which operate in the 1850 MHz to 1990 MHz range typically provide two-way voice, data, and video communications. Other wireless technologies such as GSM, CDMA and TDMA are typically included in the PCS category.

GSM is another type of digital wireless technology widely used throughout Europe, in Australia, India, Africa, Asia, and the Middle East. GSM is gaining popularity in the United States. GSM is a wireless platform based on TDMA to digitize data. GSM includes not only telephony and Short Message Services (SMS) but also voice mail, call forwarding, facsimile, caller ID, Internet access, and e-mail.

SMS is type of communications service that enables a user to allow private message communications with another user. GSM typically operates at three frequency ranges: 900 MHz (GSM 900) in Europe, Asia and most of the rest of the world; 1800 MHz (GSM 1800 or DCS 1800 or DCS) in a few European countries; and 1900 MHz (GSM 1900 also called PCS 1900 or PCS) in the United States. GSM also operates in a dual-band mode including 900/1800 Mhz and a tri-band mode include 900/1800/1900 Mhz.

GPRS is a standard for wireless communications, which runs at speeds up to 150 kilo-bits-per-second ("kbit/s"). GPRS, which supports a wide range of bandwidths is an efficient use of limited bandwidth and is particularly suited for sending and receiving small bursts of data such as e-mail and Web browsing, as well as large volumes of data.

CDPD is a wireless standard providing two-way, 19.2-Kbps or higher packet data transmission over existing cellular telephone channels. A Packet Cellular Network (PCN) includes various types of packetized cellular data.

The medical records system further includes a secure audio dictation interface 27. The audio dictation interface 27 allows a provider to securely access the medical records system 10 (e.g., via a secure web-page, secure dial-in, secure voice-mail, etc.) and dictate audio information via a microphone such as those attached to a computer, mobile phone, personal digital assistant ("PDA"), etc. The dictated audio information is then stored in database 22 as an audio file in an appropriate audio format (e.g., a MIDI, WAVE, MP3, or other audio format). The audio dictation interface 27 also allows a medical transcriptionist to securely access a saved audio file and transcribe the audio information into electronic text. The electronic text is saved in database 22 and is associated with an electronic medical record created for a patient encounter as is explained below.

An operating environment for components of the medical the medical records system 10 include a processing system with one or more high speed Central Processing Unit(s) ("CPU") and a memory or other computer readable mediums. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU executed" or "processor executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected or distributed computer readable medium, which exist exclusively on the processing system or be distributed among multiple interconnected processing systems that may be local or remote to the processing system and may be accessed by one or more CPUs or processors.

Preferred embodiments of the present invention include computers, servers network devices and interfaces that are compliant with all or part of standards proposed by the Institute of Electrical and Electronic Engineers ("IEEE"), International Telecommunications Union-Telecommunication Standardization Sector ("ITU"), European Telecommunications Standards Institute (ETSI), Internet Engineering Task Force ("IETF"), U.S. National Institute of Security Technology ("NIST"), American National Standard Institute ("ANSI"), Wireless Application Protocol ("WAP") Forum, Bluetooth Forum, or the ADSL Forum. However, network devices based on other standards could also be used.

Medical Information Templates

Figure 2A:
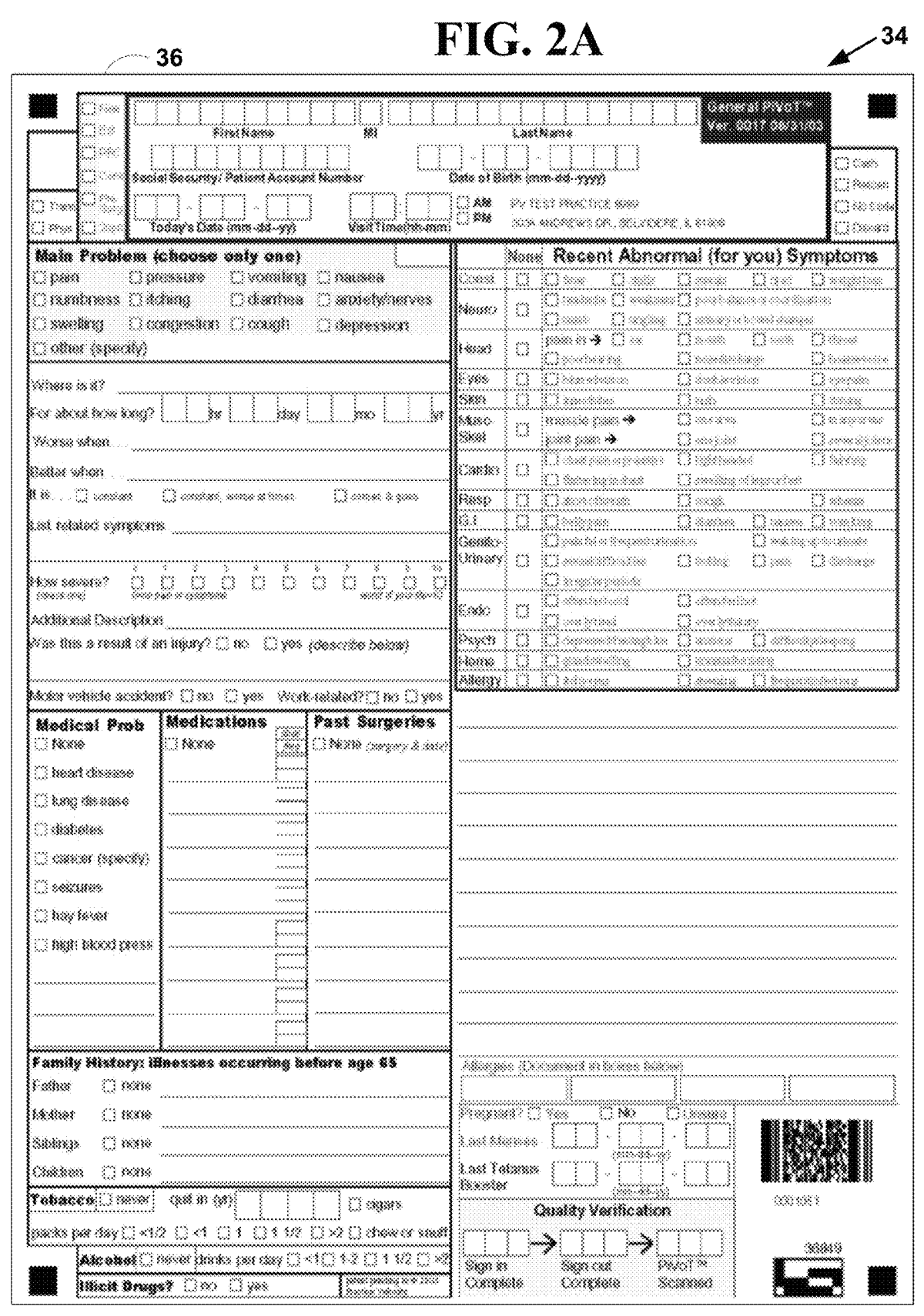
Figure 2B:
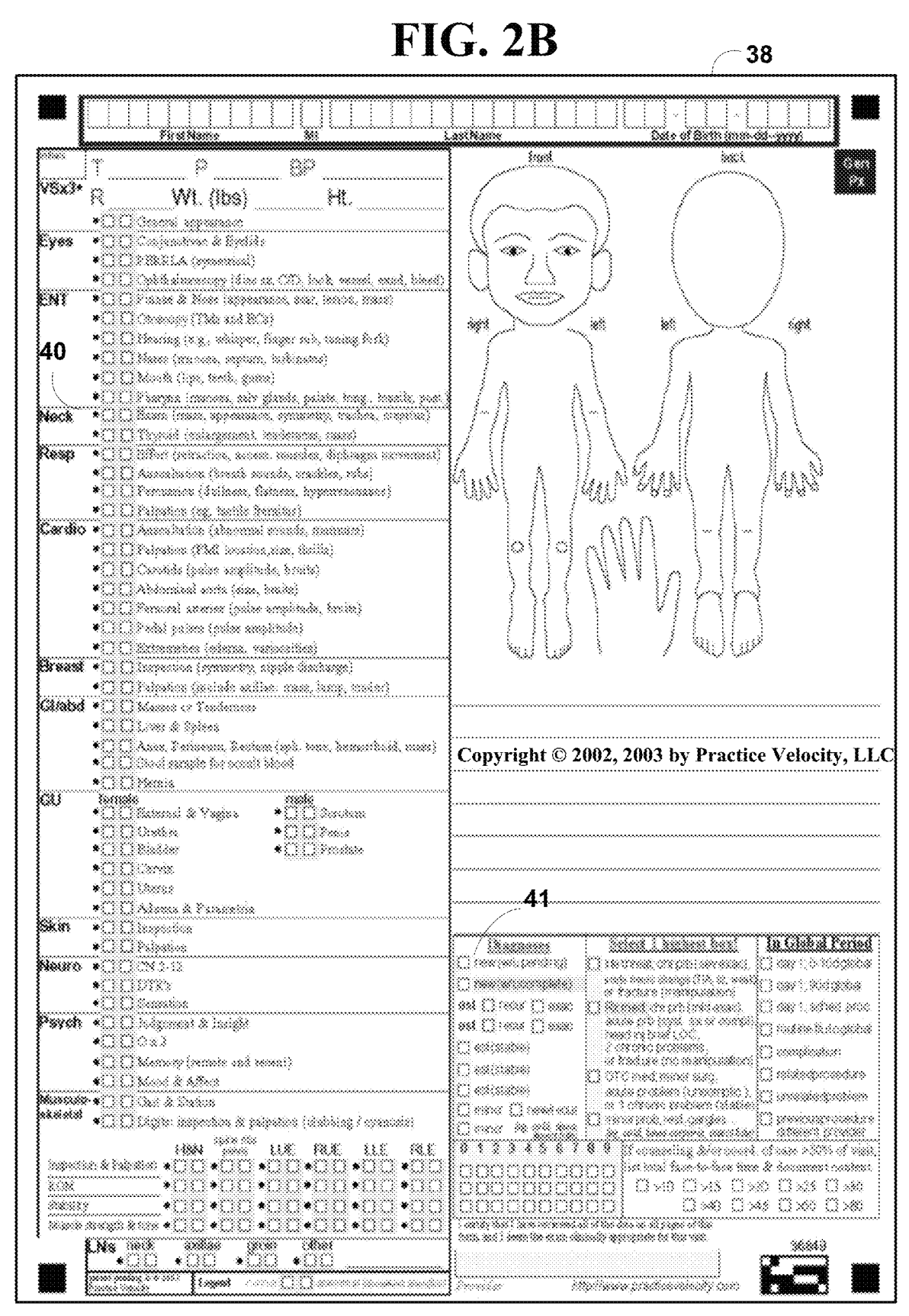
Figure 2C:
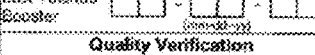
FIGS. 2C and 2D are a block diagram illustrating a front side and a back side of another exemplary paper medical information form that further illustrates an exemplary coding summary produced from exemplary patient encounter information.

FIGS. 2A and 2B are a block diagram 34 illustrating an exemplary paper medical information template 12 including a front side 36 (FIG. 2A) and a back side 38 (FIG. 2B). FIGS. 2A-2D and FIGS. 8-12 are copyright © 2002-2003 by Practice Velocity, LLC. All rights reserved.

Exemplary paper medical information template 34 is an exemplary medical information template 34 from the set of plural paper 12 and electronic 12' medical information templates used, including plural different medical practice templates used for example, in a family practice office, emergency room, urgent care, or walk-in clinic or for any appropriate medical practice. Such a paper or electronic information template 34 is used by providers and other clinical personnel to complete documentation of history, physical exam, complexity of medical decision making, and other relevant information for an encounter with a patient.

The plural medical information templates 12 also include specialized paper medical information templates (not illustrated) such as those used for pediatrics, obstetrics and gynecology, cardiology, neurology, etc. Such specialized paper medical information templates are configured and laid out similar to the exemplary paper medical information template 34 of FIG. 2 and are used to complete documentation for history, physical exam, complexity of medical decision making and other relevant information in a specialized area of medicine (e.g., for a physician with a specialized medical practice).

The plural medical information templates also include general and specialized electronic medical information templates 12' (FIGS. 17-23) that can be displayed and used on desktop and handheld network devices 18. The electronic medical information templates 12' can be displayed on desktop electronic devices such as computers, etc. or other types of desktop network devices 18. The electronic medical information templates can also be displayed and used on hand-held electronic devices, such as, personal digital/data assistants ("PDA"), electronic tablets, (e.g., IPAD, by APPLE, KINDLE by AMAZON, etc.), Internet appliances, mobile phones, smart phones such as the iPhone by Apple, Inc., Blackberry Storm and other models, by Research In Motion, Inc., Droid by Motorola, Inc, other smart phones and mobile phones, etc., electronic gaming platforms (e.g., Play Station Portable (PSP) by Sony, the Gameboy and DS by Nintendo, etc.) or other types of handheld client network devices 18. The network devices 18 further include wearable network devices (FIG. 33), Internet of Things (IoT) network devices, network devices capable of displaying three dimensional (3D) information for viewing.

Returning to FIG. 2, the paper medical information template 34 is designed such that the plural processing applications 26 may read and/or interpret data from a digital image made of a paper copy of a medical information template 34, or directly from electronic medical information templates 12' created for an electronic device.

The paper medical information template 34 includes a limited number of check boxes, blanks and diagrams or other pre-denoted fields to fill in. The limited number of choices helps reduce the amount and/or complexity of data to be reviewed and the number of diagnostic options to be considered while at the same time helping ensure the appropriate number and type medical codes will be generated for the patient encounter.

The medical information templates 12, 12' including exemplary paper medical information template 34, are not used as documents where diagnostic information is entered by a provider or other clinical personnel, where the responsibility for deciphering and selecting the appropriate codes is then performed directly by a physician or transferred to a person with knowledge of medical coding and medical codes (corresponding to various diagnoses, procedures or services), who manually enters the appropriate medical codes into a document or a medical records systems.

Instead, the plural medical information templates 12, 12' are designed and laid out in a format that systematically documents the specific information, corresponding to medical codes that are a collection of the most common and most likely to encountered for a specific type of general or specialized medical practice. By simply completing the medical information templates 12, 12' during a patient encounter, the physician (or other skilled medical personnel such as nurses, physician assistants, etc.) will cause many, if not all, of the proper medical coding to be automatically generated when the electronic images of the templates are processed by the medical records system 10.

When they are processed by the medical records system 10, the plural medical information templates 12, 12' allow automatic generation and display in real-time, of the proper medical and insurance codes typically used by medical and health care providers for general and specific types of medical diagnosis's (e.g., emergency room or walk-in clinic diagnosis, specialized medical practices, etc.). The design and layout of the plural medical information templates 12, 12' also allows automatic easy and efficient processing by the medical records system 10 and other types of data processing systems such as billing and invoicing systems The plural medical information templates 12, 12' may simplify documentation using any of the following methods: (1) reducing the complexity associated with choosing the correct level of medical decision making by allowing only a small number of check boxes (or other easily-denoted fields) for each level of risk; (2) eliminate the use of amount and/or complexity of medical data to be reviewed. Selected data may be eliminated on templates designed for practices where extensive review of such data is very rare. However, check boxes (or other easily-denoted fields) for other data may be placed on templates for medical practices where use of this category is helpful for determining a proper level of CPT E/M coding; (3) limiting and categorizing a number of diagnoses or management options thereby further reducing risk and complexity. Check boxes (or other easily-denoted fields) are used directly for categorizing the number of diagnoses or management options. The check boxes (or other easily-denoted fields) are limited in number to those in each category allowed by current coding guidelines. The provider may check as many as possible, but can not check too many, as the check boxes on the template are limited as noted above; (4) electronically process, display and utilize in real-time patient encounter information recorded on a paper medical template 12 after the paper medical template has been converted into a digital image; (5) help electronically process, display, and utilize in real-time data recorded on electronic medical templates 12' after the electronic medical information template has been processed; and (6) allow easy changes of coding definitions. If coding definitions are changed by any entity, changes are easily made within the method and system. The one or more different electronic medical templates are continuously and dynamically updated on the client network devices 18 via the communications network 24.

FIG. 2B also includes an exemplary information area 40 with four check-boxes for the Neck as is explained in connection with FIG. 3. In addition, FIG. 2B illustrates an exemplary information area 41 with plural check boxes for completing a medical diagnosis as is explained below in connection with Table 3.

FIG. 3 is a block diagram 42 illustrating portions of the exemplary paper medical information template 34 from FIG. 2B. For example, the exemplary paper medical information template 34 on its back side 38 (FIG. 2B) includes a box labeled "Neck" 40 and a box labeled "Diagnoses" 41.

A Neck box 40 (FIG. 3) includes two columns of check boxes 44, 46 typically identified by colors including for example, green and red. The green check box is the first or leftmost check box and the red check box is the second or rightmost check box. The green check box indicates the provider examined the patient, but the patient does not have any abnormality in the indicated body area or system. The red check box indicates the provider examined the patient, but the patient does have one or more abnormalities in the indicated body area or system. However, the exemplary paper medical information template 34 is not limited to such check boxes and other colors, other designations and other layouts for the check boxes can also be used.

For example, the Neck box 40 includes a first row 48 labeled "Exam (mass, appearance, symmetry, trachea, crepitus)" and a second row 40 labeled "Thyroid (enlargement, tenderness, mass)."

The information in these rows may include some or all of the specified physical exam items from the published guidelines for CPT E/M codes related to the neck. Thus, a physician's (or other skilled medical personnel) with no knowledge or a large amount of knowledge of medical coding practices can use the medical information template efficiently. In both situations, the proper medical codes are generated automatically for the patient encounter. Coding is not based on the coding knowledge of the provider (or other skilled medical personnel), but rather on the actual documentation of the encounter on the patient's medical record.

During an examination of the patient, the provider might check the patient's neck if the patient was in an automobile accident or otherwise complained of neck pain. If the patient's neck exam was normal, the physical would check the green check box column 44 of the first row 48 in the Neck box 38. (See FIG. 2D).

If the patient's neck exam was abnormal, the provider would check the red check box column 46 of the first row 48 in the Neck box 40.

The provider need not specify and document the actual abnormality using handwritten, typed text, voice dictation, or choose from a list of specific abnormal conditions. A similar procedure would be followed during the examination of the patient's Thyroid in the second row 50 of the Neck box 40.

Diagnoses box 41 includes check boxes for new and established diagnoses. It also includes a range of possible levels of medical diagnoses from minor to complex as is explained below.

The plural medical information templates 12, including exemplary paper medical information template 34, are scanned into the medical records system 10 via scanner 14. Patient encounter information is collected from the plural electronic medical information templates 12' via a number of other methods via a communications connection established with the server computers 20a, 20b, 20c via the communications network 24 (e.g., infrared connection, or other wired or wireless connection via a Personal Digital Assistant ("PDA"), mobile phone, etc.).

The data on the plural medical information templates 12, 12' is used for multiple purposes including (but not limited to) those purpose illustrated in Table 1a. However, the present invention is not limited to the purposes limited in Table 1a and more, fewer or other purposes can also be used to practice the invention.

TABLE 1a

1. Coding of and/or billing for Evaluation and Management codes ("E/Ms") codes in real-time.

TABLE 1a-continued

2. Coding of and/or billing for Current Procedural Terminology ("CPTs") codes in real-time.
3. Coding of and/or billing for Health Care Financing Administration Common Procedural Coding System ("HCPCS") codes in real-time.
4. Coding of and/or billing for International Classification of Diseases ("ICD-9") $9^{th}$ or $10^{th}$ ("ICD-10") Edition Clinical Modification codes in real-time.
5. Coding of modifiers to be attached to the above-generated codes.
6. Coding of and/or billing for other codes for medical services as defined by governmental agencies, medical associations, insurance companies, other payers, or any other entity that creates or defines codes or a system of codes for the purposes of documenting and/or billing medical services or supplies in real-time.
7. Production of a paper or electronic invoice 75 (FIG. 4) in real-time immediately after a patient encounter using one or more of the medical codes described in 1-5.
8. Production an electronic medical record in real-time immediately after a patient encounter using or more of the medical codes described in 1-5.
9. Production of other plural electronic templates used to display patient encounter information in real-time.
10. Evaluating the medical data for regulatory compliance (e.g., HIPAA, etc.)
11. Evaluating appropriateness of medical care.
12. Production of text documents through electronic conversion of data on the paper medical record into an electronic medical record.
13. Evaluating patterns of physician practices.
14. Gathering data for medical research.
15. Utilizing generated medical codes in other data processing systems such as other billing and invoicing systems.
16. Other applications deemed appropriate for use of this data while protecting its privacy.

Data Flow in the Medical Records System

Figure 4:
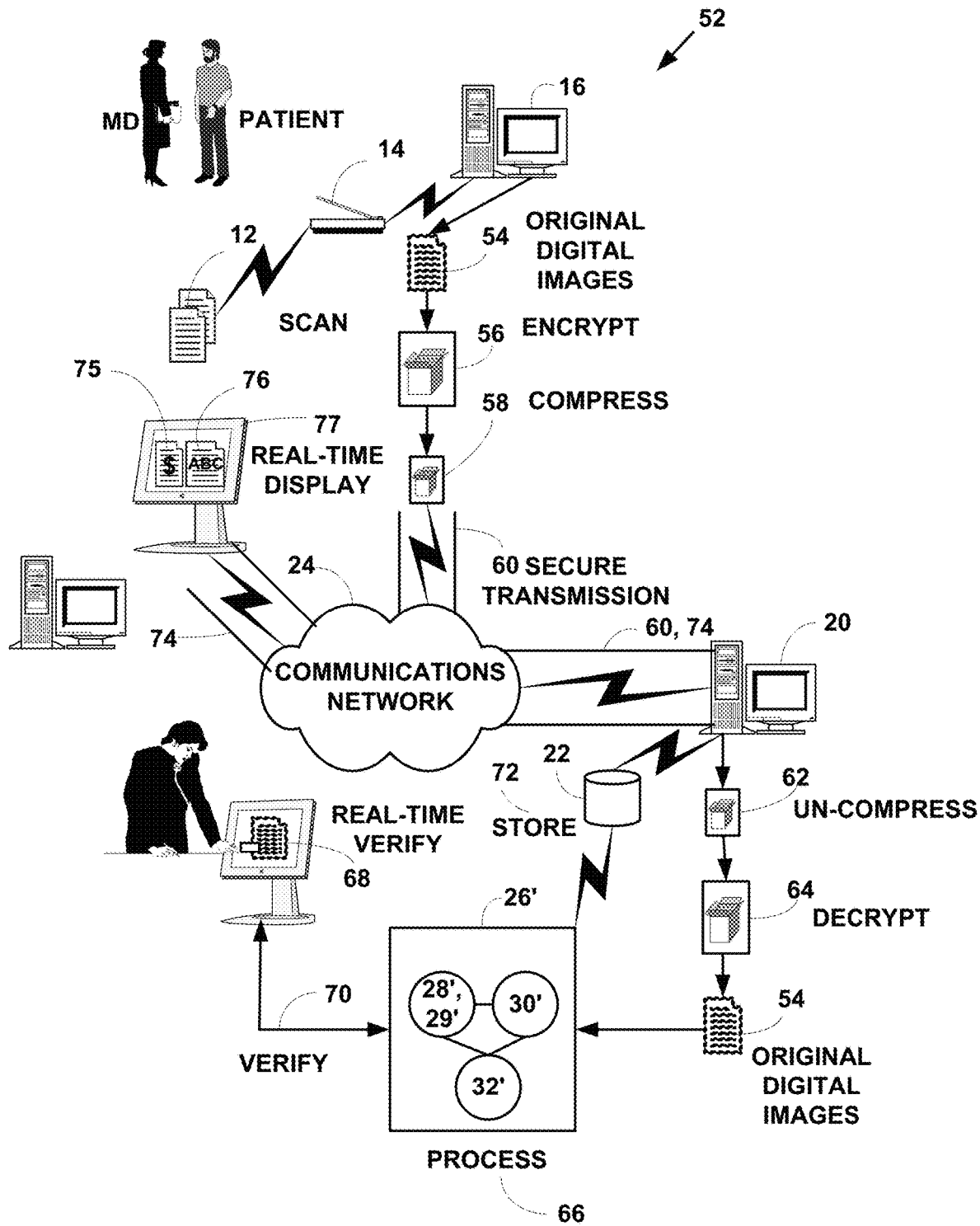
FIG. 4 is a block diagram illustrating an exemplary data flow for the medical records system of FIG. 1 for a paper medical information template.

FIG. 4 is a block diagram illustrating an exemplary data flow 52 for the medical records system 10 for a paper medical information template 12. The data flow 52 includes scanning a paper medical information template 12 (e.g., paper medical information template 34 of FIGS. 2A and 2B) into one or more digital images 54 with a pre-determined image format such as a Tagged Image Format ("TIF") or other types of digital image formats (e.g., Bit Map ("BMP"), Graphics Interchange Format ("GIF"), Joint Pictures Expert Group ("JPEG"), etc.) known in the art, with scanner 14. The paper medical record may also be scanned into other digital formats (e.g., other types of digital data) and the invention is not limited to scan the paper medical information template into a digital image.

The digital images are encrypted 56 to ensure the data it includes is protected and kept private. For example, the digital images may be encrypted using RSA encryption, Data Encryption Standard ("DES") encryption, Advanced Encryption Standard ("AES") encryption, or other encryption methods known in the art.

Devices and interfaces of the present invention include various types of security and encryption. Wireless Encryption Protocol ("WEP") (also called "Wired Equivalent Privacy") is a security protocol for WiLANs defined in the IEEE 802.11b standard. WEP is cryptographic privacy algorithm, based on the Rivest Cipher 4 (RC4) encryption engine, used to provide confidentiality for 802.11b wireless data.

RC4 is cipher designed by RSA Data Security, Inc. of Bedford, Mass., which can accept encryption keys of arbitrary length, and is essentially a pseudo random number generator with an output of the generator being XORed with a data stream to produce encrypted data.

One problem with WEP is that it is used at the two lowest layers of the OSI model, the physical layer and the data link layer, therefore, it does not offer end-to-end security. One another problem with WEP is that its encryption keys are static rather than dynamic. To update WEP encryption keys, an individual has to manually update a WEP key. WEP also typically uses 40-bit static keys for encryption and thus provides "weak encryption," making a WEP device a target of hackers.

The IEEE 802.11 Working Group is working on a security upgrade for the 802.11 standard called "802.11i." This supplemental draft standard is intended to improve WiLAN security. It describes the encrypted transmission of data between systems 802.11X WiLANs. It also defines new encryption key protocols including the Temporal Key Integrity Protocol (TKIP). The IEEE 802.11i draft standard, version 4, completed Jun. 6, 2003, is incorporated herein by reference.

The 802.11i is based on 802.1x port-based authentication for user and device authentication. The 802.11i standard includes two main developments: Wi-Fi Protected Access ("WPA") and Robust Security Network ("RSN").

WPA uses the same RC4 underlying encryption algorithm as WEP. However, WPA uses TKIP to improve security of keys used with WEP. WPA keys are derived and rotated more often than WEP keys and thus provide additional security. WPA also adds a message-integrity-check function to prevent packet forgeries.

RSN uses dynamic negotiation of authentication and selectable encryption algorithms between wireless access points and wireless devices. The authentication schemes proposed in the draft standard include Extensible Authentication Protocol ("EAP"). One proposed encryption algorithm is an Advanced Encryption Standard ("AES") encryption algorithm.

Dynamic negotiation of authentication and encryption algorithms lets RSN evolve with the state of the art in security, adding algorithms to address new threats and continuing to provide the security necessary to protect information that WiLANs carry.

The NIST developed a new encryption standard, the Advanced Encryption Standard ("AES") to keep government information secure. AES is intended to be a stronger, more efficient successor to Triple Data Encryption Standard ("3DES").

DES is a popular symmetric-key encryption method developed in 1975 and standardized by ANSI in 1981 as ANSI X.3.92, the contents of which are incorporated herein by reference. 3DES is the encrypt-decrypt-encrypt ("EDE") mode of the DES cipher algorithm 3DES is defined in the ANSI standard, ANSI X9.52-1998, the contents of which are incorporated herein by reference. DES modes of operation are used in conjunction with the NIST Federal Information Processing Standard ("FIPS") for data encryption (FIPS 46-3, October 1999), the contents of which are incorporated herein by reference.

The NIST approved a FIPS for the AES, FIPS-197. This standard specified "Rijndael" encryption as a FIPS-approved symmetric encryption algorithm that may be used by U.S. Government organizations (and others) to protect sensitive information. The NIST FIPS-197 standard (AES FIPS PUB 197, November 2001) is incorporated herein by reference.

The NIST approved a FIPS for U.S. Federal Government requirements for information technology products for sensitive but unclassified ("SBU") communications. The NIST FIPS Security Requirements for Cryptographic Modules (FIPS PUB 140-2, May 2001) is incorporated herein by reference.

RSA is a public key encryption system which can be used both for encrypting messages and making digital signatures. The letters RSA stand for the names of the inventors: Rivest, Shamir and Adleman. For more information on RSA, see U.S. Pat. No. 4,405,829, now expired, incorporated herein by reference.

"Hashing" is the transformation of a string of characters into a usually shorter fixed-length value or key that represents the original string. Hashing is used to index and retrieve items in a database because it is faster to find the item using the shorter hashed key than to find it using the original value. It is also used in many encryption algorithms.

Secure Hash Algorithm (SHA), is used for computing a secure condensed representation of a data message or a data file. When a message of any length<264 bits is input, the SHA-1 produces a 160-bit output called a "message digest." The message digest can then be input to other security techniques such as encryption, a Digital Signature Algorithm (DSA) and others which generates or verifies a security mechanism for the message. SHA-512 outputs a 512-bit message digest. The Secure Hash Standard, FIPS PUB 180-1, Apr. 17, 1995, is incorporated herein by reference.

Message Digest-5 (MD-5) takes as input a message of arbitrary length and produces as output a 128-bit "message digest" of the input. The MD5 algorithm is intended for digital signature applications, where a large file must be "compressed" in a secure manner before being encrypted with a private (secret) key under a public-key cryptosystem such as RSA. The IETF RFC-1321, entitled "The MD5 Message-Digest Algorithm" is incorporated here by reference.

Providing a way to check the integrity of information transmitted over or stored in an unreliable medium such as a wireless network is a prime necessity in the world of open computing and communications. Mechanisms that provide such integrity check based on a secret key are called "message authentication codes" (MAC). Typically, message authentication codes are used between two parties that share a secret key in order to validate information transmitted between these parties.

Keyed Hashing for Message Authentication Codes (HMAC), is a mechanism for message authentication using cryptographic hash functions. HMAC is used with any iterative cryptographic hash function, e.g., MD5, SHA-1, SHA-512, etc. in combination with a secret shared key. The cryptographic strength of HMAC depends on the properties of the underlying hash function. The IETF RFC-2101, entitled "HMAC: Keyed-Hashing for Message Authentication" is incorporated here by reference.

An Electronic Code Book (ECB) is a mode of operation for a "block cipher," with the characteristic that each possible block of plaintext has a defined corresponding cipher text value and vice versa. In other words, the same plaintext value will always result in the same cipher text value. Electronic Code Book is used when a volume of plaintext is separated into several blocks of data, each of which is then encrypted independently of other blocks. The Electronic Code Book has the ability to support a separate encryption key for each block type.

Diffie and Hellman (DH) describe several different group methods for two parties to agree upon a shared secret in such a way that the secret will be unavailable to eavesdroppers. This secret is then converted into various types of cryptographic keys. A large number of the variants of the DH method exist including ANSI X9.42. The IETF RFC-2631, entitled "Diffie-Hellman Key Agreement Method" is incorporated here by reference.

However, the present invention is not limited to the security or encryption techniques described and other security or encryption techniques can also be used.

IP is an addressing protocol designed to route traffic within a network or between networks. For more information on IP 54 see IETF RFC-791 incorporated herein by reference.

TCP provides a connection-oriented, end-to-end reliable protocol designed to fit into a layered hierarchy of protocols that support multi-network applications. For more information on TCP 58 see RFC-793, incorporated herein by reference.

UDP provides a connectionless mode of communications with datagrams in an interconnected set of networks. For more information on UDP see ITEF RFC-768 incorporated herein by reference.

The HyperText Transport Protocol (HTTP) Secure (HTTPs), is a standard for encrypted communications on the World Wide Web. HTTPs is actually just HTTP over a Secure Sockets Layer (SSL). For more information on HTTP, see IETF RFC-2616 incorporated herein by reference.

The SSL protocol is a protocol layer which may be placed between a reliable connection-oriented network layer protocol (e.g. TCP/IP) and the application protocol layer (e.g. HTTP). SSL provides for secure communication between a source and destination by allowing mutual authentication, the use of digital signatures for integrity, and encryption for privacy.

The SSL protocol is designed to support a range of choices for specific security methods used for cryptography, message digests, and digital signatures. The security method(s) are negotiated between the source and designation at the start of establishing a protocol session. The SSL 2.0 protocol specification, by Kipp E. B. Hickman, 1995 is incorporated herein by reference.

Transport Layer Security (TLS) provides communications privacy over the Internet. The protocol allows client/server applications to communicate over a transport layer (e.g., TCP) in a way that is designed to prevent eavesdropping, tampering, or message forgery. For more information on TLS see IETF RFC-2246, incorporated herein by reference.

The encrypted digital images are compressed and packaged 58 to reduce their size and speed up transmission over the communications network 24. For example, the encrypted digital images may be compressed and packaged using PKZIP, by Pkware, Inc. of Brown Deere, Wis., WINZIP, by Microsoft, Inc. of Redmond, Wash., or other types of data compression and data packaging methods known in the art.

The compressed encrypted digital images are securely transmitted 60 over the communications network 24 to the server computer 20a, 20b, 20c. For example, compressed encrypted digital images are securely transmitted via a Secure Sockets Layer ("SSL") (e.g., using an encryption key of 1000-bits or more to protect privacy of the digital images), using the File Transfer Protocol ("FTP").

A "secure transmission" over a communications network includes a transmission over a communications connection that is protected against unauthorized access, operation, or use, by means of encryption, or other forms of control or security.

However, other secure transmission techniques (e.g., RSA, DES, AES, data encryption, Internet Protocol Security ("IPsec"), etc.) and other data protocols (e.g., Transmission Control Protocol ("TCP")/Internet Protocol ("IP"), User Datagram Protocol ("UDP"), etc.) known in the art can also be used.

The server computers 20a, 20b, 20c securely receives the compressed encrypted digital images and un-compresses 62 encrypted digital images back to their original size. The server computer 20a, 20b, 20c decrypts 64 the un-compressed digital images to obtain the original digital images 54 scanned into the medical records processing system 10.

The original digital images 54 are processed 66 by the plural processing applications 26. For example, the medical template reader application 28 extracts patient encounter information from the original digital images 54 and creates a number of internal data structures used to verify and store the patent encounter information as is described below.

In one embodiment of the invention, if the medical template reader application 28 determines that it cannot accurately determine specific patient encounter information from the original digital images 54 (e.g., cannot electronically scan and process the s or other medical personnel's handwriting, marks on check boxes overlap, etc.), the patient encounter information in question is electronically highlighted on the original digital images 54 and displayed 68 in real-time by the medical data presentation application 32 for a human user to interpret and/or verify 70.

This real-time verification application 33 allows errors and/or inconsistencies in electronic interpretation of the data on the digital images 54 from the scanned paper templates 12 or original electronic data entered into an electronic template 12' to be immediately corrected by a human user. If the digital image is missing necessary, important, required or relevant data (e.g., provider signature, vital signs, patient demographics, etc.) this information may be returned to the provider so that the provider appropriately completes this data and the paper template is rescanned.

"Real-time" operations are those in which a computer's systems activities match a human perception of a time period or are computer system operations that proceed at rate similar to an external physical process. In another embodiment of the invention, near real-time or non-real-time processing can also be used. In one embodiment of the invention, real-time operations are conducted in a time-period of a few milli-seconds or faster in length.

In another embodiment of invention, if the medical template reader application 28 cannot properly determine patient encounter information from the original digital images 54, a determination as a "best guess" is made for the patient encounter information in question using one or more internal (e.g., software 33, hardware, firmware, etc.) digital image analysis techniques available to the medical template reader application 28. This embodiment does not necessarily rely on verification by a human user.

If the medical template reader application 28 has determined patient encounter information from the original digital images 54, and this has been verified and/or corrected by a human user the medical code processing engine 30 automatically generates the appropriate medical codes (e.g., E/M, CPT, HCPCS, etc.) in real-time for the patient encounter information using the internal data structures of stored patient encounter information. The generated medical codes along with the original digital images 54 including the patient encounter information, other patient encounter information extracted and other patient encounter information newly generated (e.g., a new electronic medical information record, an electronic invoice 75, etc.) are stored 72 in the database 22.

In one embodiment of the invention, the generated medical codes, generated tables of patient encounter information and the original digital images 54 are stored 72 in databases 22, wherein databases 22 are relational databases. The generated medical codes and the original digital images 50 are stored in an open database connectivity ("ODBC") format using structure query language ("SQL") commands to access the databases 22.

However, the invention is not limited to such an embodiment and other types of databases (e.g., non-relational), database formats and database commands can also be used with the databases 22.

ODBC is standard database access method developed by Microsoft Corporation. ODBC makes it possible to access any data from any application, regardless of which database management system ("DBMS") is handling the data. SQL is database sublanguage used in querying, updating, and managing relational databases.

The generated medical codes are also used by the medical code processing engine 30 to create an electronic invoice 75 or paper invoice 75 and a summary of the collected medical information for the patient in the form of an electronic medical record in real-time or sent to another data processing system for additional processing The electronic codes and electronic medical record is securely transmitted 74 (e.g., using SSL as described above) and is displayed 76 by the medical data presentation application 32 in real-time for medical office personal. Delayed processing may also be performed as appropriate to the specific situation (e.g., by another data processing system such as an external billing or invoicing system)

The electronic invoice 75 and electronic medical record can be displayed 76 in real-time via the medical data presentation application 32 on the client computers 16 (not illustrated), the server computers 20a, 20b, 20c (not illustrated), on another secure display 77 in the medical facility that collected medical information form the patient, or by any other authorized user on a computer (not illustrated) equipped for this display.

For example, if a patient entered a clinic and desired to pay by credit card or cash, immediately after being examined by a provider, the patient encounter information recorded on a paper medical information template 12 (e.g., FIG. 2) would be scanned in and processed as just described for FIG. 4. As the patient received his/her exit instructions (e.g., receiving instructions for prescribed medications, instructions to further threat an injury or illness at home, etc.) the medical codes generated in real-time are used to create an electronic invoice in real-time for the patient with an appropriate fee for the patient visit. Thus, the patient can be charged the appropriate fee immediately as he/she is ready to leave the clinic without delaying the patient any significant amount of time. This leads to greater overall patient satisfaction at a time when the patient is in pain or is not otherwise feeling well. This also leads to correct and immediate revenue for the medical facility and/or physician.

The electronic invoice and electronic medical record can also be securely transmitted 74 and displayed 76 at a later time (i.e., non real-time) for medical office personal for patients who are covered by insurance and for physicians who review the patient's chart at a later time.

Figure 5:
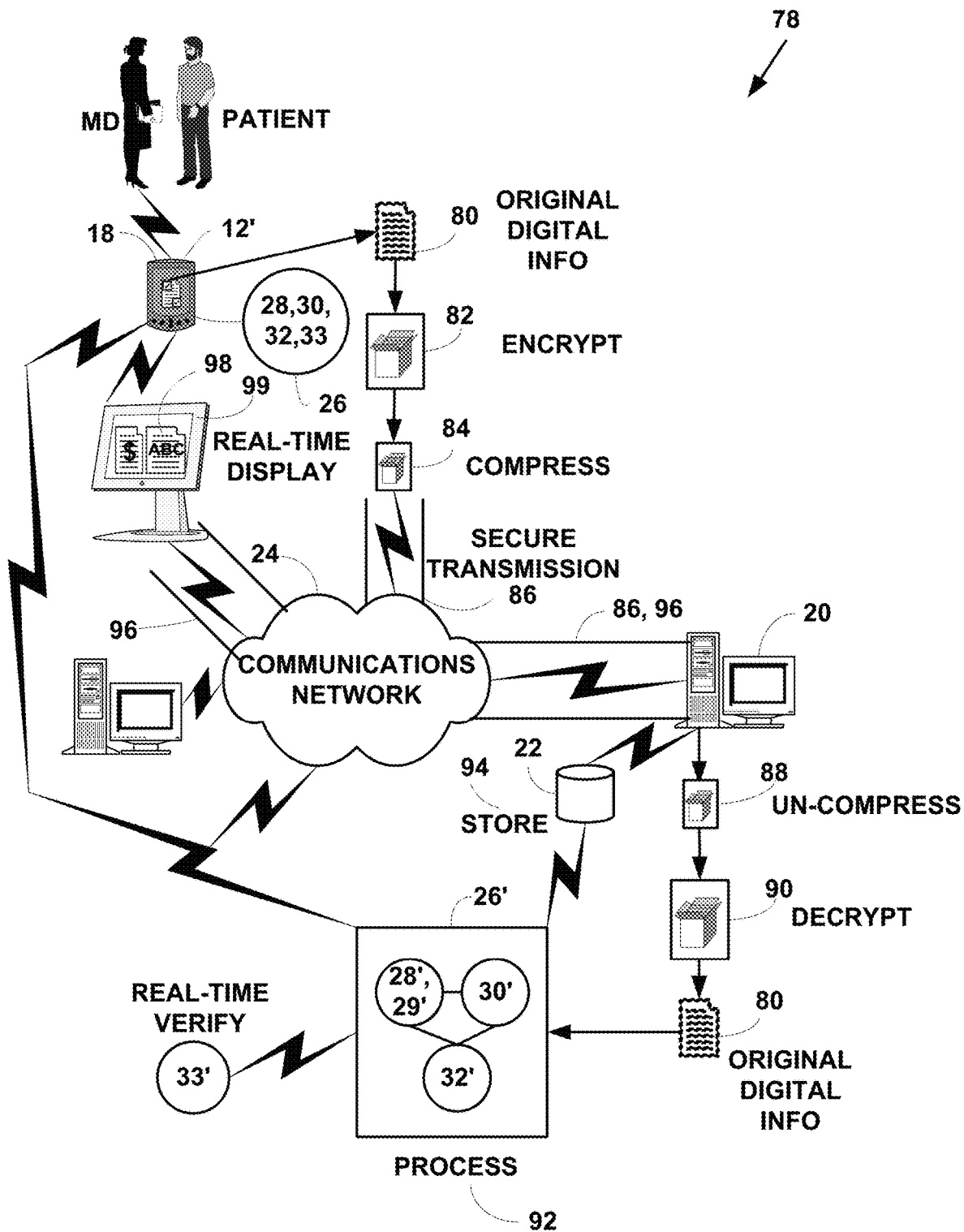
FIG. 5 is a block diagram illustrating an exemplary data flow for the medical records system of FIG. 1 for an electronic medical information template.

FIG. 5 is a block diagram illustrating an exemplary data flow 78 for the medical records system of FIG. 1 for an electronic medical information template 12'. Electronic medical information templates 12' are processed in a manner similar to the paper medical information templates 12 described above. In this embodiment, patient encounter information is not recorded on paper medical information templates. Instead, it is recorded electronically directly on the electronic medical information templates 12'.

In one embodiment, the electronic medical information template 12' is displayed on a computer screen or handheld network devices 18. Digital information 80 from the electronic medical information template 12' is collected and encrypted 82 on the electronic device to ensure the data is protected and kept private.

The encrypted digital information is compressed 84 on the network devices 18 to reduce its size and speed up transmission over the communications network 24. The compressed encrypted digital information is securely transmitted 86 from the network devices 18 over the communications network 24 to one or more of the server computers 20a, 20b, 20c.

The one or more server computers 20a, 20b, 20c securely receives the compressed encrypted digital information and un-compresses 88 encrypted digital information back to its original size. One or more of the server computers 20a, 20b, 20c decrypts 90 the un-compressed digital information to obtain the original digital information 80 collected electronically from the network devices 18.

The original digital information 80 is processed 92 by the processing applications 26. The medical template reader application 28 extracts patient encounter information from the original digital information 80 and creates a number of internal data structures used to store the patent information.

In this data flow, the verification steps described above for the paper electronic information templates 12' are typically not necessary because there are no digital images to process, only original digital information 80 generated directly from the electronic medical information template. However, automated internal or human verification may also be performed. In addition, the verification application 33 may be used to check and verify either all information input into the electronic medical information templates 12' or selected ones of the input information.

For example, if the medical information entered into the medical information template 12' was for a male patient, and questions about pregnancy or menstrual periods were included in the information collected, the verification application 33 would automatically flag such inconsistencies for review. The verification application 33 is also used to flag inconsistencies between chief complaints and known interactions between one or more medications that the patient may be currently taking and/or new medications prescribed for the current patient encounter.

The medical code processing engine 30 automatically generates the appropriate medical codes (e.g., E/M, CPT, HCPCS, etc.) for the patient encounter information using the tables of patient encounter information. The generated medical codes are stored 94 along with the original digital information 80 including the patient encounter information in the database 22.

The generated medical codes are used by the medical code processing engine 30 to create an electronic invoice (Table 7) and an electronic medical record (FIG. 22) for the patient. The electronic invoice and electronic medical record is securely transmitted 96 (e.g., using SSL as described above) and is displayed 98 by the medical data presentation application 32 in real-time for medical office personal.

The electronic invoice (Table 7) and electronic medical record (FIG. 22) are displayed 98 in real-time via the medical data presentation application 32 on the client network device 18, the server computers 20a, 20b, 20c (not illustrated), on another secure display 99 in the medical facility that collected medical information form the patient via the medical data presentation application 32 or on the client network devices 18 from which the patient encounter information was collected (not illustrated).

The electronic invoice (Table 7) and electronic medical record (FIG. 22) can also be securely transmitted 96 and displayed 98 at a later time (i.e., in non real-time) for medical office personal for patients who are covered by insurance and for physicians who review the patient's chart at a later time. Billing codes can also be electronically downloaded to other software applications for further processing, storage or transmission to other entities or other data processing systems.

In another embodiment, all the processing just described for the dataflow in FIG. 5 is completed on the client network devices 18 (e.g., Method 184, etc.). In such an embodiment, the client network devices 18 periodically are in secure communications with one or more of the server computers 20*a*, 20*b*, 20*c* at a later time via the communications network 24 to securely transmit a copy of all information collected and created for the patient encounter. In such an embodiment, the client network device 18 securely transmits the original and processed data to a display device in the medical facility for real-time display 99. The real-time display includes the electronic medical record (FIG. 22) as well as the electronic invoice (Table 7).

Processing Medical Information Templates

Figure 6:
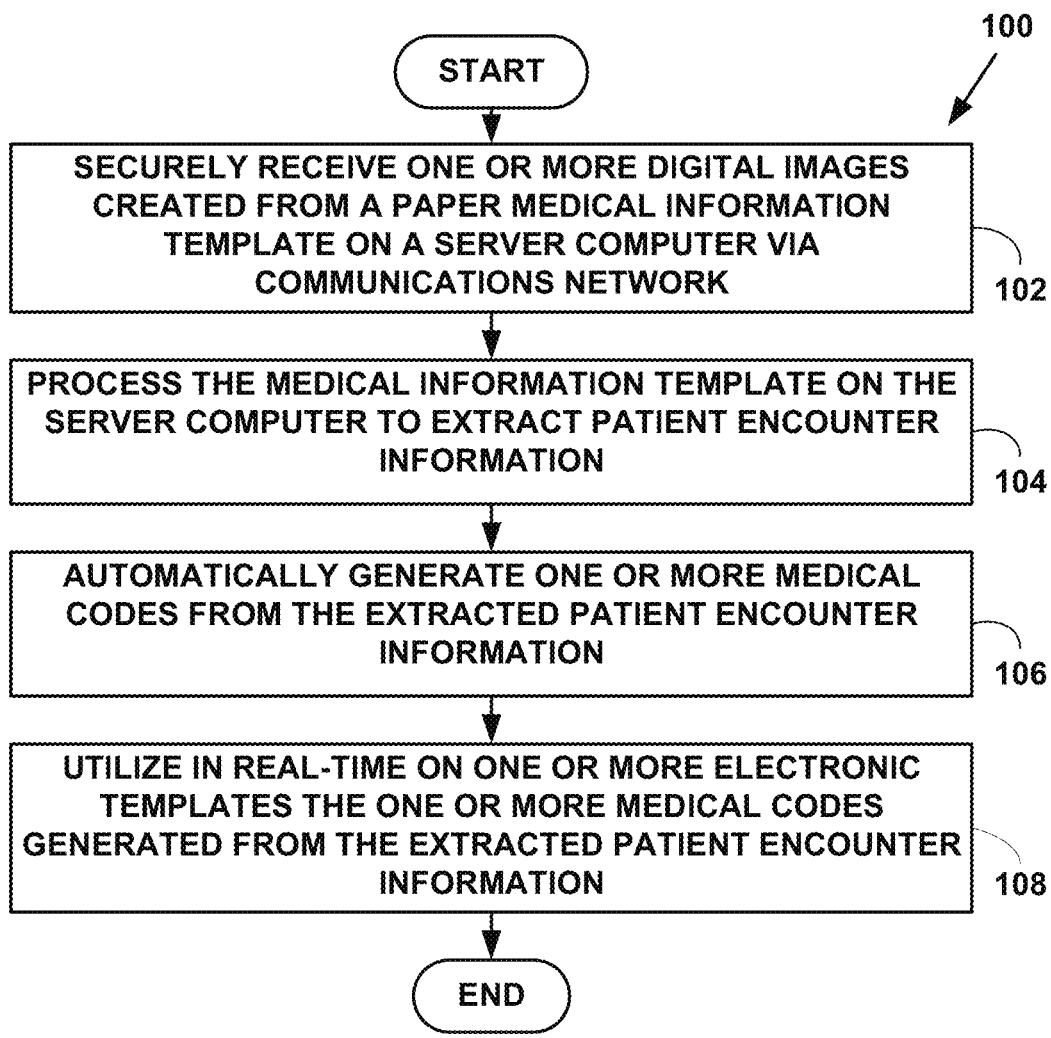
FIG. 6 is a flow diagram illustrating a method of processing medical information templates via the medical records system.

FIG. 6 is a flow diagram illustrating a Method 100 of processing medical information templates via the medical records system 10. At Step 102, one or more digital images created from a paper medical information template 12 are securely received on a server computer 20*a*, 20*b*, 20*c* via a communications network 24. The digital images of the medical information template were created by scanning a paper copy of the medical information template 12 into the medical records system 10 via the scanner 14. At Step 104, the one or more digital images are automatically processed on the server computer 20*a*, 20*b*, 20*c* to extract patient encounter information. At Step 106, one or more medical codes are automatically generated from the extracted patient encounter information. The one or more medical codes generated include, but are not limited to, one or more of E/M, CPT, HCPCS, ICD-9, ICD-10, SNOWMED CT, and/or other types of codes. At Step 108, the one or more generated medical codes are generated from the extracted patient encounter information are utilized on one or more electronic templates. The one or more electronic templates are displayed on a graphical user interface (GUI) or the one or more electronic templates are used to produce additional medical information documents.

The one or more electronic templates can be displayed on a GUI in real-time directly after a patient encounter providing immediate access to the one or more electronic medical information templates created from the one or more generated medical codes.

The one or more generated medical codes can also be utilized via the one or more electronic templates to produce additional medical information documents, such as invoices, medical records, etc. The additional medical information documents can be produced via exemplary medical records system 10 or be sent to other data processing systems (not illustrated) for further processing. For example, the one or more electronic templates including the one or more generated medical codes (e.g., as XML or other types of electronic templates) can be sent electronically to another data processing system, such as a 3rd party or external medical billing system, that creates and sends an invoice to the patient after the patient encounter.

In such an embodiment, the one or more electronic templates may never be viewed or displayed, but treated as data that is processed automatically by other data processing systems. In such an embodiment, Method 100 is used to create electronic data that is used as an interface to other data processing systems.

The one or more electronic templates include, but are not limited to, an electronic invoice template, an electronic medical record template, a current compliant template, a patient tracking template, a nurse template, a review template, a diagnosis template; a provider template; a referral template and other types of electronic templates.

Chief Complaint Determines Selection of Specific History Template(s):

The chief complaint template describes an organization of an electronic medical record in such a way that medical information provided by personnel (including but not limited to the provider, nursing staff or even the patient himself or herself), can be documented using other electronic templates (e.g., a history template) or another paper template. For example, when a provider/or patient selects chief complaint, an additional electronic template (e.g., a history template) specific to that complaint is generated based on the chief complaint of the patient. This additional electronic template (specific to a given chief complaint) includes information that a medical provider generally documents or could generally be expected to document for a given chief complaint. This information may include, but is not limited to appropriate history of present illness ("HPI"), review of systems ("ROS"), past medical family social history ("PMSFH"), allergies, medications, vital signs, etc. This information may or may not be modified by or for the medical facility that collected the patient encounter information (e.g., via a review template).

Diagnosis determines selection of specific physical exam, treatment and disposition template(s): In addition, the organization of an electronic medical record can be presented in such a way that a paper or an electronic template for a health-care provider for the majority of patients can be documented using another single electronic template (e.g., provider template). When a provider selects a diagnosis for a given patient, a specific electronic template is generated based on that diagnosis of patient (e.g., a diagnosis template). This specific electronic template (i.e., specific to the given diagnosis) includes information that the provider generally documents or could be expected to document for a given diagnosis. This information may include but not be limited to physical exam, treatments (including but not limited to medications, clinical procedures, dressings, splints, casts, crutches, changes in activity, or any other treatment), laboratory testing, diagnostic testing, referrals, consults, disposition, or any other items deemed relevant for the provider's documentation of this chart. A default set of the above data may or may not be set in advance, but can be modified by the provider. This information may or may not be modified by or for the medical facility that collected the patient encounter information (e.g., via a physician review template).

Method 100 may also further comprise generating an electronic invoice in real-time using the one or more medical codes calculated from the extracted patient encounter information. The electronic invoice includes a fee for the medical services provided during the patient encounter. The electronic invoice is presented in real-time via a graphical user interface ("GUI") (not illustrated in FIG. 6) or utilized in real-time via other data processing systems as was described above Method 100 may also further comprise generating an electronic medical record in real-time using the one or more medical codes calculated from the extracted patient encounter information and other information extracted from the patient encounter information. The electronic medical record is presented in real-time via a graphical user interface ("GUI") (not illustrated in FIG. 6) or utilized in real-time via other data processing systems as was described above.

The patient encounter information is extracted by processing the plural check-boxes or other electronically interpreted data and is stored in internal data structures with plural fields on the server computer 20a, 20b, 20c. After Step 104, the internal data structure fields include an indication of which check-boxes and data fields were used (i.e., checked or filled out), and portions of the digital images corresponding to the original paper medical information template 12 may be placed into defined locations on a newly generated electronic invoice template, electronic medical record template, or other electronic template (e.g., nurse, insurance, etc.). The internal data structure fields also include links to the original digital images 54.

These internal data structure fields are also be used for (but are not limited to): (1) storing transcription of handwritten data (using handwriting recognition software, firmware or hardware) to replace the graphic image of handwritten data with transcribed text in the electronic medical record; (2) storing handwritten diagrams that are placed into an electronic template of an electronic medical record; (3) storing computerized text including generated medical codes, computerized text generated from check boxes and other information extracted from the patient encounter information that is displayed at various locations in one or more electronic templates such as the electronic invoice electronic medical record, etc.; (4) storing transcriptions of audio dictation data with transcribed text included in the electronic medical record via audio dictation interface 27.

For example, when the paper medical information template 12 is used to document a patient encounter, a provider can mark the encounter as needing dictation. The electronic medical record created is marked with a status of "dictation pending." The electronic medical record generated is pre-populated for the pending dictation text including information from the patient encounter. When the provider has time, he/she securely logs into the audio dictation interface 27 (e.g., via a secure web-site) on the medical records system 10 views a queue of patient charts awaiting dictation. A dictation voice file is captured from the provider via the dictation interface and is directly associated with the electronic medical record. In on embodiment, a medical transcriptionist later securely logs onto the same dictation interface, listens to the dictation file and generates an electronic transcript from the dictation. The medical record is populated with electronic information from the electronic transcript. Thus, the electronic medical records can also be dynamically populated with provider dictation text based on the result of the patient encounter. In another embodiment, voice recognition software is used to automatically transcribe the dictation into electronic text.

One set of patient encounter information extracted from the one or more digital images of the paper medical information template 12 at Step 104 (and Step 114 described below) includes extracting historical information ("HX") obtained from the patient encounter and populating internal data structures. In one embodiment of the invention, extracted historical information is compared against predetermined values for an HX matrix (described below) for determining a historical value used to calculate a medical code. However, the invention is not limited to this embodiment and the extracted historical information can be used with other internal data structures to generate a medical code. In one embodiment, the HX matrix data structure is stored as data bits in a computer readable medium on the client network device 18.

The HX information includes, but is not limited to, predefined elements that make up chief complaint ("CC") information, history of present illness ("HPI") information, past medical, family, social history information ("PFMSH") and review of system ("ROS") information.

Table 1b illustrates exemplary HX information collected. However, the present invention is not limited to this HX information, more, less and other types of HX information can also be collected from the patient encounter information.

TABLE 1b

| HX Information |
|---|
| Chief Complaint (CC): |
| Description of one or more problems (e.g., sore throat, chest pains, trouble breathing, etc.) |
| History of Present Illness (HPI): |
| Location; quality; severity; duration; timing; context; modifying factors; associated signs and symptoms. |
| Past medical, family, social history (PFMSH): |
| Medical History - the patient's past experiences with illnesses, operations, injuries and treatments. Family History - a review of medical events in the patient's family, including diseases which may be hereditary or place the patient at risk. Social History - an age appropriate review of past and current activities. |
| Review of Systems (ROS): |
| Constitutional; eyes, ears, nose, mouth, throat; cardio-vascular; respiratory; GI; GU; muscular; neurological; psychological; immune; etc. |

Another set of patient encounter information extracted from the digital images of the paper medical information at Step 104 and 114 includes extracting physical examination information ("PX") obtained from the patient encounter and populating internal data structures. In one embodiment of the invention, extracted physical examination information is compared against predetermined values for a PX matrix (described below) for determining a physical examination value used to calculate a medical code. However, the invention is not limited to this embodiment and the extracted physical examination information can be used with other internal data structures generate a medical code. In one embodiment, the PX matrix data structure is stored as data bits in a computer readable medium on the client network device 18.

Table 2 illustrates where body areas and organ systems from which PX information is collected. However, the present invention is not limited to this PX information, more, less and other types of PX information can also be collected from the patient encounter information.

TABLE 2

PX Areas

Body Areas:

Head, including face; Back including spine; Chest including breasts; Genitalia including groin and buttocks; Abdomen; Neck; Extremities; etc.

Organ Systems:

Constitutional; eyes, ears, nose, mouth, throat; cardio-vascular; respiratory; GI; GU; muscular; neurological; psychological; immune; etc.

Figure 17:
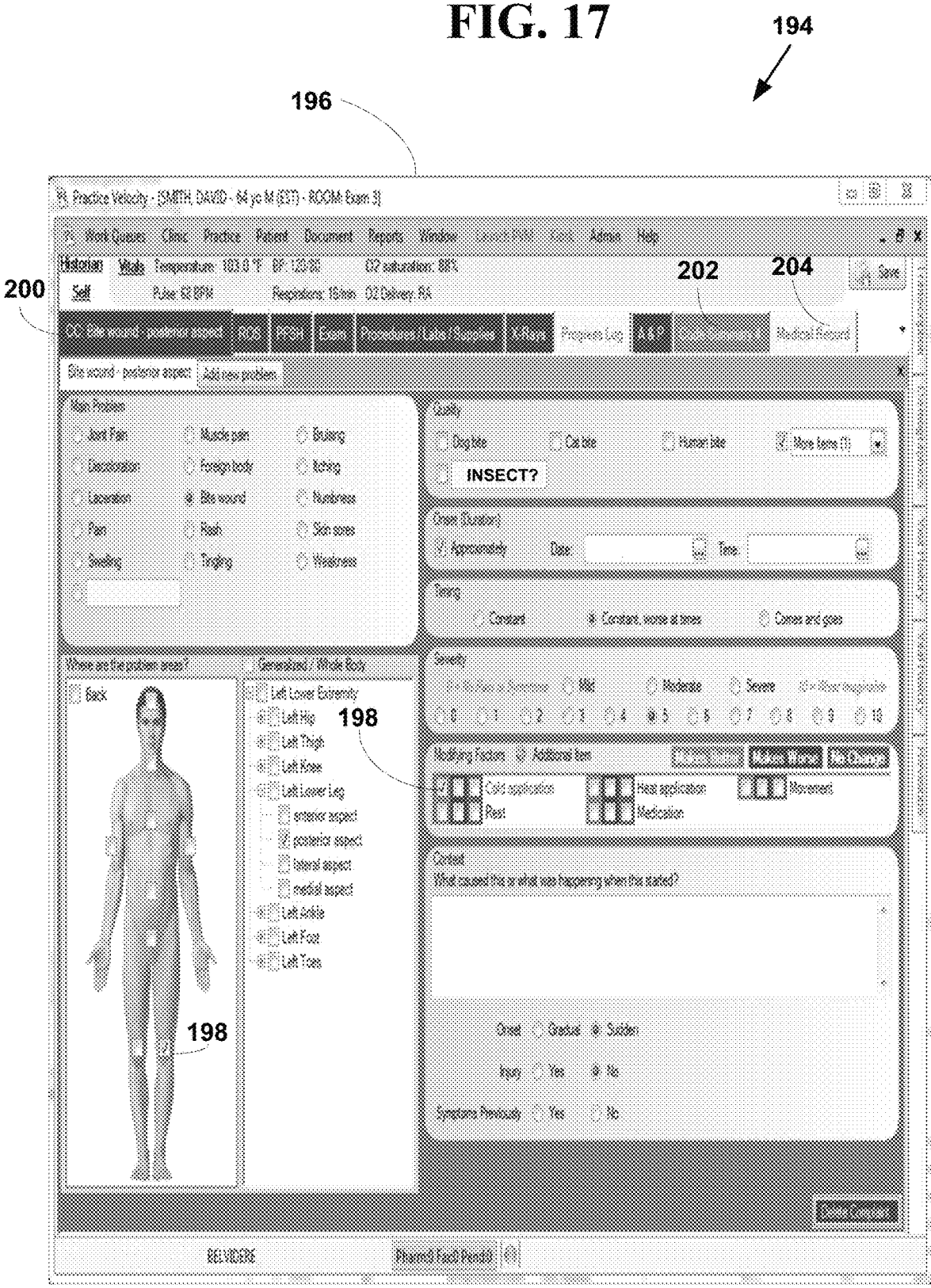

In one embodiment, the body areas and organ systems are displayed in 3D on the various medical templates (e.g., item 196, FIG. 17, etc.)

Table 3 illustrates possible levels of the physical exam types of PX information determined. This example uses one specific set of guidelines commonly referred to and published by the Centers for Medicare & Medicaid Services ("CMS") as the 1997 Documentation Guidelines for Evaluation and Management Services, but can utilize other methods or guidelines as determined by the type of exam or by changes in prescribed or allowable guidelines. In addition, the PX information is exemplary only, and the present invention is not limited to such PX information.

The PX information is determined in part from processing the check-boxes completed in the medical diagnosis box 41 illustrated in FIG. 2B on the paper medical information template 12 and in FIG. 3.

TABLE 3

PX Types

| | |
|---|---|
| PF | One to five elements identified by a bullet (e.g., one to five body areas or organs) |
| EXPF | At least six elements identified by a bullet (e.g., up to a total of six organ systems) |
| DET | At least twelve items identified by a bullet from 2 (or more) PX areas |
| COMP | Two or more elements identified by a bullet in nine or more organ systems. |

The PX types include, but are not limited to: a problem focused ("PF") exam that includes 1-5 specific exam elements identified by a bullet on the paper medical information template 12; an expanded problem focused exam ("EXPF") that includes at least 6 specific exam elements; identified by a bullet, Detailed exam ("DET") that includes at least 12 elements in two or more areas/systems, identified by a bullet; and a comprehensive exam ("COMP") that includes documentation of at least two elements from each of nine areas/systems identified by a bullet.

Another set of patient encounter information extracted from the digital image of the paper medical information at Steps 104 and 114 includes extracting complexity of medical decision making information ("CX") obtained from the patient encounter and populating internal data structures. In one embodiment of the invention, extracted complexity information is compared against predetermined values for a CX matrix (described below) for determining a complexity value used to calculate a medical code. In one embodiment, the CX matrix data structure is stored as data bits in a computer readable medium on the client network device 18. However, the invention is not limited to this embodiment and the extracted complexity information can be used with other internal data structures generate a medical code. The CX information includes a number of diagnosis ("DX") or treatment options and risk ("RISK") information.

Table 3a illustrates exemplary CX information (e.g., FIG. 10). However, the present invention is not limited to this embodiment and other embodiments can also be used to practice the invention.

TABLE 3a

CX Types

| DX | RISK |
|---|---|
| straight forward ("SF") number of diagnosis, <= one (code 1). | straight forward risk ("SF"), includes a self-limited or minor problem (code 1). |
| low number of diagnoses ("LOW"), minimal (code 2). | low risk ("LOW"), includes two or more minor problems, one stable chronic illness or an acute uncomplicated illness or injury (code 2). |
| moderate number of diagnoses ("MOD"), multiple (code 3). | moderate ("MOD") includes one or more chronic illnesses with mild exacerbation, progression, or side effect treatment, two or more stable chronic illnesses, an undiagnosed new problem with uncertain prognosis or an acute illness with systemic symptoms or an acute complicated injury (code 3). |
| high number of possible diagnoses ("HIGH"), extensive (code 4). | high risk ("HIGH"), includes one or more chronic illnesses with severe exacerbation, progression or side effects of treatment, or acute or chronic illnesses or injuries that may pose a threat to life or bodily function or an abrupt change in neurological status (code 4). |

The DX information includes, but is not limited to: straight forward ("SF") diagnosis; a low number of diagnoses ("LOW"); a moderate number of diagnoses ("MOD"); and a high number of possible diagnoses ("HIGH"). This DX scoring can be performed using an objective scoring system. A unique aspect of this invention includes (but is not limited to) presentation of these choices in check-box form with each of a maximum number of choices in each category represented by a check-box. Scoring of the DX section can then be performed by adding a point value of each box to obtain the total score in the DX section. Although, scoring of the DX section is not limited to this method, if it is used the following scores correlate with the various levels of DX: (≤1) minimal; (2) limited; (3) multiple; or (4) extensive.

The RISK information includes: minimal or straight forward ("SF") risk in which the medical problem is self-limited or a minor problem (e.g., cold, insect bite, etc.); low risk ("LOW") in which the medical problem includes two or more minor problems, one stable chronic illness (e.g., well controlled hypertension or non-insulin dependent diabetes, cataract, etc.) or an acute uncomplicated illness or injury (allergic reaction, simple sprain); moderate risk ("MOD") in which the medical problem includes one or more chronic illnesses with mild exacerbation, progression, or side effect treatment, two or more stable chronic illnesses, an undiagnosed new problem with uncertain prognosis (e.g., lump in breast or prostrate, etc.) an acute illness with systemic symptoms (e.g., pneumonitis, colitis, etc.) or an acute complicated injury (e.g., head injury with brief loss of consciousness); and high risk ("HIGH") in which the medical problem includes one or more chronic illnesses with severe exacerbation, progression or side effects of treatment, or acute or chronic illnesses or injuries that may pose a threat to life or bodily function (e.g., multiple trauma, acute MI, pulmonary embolus, severe respiratory distress, progressive severe rheumatoid arthritis, psychiatric illness with potential threat to self or others, acute renal failure, etc.) or an abrupt change in neurological status (e.g., seizure, TIA, weakness or sensory loss, etc.).

In one embodiment of the invention, omission of analysis of an amount and/or complexity of data reviewed is completed Omission of this aspect of a CX matrix can alter a CX score of very few patient encounters, if the previously used scoring for DX and RISK are utilized. Scoring of an amount and/or complexity of data reviewed may be added to the medical records processing system 10 if indicated by physician utilization, patient population, or changes in coding guidelines.

Another set of patient encounter information extracted from the digital image of the paper medical information at Steps 104 and 114 includes extracting patient status information and patient demographic information. The patient status information includes, but is not limited to, new patient, existing patient, consult, pre-surgery, hospital, etc. The patient demographic information, includes, but is not limited to, patient date-of-birth, etc.

The patient status information and patient demographic information is used in certain situations to override or modify the one or more medical code automatically generated at Steps 106 (and Step 118 described below) and/or to generate additional medical codes. For example, the patient status information, such as admit to the hospital can automatically override or generate addition types of medical codes. As another example, the patient demographic information such as date-of-birth within a certain pre-determined range (e.g. very young or very old) can automatically override or generates other types of medical codes.

Another set of patient encounter information extracted from the digital image of the paper medical information at Steps 104 and 114 includes extracting medical diagnosis information for the problems described during the patient encounter.

Another set of patient encounter information extracted from the digital image of the paper medical information at Steps 104 and 114 includes extracting clinical procedure information, treatment information and supply information. The clinical procedure information, includes, but is not limited to, clinical or hospital or surgical procedure information, such as stitches, applying cast, a desired operation, diagnostic tests (e.g., x-rays, MRI scans, CRT scans, etc.) and other types of clinical procedure information. The treatment information, includes, but is not limited to, medications, physical therapy, etc. The supply information includes, but is not limited to, types of medical supplies used on the patient such as bandages, casts, crutches, etc.

However, the present invention is not limited to extracting the patient encounter information described and other types of patient encounter information can also be extracted.

One type of medical codes automatically generated at Step 106 (and Step 118 described below) includes CPT E/M codes for new outpatient visits. Table 4 illustrates a few exemplary such medical codes and their corresponding requirements. The codes in Table 4 illustrate only a selected few of the many AMA CPT E/M codes and the present invention is not limited to generating these exemplary medical codes. An amount of provider time spent on the patient encounter is also determined.

TABLE 4

| New Outpatient: CPT Code 99201 |
|---|
| HX: EXPF<br>PX: EXPF<br>CX: SF<br>Provider Time: 10 minutes |
| New Outpatient: CPT Code 99202 |
| HX: EXPF<br>PX: EXPF<br>CX: SF<br>Provider Time: 20 minutes |
| New Outpatient: CPT Code 99203 |
| HX: DET<br>PX: DET<br>CX: LOW<br>Provider Time: 30 minutes |
| New Outpatient: CPT Code 99204 |
| HX: COMP<br>PX: COMP<br>CX: MOD<br>Provider Time: 45 minutes |
| New Outpatient: CPT Code 99205 |
| HX: COMP<br>PX: COMP<br>CX: HIGH<br>Provider Time: 60 minutes |

Another type of medical code generated at Step 106 and 118 includes AMA CPT codes for established outpatient visits. Table 5 illustrates such exemplary codes and their corresponding requirements. The codes in Table 5 illustrate only a selected few of the many CPT E/M codes and the present invention is not limited to generating these exemplary medical codes. The present invention is not limited to the CPT E/M codes illustrated and the present invention implements all and/or selected ones of the possible CPT E/M.

TABLE 5

| Established Outpatient: CPT Code 99212 |
|---|
| HX: PF<br>PX: PF<br>CX: SF<br>Provider Time: 10 minutes |
| Established Outpatient: CPT Code 99213 |
| HX: EXPF<br>PX: EXPF<br>CX: LOW<br>Provider Time: 15 minutes |
| Established Outpatient: CPT Code 99214 |
| HX: DET<br>PX: DET<br>CX: MOD<br>Provider Time: 25 minutes |
| Established Outpatient: CPT Code 99215 |
| HX: COMP<br>PX: COMP<br>CX: HIGH<br>Provider Time: 40 minutes |

According to current AMA CPT guidelines, time is only to be used to determine the level of E/M code if greater than 50% of the face-to-face time of the encounter involved counseling or coordination of care. If applicable coding guidelines are revised at some future date, then time may be factored as indicated by these changes.

Step 106 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

Figure 7:
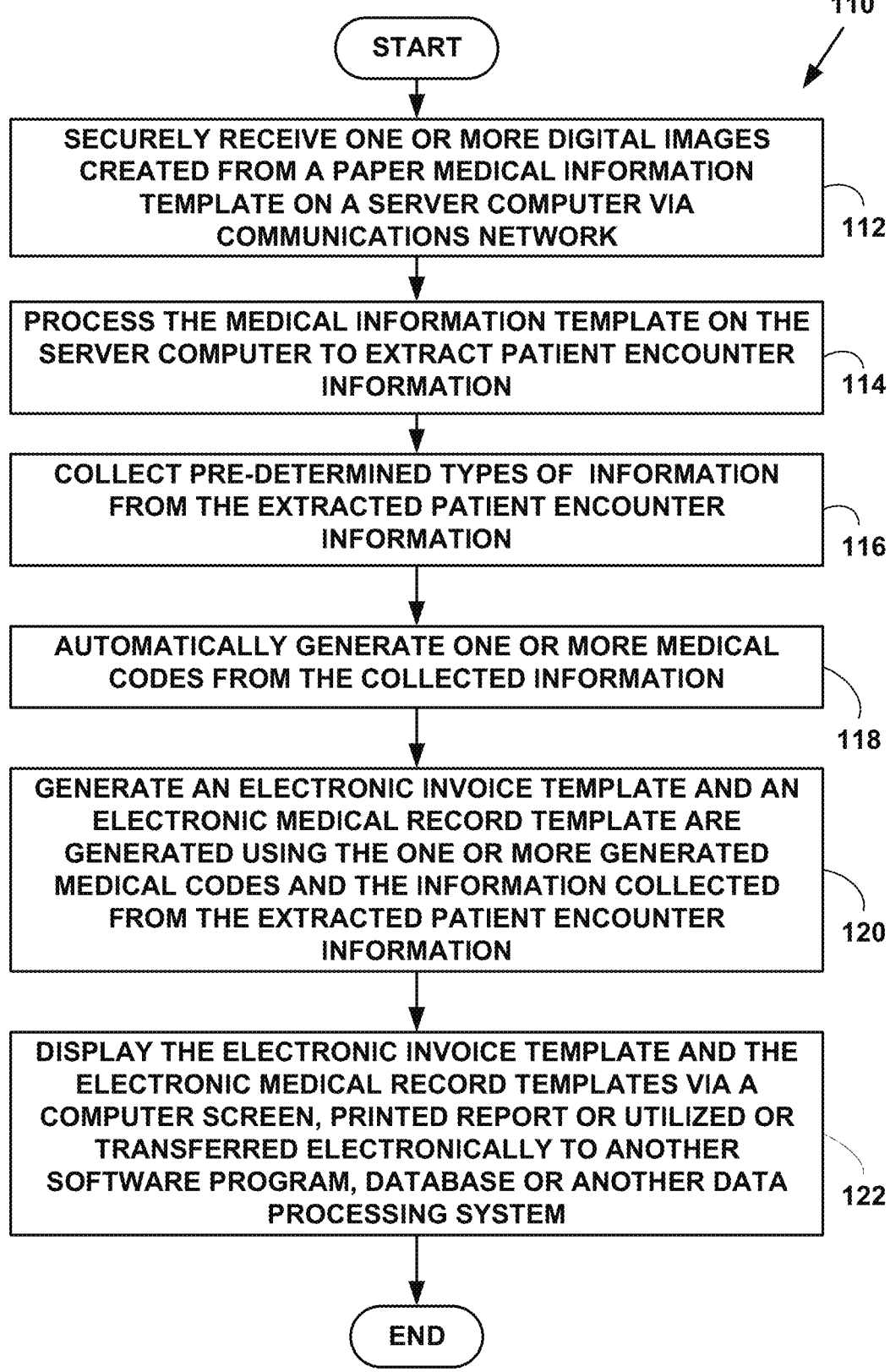
FIG. 7 is flow diagram illustrating a method of processing medical information templates via the medical records system.

FIG. 7 is a Method 110 for automatically calculating a medical code from patient encounter. At Step 112, one or more digital images created from a paper medical information template 12 are securely received on a server computer 20a, 20b, 20c via a communications network 24. The digital images of the medical information template were created by scanning a paper copy of the medical information template 12 into the medical records system 10 via the scanner 14. At Step 114, the one or more digital images are automatically processed on the server computer 20a, 20b, 20c to extract patient encounter information. At Step 116, historical information, physical examination information, complexity information, diagnosis, clinical procedures, tests, supplies and other data are collected from the extracted patient encounter information. At Step 118, one or more medical codes are automatically generated from the information collected from the extracted patient encounter information. The one or more medical codes generated include, but are not limited to, one or more of E/M, CPT, HCPCS, ICD-9 ICD-10, or other medical codes. At Step 120, an electronic invoice template and an electronic medical record template are automatically generated in real-time using the one or more generated medical codes collected from the extracted patient encounter information. At Step 122, the electronic invoice template and the electronic medical record templates are displayed in real-time via a computer screen, printed report or utilized or transferred electronically to another software program, database or another data processing system.

Step 118 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

FIG. 8 is a block diagram illustrating an exemplary HX matrix 124. The HX matrix 124 is used to determine a history value from the historical information extracted from the patient encounter and used is to generate the medical codes. The HX matrix includes fields for the CC, HPI, PFMSH and ROS elements as described above.

FIG. 9 is a block diagram illustrating an exemplary PX matrix 126. The PX matrix 126 is used to determine a physical examination value from the physical examination extracted from the patient encounter and is used to generate the medical codes. The PX matrix includes fields for the PF, EXPF, DET and COMP elements as described above and a count of the check-boxes extracted as described in Table 3 above.

FIG. 10 is a block diagram illustrating an exemplary CX matrix 128. The CX matrix 128 is used to determine a complexity value from the complexity information extracted from the patient encounter and is used to generate the medical codes. The CX matrix includes fields for DX and RISK and the SF, LOW, MOD and HIGH elements as described above.

Figure 11:

FIG. 11 is a block diagram illustrating an exemplary final E/M matrix 130 for a new outpatient. In one embodiment, the E/M matrix 130 is stored as data bits in a computer readable medium on the client network device 18. The final E/M matrix 130 is used to calculate a medical code with the historical value, the physical examination value and the complexity value determined from the HX 124, the PX 126 and the CX 128 matrices. The final E/M matrix 130 includes possible values determined from the HX, PX and CX matrices. It also includes a set of medical codes that can be calculated. FIG. 11 illustrates a set of CPT E/M codes, only for 99201 through 99205 as illustrated in Table 4. FIG. 11 is exemplary only and the invention is not limited to this E/M matrix. The invention includes other plural matrices to generate other types of medical codes.

Figure 12:
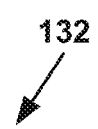

FIG. 12 is a block diagram illustrating an exemplary final E/M matrix 132 for an established outpatient. The final E/M matrix 132 also includes values determined from the HX, PX and CX matrices. It also includes a set of medical codes that can be calculated. FIG. 12 illustrates a set of CPT E/M codes, only for 99212 through 99215 as illustrated in Table 5. In this example, only two of the three aspects of the HX, PX, and CX need meet the level for the final code. FIG. 12 is exemplary only and the invention is not limited to this E/M matrix. The invention includes plural other matrices to generate other types of medical codes.

Method 110 is illustrated with an exemplary simple patient encounter. An 18-year female patient arrives at a family practice office as a new patient complaining of an acute bee sting on her right fifth finger. She indicates that she has no chronic medical problems, is using no medications and is not known to have a severe allergy to bee stings. She has only minor swelling and no other symptoms. The provider records the patient history on paper medical information template 34, and the provider checks a only small number of check-boxes for the physical exam, template 40 and a minor, new problem in box 41 of FIG. 2B. The patient encounter information is processed with Steps 112, 114 and 116 of Method 110.

At Step 116, referring to FIG. 8, a history value is determined from the HX matrix 124 using the historical information collected from the patient encounter and stored in the internal data structures. Since the chief complaint ("CC") is a bee sting, the history of the present illness ("HPI") is brief, the medical history is collected (i.e., not allergic to bee strings, no chronic medical problems, on no medications, etc.) and the review of systems ("ROS") is limited to constitutional and respiratory systems, the history value returned from the HX matrix is EXPF for a "extended problem focused" complaint.

At Step 116, referring to FIG. 9, a physical examination value is determined from the PX matrix 126 using the physical examination information collected from the patient encounter. The physical exam could be a PF value.

At Step 116, Referring to FIG. 10, a complexity value is determined from the CX matrix 128 using the complexity information collected from the patient encounter. Since a local bee sting reaction is a minor, self-limited problem, DX value is one. The patient may be given over-the-counter medications so the RISK score is two. This makes the complexity value ("CX") a straight forward, or SF value.

At Step 118, referring to FIG. 11, a medical code is generating from the final E/M matrix 130 for a new outpatient using the history value of EXPF from the HX matrix 124, the physical examination value of PF from the PX matrix 126, and the complexity value of SF from the CX matrix 128. The exemplary medical code and billing code generated is 99201.

Method 110 is illustrated with a second more complex exemplary patient encounter. A 58-year male established patient arrives at a family practice physician office complaining of acute onset of one hour of 10/10 chest pain, accompanied by shortness of breath. The patient suffers from chronic diabetes, has had his left leg amputated and has advanced heart disease, lung disease and kidney disease. There is a history of diabetes in his family and he is currently a heavy smoker of cigarettes. The provider records the patient encounter on paper medical information template 30 for which the provider checks a large number of check boxes and fills in a large number of blanks for the patient encounter including multiple check-boxes in box 41 of FIG. 2B.

At Step 116, referring to again FIG. 8, a history value is determined from the HX matrix 124 using the historical information collected from the patient encounter. Since the chief complaint ("CC") is pain; the history of the present illness ("HPI") is extended including four or more elements (location, chest; associated symptoms, shortness of breath; duration, one hour; severity 10/10); the past family, medical and social history is relevant and includes elements of both the medical and social history. (e.g., leg amputation, pain in fingers and kidney disease related to diabetes, heart and lung disease related to heavy smoking, older male) and the review of systems ("ROS") includes multiple (≥10) systems (e.g., constitutional, neurological, cardio-vascular, respiratory, etc.), the history value returned from the HX matrix is COMP for a comprehensive history.

At Step 116, referring again to FIG. 9, a physical examination value is determined from the PX matrix 126 using the physical examination information collected from the patient encounter. All elements identified by a bullet in over 9 areas/systems are documented in FIG. 2B so a COMP value (comprehensive exam) is generated.

At Step 116, referring again to FIG. 10, a complexity of medical decision making value is determined from the CX matrix 128 using the complexity information collected from the patient encounter. Since the problems are new and additional workup is planned, the detailed exam ("DX") value is four. Since the risk of morbidity or mortality is high based on the life-threatening nature of the patient's presentation, chief complaint the RISK value is also four. This makes the complexity of medical decision making value a HIGH value.

At Step 118, referring to FIG. 12, a medical code is generated from the final E/M matrix 132 for an established outpatient using the history value of COMP from the HX matrix 124, the physical examination value of COMP from the PX matrix 126, and the complexity of medical decision making value of HIGH from the CX matrix 128. The medical code generated is 99215. (See also Table 5).

Figure 2D:
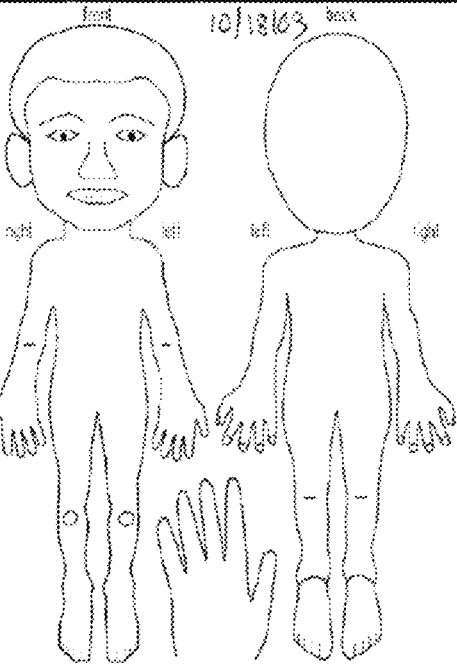

FIGS. 2C and 2D are a block diagram 133 illustrating a front side 135 and a back side 137 of another exemplary paper medical information form that further illustrates an exemplary coding summary 139 produced from exemplary patient encounter information.

The patient encounter illustrated in FIGS. 2C and 2D is fictitious and not the result of a real patient encounter. Thus, this fictitious medical data does not violate the privacy of any real individual under HIPAA or other federal or state laws.

This fictitious patient, a new outpatient, complained of a cough, chills, and tightness in the chest. During the patient encounter various boxes on the paper information template were checked off including a check of the patient's neck (box 40 FIG. 2D and normal green box 44 illustrated in FIG. 3). A diagnosis was also made in the Diagnoses box (new w/u complete box 41 FIG. 2D and FIG. 3) and the provider included handwritten notes. The provider spent about 30 with the patient.

The exemplary coding summary 139 is attached to the one or more digital images after the one or more medical codes are generated. The exemplary coding summary in box 139 is also illustrated in Table 6.

TABLE 6

CODING SUMMARY OUTPUT FROM PROCESSING OF
EXEMPLARY PAPER MEDICAL INFORMAITON FORM
ILLUSTRATED IN FIGS. 2C and 2D (box 139)

E/M=99203
History=DET (CC=COMP; HPI=COMP; PFMSH=DET; ROS=DET)
Exam=DET (13 Bullets; 6 Systems) / Complexity of MDM=MOD
(DX=MOD; RISK=MOD; Data=N/A)

As FIGS. 2C and 2D and Table 6 illustrate, an exemplary E/M code generated from this fictitious patient encounter was 99203 for a new outpatient (Table 5 and FIG. 11). The exemplary E/M code of 99203 is generated with the methods described herein.

Table 7 illustrates an exemplary invoice automatically generated from the information in Table 6. However, the present invention is not limited to such an exemplary invoice and other invoices can also be automatically generated and used to practice the invention.

TABLE 7

| ERgent Care Clinic | | |
|---|---|---|
| Patient: John Doe (New) | Date: Oct. 18, 2003 | Time: 12:00 p.m. |
| Chief Complaint: Cough and chest Congestion chills | | Exam: Detailed Exam |
| Fee: $59.00 | | Doctor: Dr. Janet Smith |
| Insurance: Blue Cross - Blue Shield | | Risk/Complexity: Moderate |
| Expected Insurance Payment: $35.00 | | Total Due from Patient: $14.00 |

TABLE 7-continued

ERgent Care Clinic

Exit Instructions: Fill prescription for DOXYCYCLINE, see family physician within three days.

Figure 13:
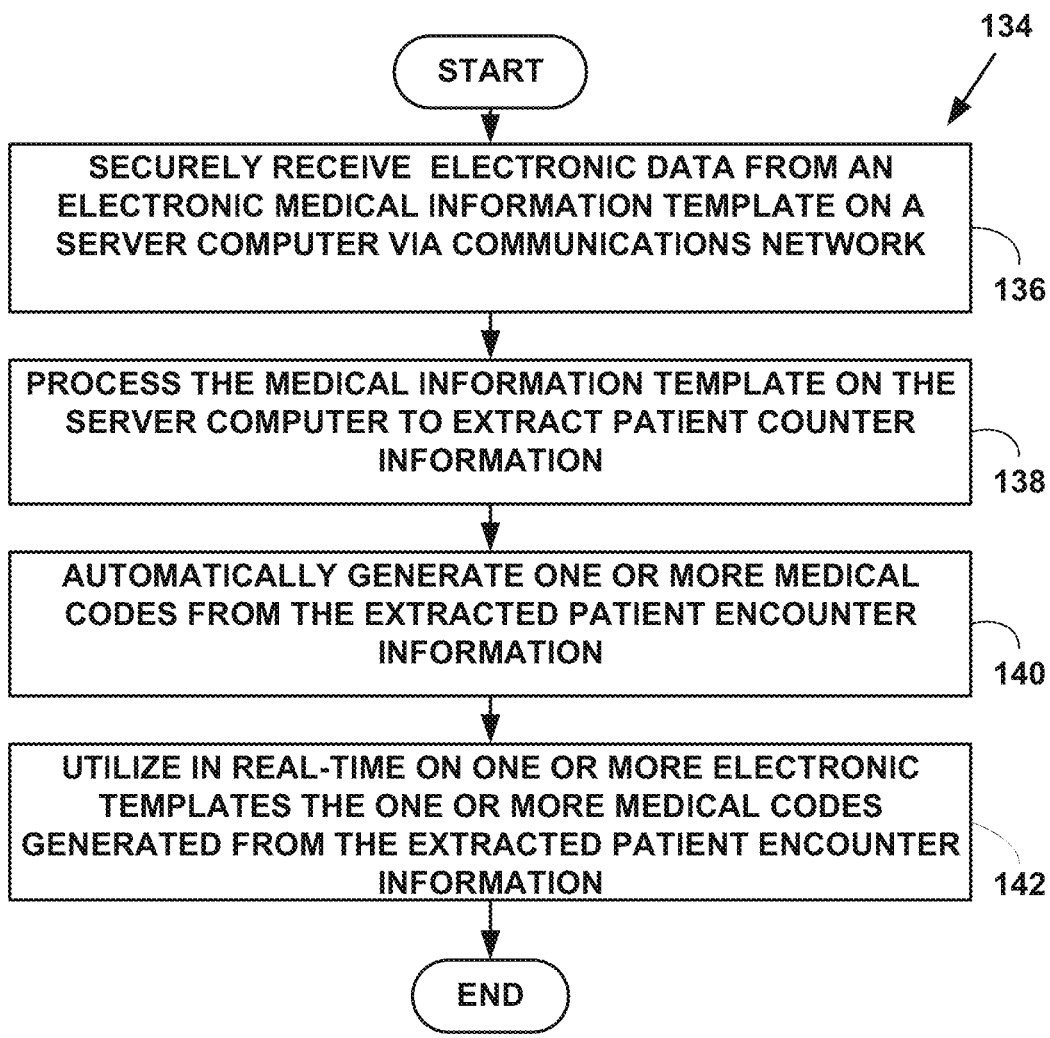
FIG. 13 is a flow diagram illustrating a method of processing medical information templates via the medical records system.

FIG. 13 is a flow diagram illustrating a Method 134 of processing medical information templates via a medical records system. At Step 136, electronic data created from an electronic medical information template 12' is securely received on a server computer 20a, 20b, 20c via a communications network 24. The electronic data was created on a client network devices 18 using an electronic medical information template 12'. At Step 138, the electronic data is automatically processed on the server computer 20a, 20b, 20c to extract patient encounter information. At Step 140, one or more medical codes are automatically generated from the extracted patient encounter information. The one or more medical codes generated include, but are not limited to, one or more of E/M, CPT, HCPCS, ICD-9, ICD-10, or other types of codes. At Step 142, the one or more medical codes generated from the extracted patient encounter information are presented on one or more electronic templates that are displayed on a graphical user interface (GUI) or the one or more electronic templates are utilized to produce additional medical information documents. The one or more electronic templates include, but are not limited to, an electronic invoice template, an electronic medical record template, a current compliant template, a nurse template, a review template, a diagnosis template; a provider template; and other types of electronic templates electronically to another software program, database or another data processing system.

Method 134 is used to process digital data extracted patient encounter information entered on client network devices 18 using an electronic medical information template 12' instead of a paper medical information template. Method 134 processes such electronic data in a manner similar to the digital images described for Methods 100 and 110.

Figure 14:
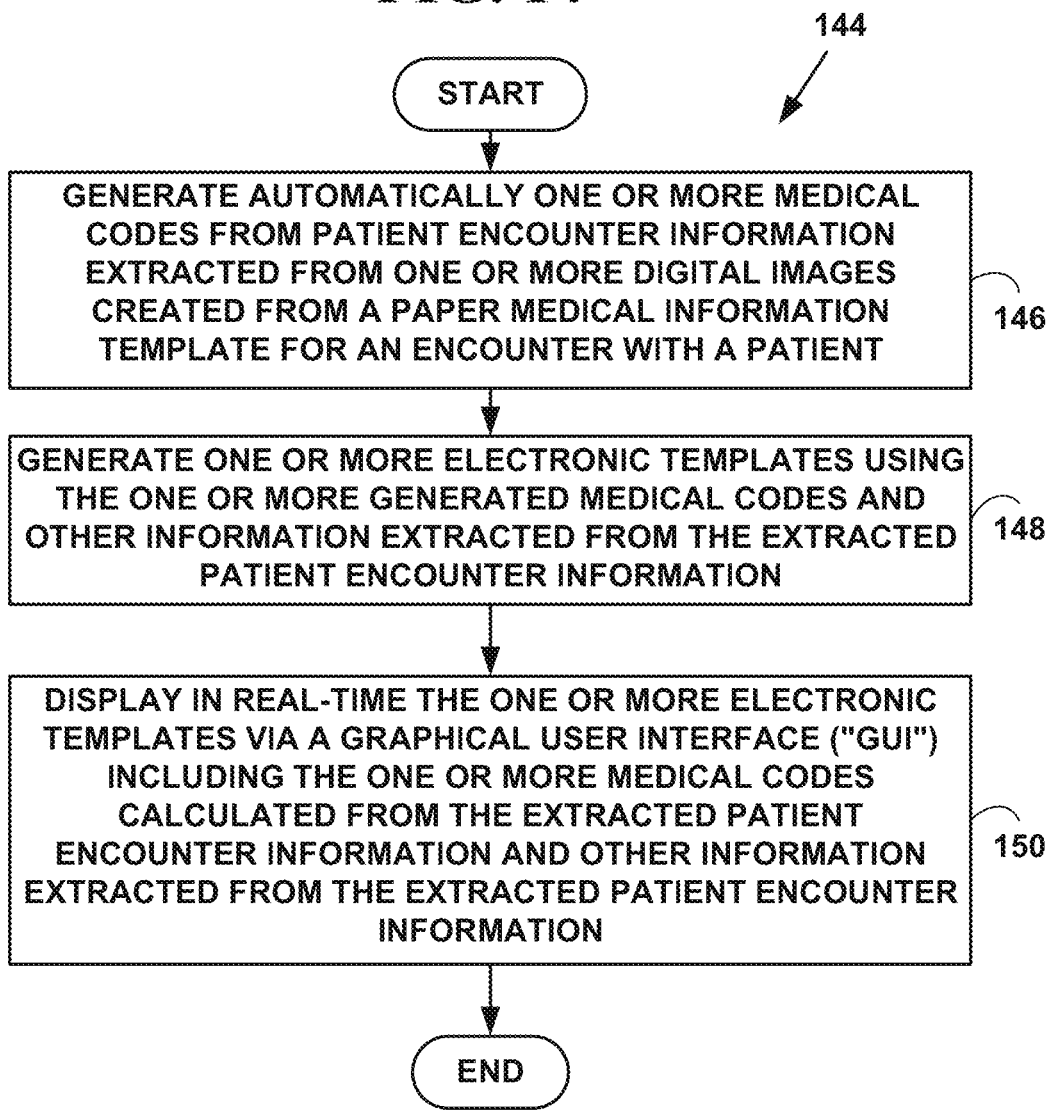
FIG. 14 is a flow diagram illustrating a method of processing medical information templates via the medical records system.

FIG. 14 is a flow diagram illustrating a Method 144 of processing medical information templates via the medical records system. At Step 146, one or more medical codes are generated automatically from patient encounter information extracted from one or more digital images created from a paper medical information template 12 for an encounter with a patient. The one or more medical codes generated include, but are not limited to, one or more of E/M, CPT, HCPCS, ICD-9, IDC-10, or other medical codes. At Step 148, one or more electronic templates are generated automatically using the one or more generated medical codes and other information extracted from the extracted patient encounter information. The one or more electronic templates include, but are not limited to, an electronic invoice template, an electronic medical record template, a current compliant template, a nurse template, a review template, a diagnosis template; a provider template; and other types of electronic templates. At Step 150, the one or more electronic templates that are displayed on a graphical user interface (GUI) or the one or more electronic templates that are utilized to produce additional medical information documents including the one or more medical codes generated from the extracted patient encounter information and other information extracted from the extracted patient encounter information.

Step 146 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

The methods and systems described herein were illustrated with respect to a patient examination view or perspective. However, the invention is not limited to this view or perspective. The methods and system described herein are also used to provide automated processing and real-time collection and display of other types of medical information associated with, or generated by a patient encounter to provide 360° view of an individual patient after a patient encounter. The methods and system are used to process, display and/or utilize in real-time all available information for a patient immediately after a patient encounter.

Although description of this method has been limited to the outpatient encounter, this same methodology may be applied to documentation and coding of in-hospital encounters, consults, preventative examinations and other types of patient encounters.

Figure 15:
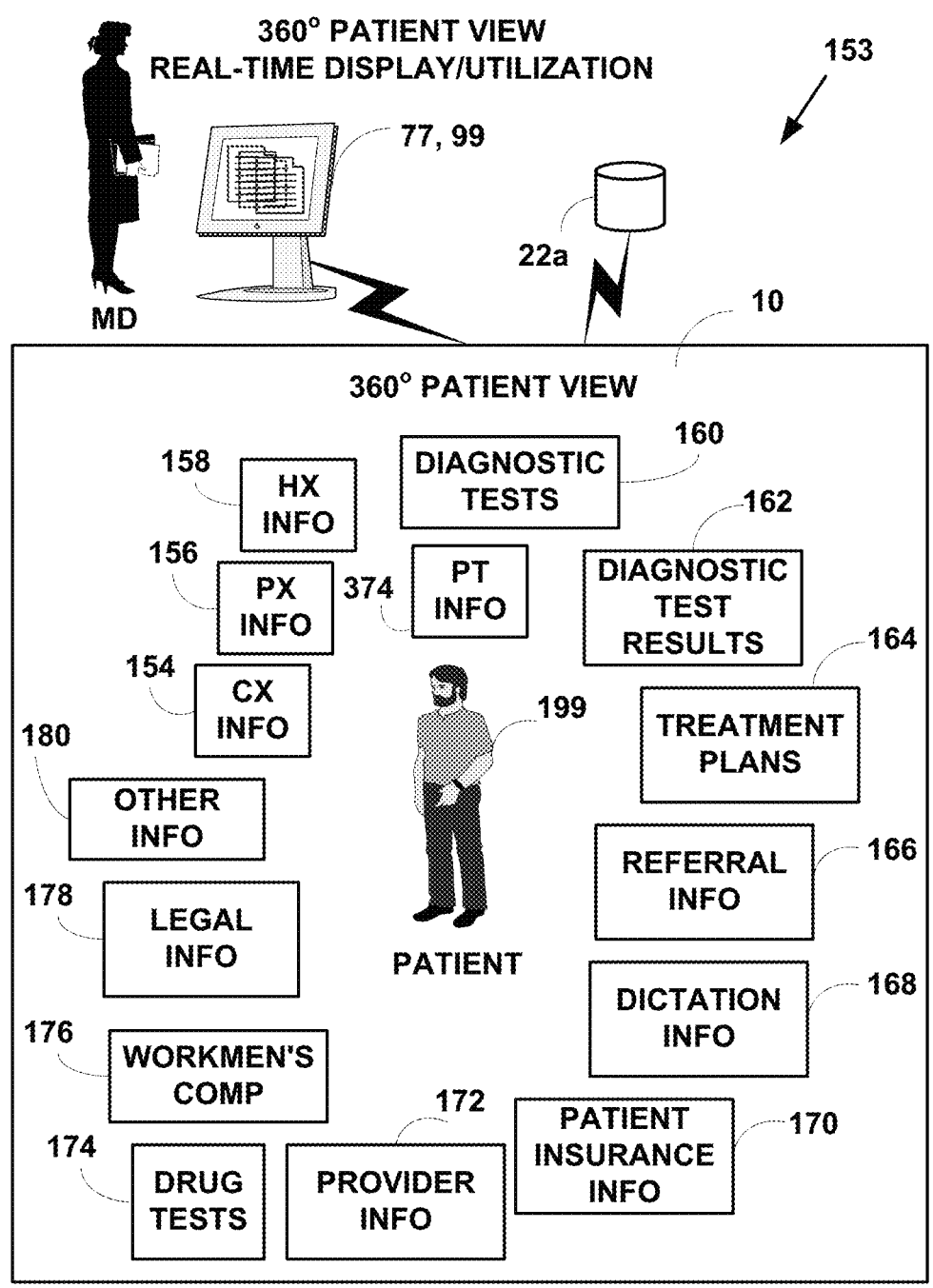
FIG. 15 is a block diagram illustrating a 360° real-time view of a patient encounter.

FIG. 15 is a block diagram illustrating a 360° real-time view 152 of a patient encounter. The 360° real-time view includes, but not limited to, HX 154, PX 156, CX 158 matrix information extracted, diagnostic procedures ordered 160 (e.g., blood tests, x-rays, MRI scans, CT scans, etc.); diagnostic procedures results 162; treatment plans 164; referral information 166; dictation information 168; patient insurance information 170; provider information 172; and information such drug testing information 174, workmen's comp information 176, legal information 178, and other types of information 180 associated with a patient and/or a patient encounter.

Figure 16:
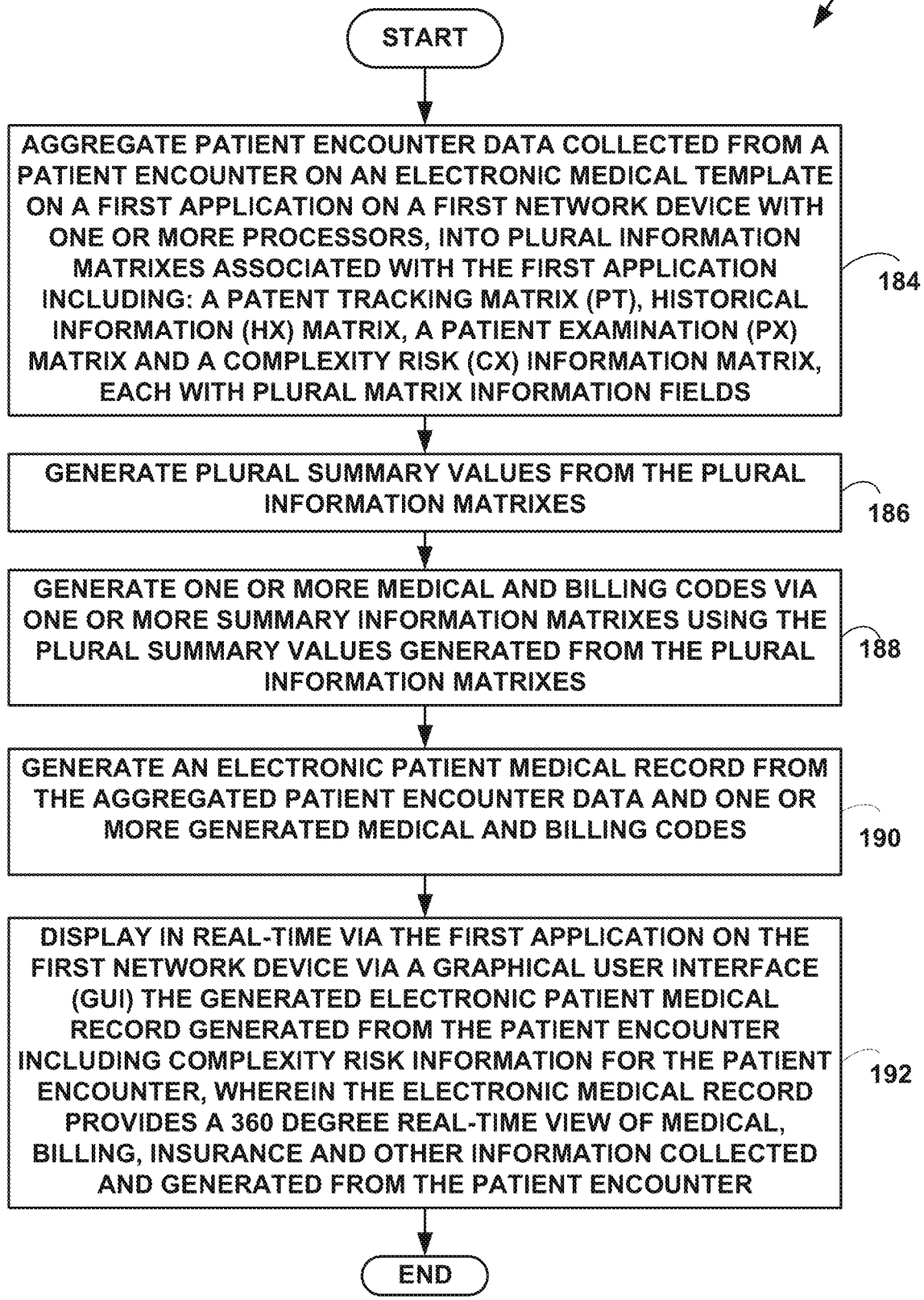
FIG. 16 is a flow diagram illustrating a method for automated processing of medical information.

Processing Patient Encounter Information from Electronic Medical Information Templates FIG. 16 is a flow diagram illustrating a Method 182 for automated processing of medical information. At Step 184, patient encounter data collected from a patient encounter on an electronic medical template is aggregated in real-time on a first application on a first network device with one or more processors. The patient encounter data is aggregated into plural information matrixes stored in a computer readable medium on the first network device associated with the first application including: a historical information (HX) matrix, a patient examination (PX) matrix and a complexity risk (CX) information matrix, each with plural matrix information fields stored in the computer readable medium. The CX information matrix helps eliminate an amount and complexity of patient encounter data collected and a number of diagnostic options to be considered during the patient encounter thereby reducing a medical risk associated with making a complex medical decision and limiting an amount and complexity of patient data to be processed and reviewed. At Step 186, plural summary values are generated from the plural information matrixes via the first application. At Step 188, one or more medical and billing codes are generated via one or more summary information matrixes using the plural summary values generated from the plurality of information matrixes via the first application. At Step 190, an electronic patient medical record is generated from the aggregated patient encounter data and one or more generated medical and billing codes. At Step 192, the generated electronic patent medical record generated from the patent encounter is displayed in real-time via the first application on the first network device via a graphical user interface (GUI) the electronic including complexity risk information for the patient encounter. The electronic medical record provides a 360 degree real-time view of medical, billing, insurance and other information collected and generated from the patient encounter.

Method 182 is illustrated with one exemplary embodiment. However, the present invention is not limited to such an exemplary embodiment and other embodiments can also be used to practice the invention.

In such an exemplary embodiment at Step 184, patient encounter data collected from a patient encounter (FIGS. 2D, 2D displayed electronically instead of using paper templates) on an electronic medical template 12' is aggregated on a first application 26 (e.g., 28, 30, 32, 33, etc.) on a first network device 18 with one or more processors. The patient encounter data is aggregated into plural information matrixes stored as data bits in a computer readable medium on the first network device 18 associated with the first application including: a historical information (HX) matrix 124, a patient examination (PX) matrix 126 and a complexity risk (CX) information matrix 128, each with plural matrix information fields (e.g., Tables, 1-5, FIGS. 8-10). The CX information matrix 128 helps eliminate an amount and complexity of patient encounter data collected and a number of diagnostic options to be considered during the patient encounter thereby reducing a medical risk associated with making a complex medical decision and limiting an amount and complexity of patient data to be processed and reviewed.

At Step 186, plural summary values are generated from the plural information matrixes 124, 126, 128 directly on the client network device 18. In another embodiment, the first application on the client network device 18 also establishes a communication via communications network 24 to server computer 20a, 20b, 20c and database 22a, 22b, 22c is used to generate additional summary values for the patient.

For example, if the patient is an established patient at the medical facility visited, then existing electronic medical information about the established patient can be retrieved from the database 22 and automatically added to the summary values. In one specific example, the additional summary values added may include existing medications prescribed to the patient, drugs the patient is allergic to, etc. Such an automatic update of the summary values helps lower the risk and complexity associated with the patient encounter as most medical patients do not have a clear understanding and do not clearly remember what medications may have been prescribed to them or exactly what drugs they may allergic to. A similar query may also be made to the patient medical insurance company to automatically obtain insurance coverage information. This helps lower the risk and complexity associated with insurance billing and/or collecting immediate payment from a patient after a patient encounter. However, such a query can only be made if the patient's medical insurance company has an electronic interface to provide such information.

In another embodiment, the methods and system described herein, including the dataflow 52 of FIG. 4 can be used to input paper insurance records for the patient. In such an embodiment, all of the patient's insurance information would then be available electronically.

If the patient is a new patient at the medical facility visited, a query may be made to automatically obtain the new patient medical records. The new patient medical records are automatically processed to generate additional summary values from the medical records. However, such a query can only be made if the patient's medical provider has an electronic interface to provide electronic medical records.

In another embodiment, the methods and system described herein, including the dataflow 52 of FIG. 4 can be used to input paper medical records for the patient. In such an embodiment, all of the patient's previous medical information from the medical records would then be available electronically.

In such embodiments, any information obtained from the quires to database 22 for any additional medical and/or insurance information is added to the summary values and/or used to create an additional type and count of the electronic check boxes used on the medical information templates and/or via the matrixes.

At Step 188, one or more medical and billing codes are generated via one or more Evaluation and Management (E/M) summary information matrixes 130, 132 using the plural summary values generated from the plurality of information matrixes (e.g., Table 6, FIGS. 11, 12, etc.)

At Step 190, an electronic patient medical record is generated from the aggregated patient encounter data and one or more generated medical and billing codes.

At Step 192, the generated electronic patent medical record generated from the patent encounter is displayed in real-time via the first application 32 on the first network device 18 via a graphical user interface (GUI) including complexity risk information 154 for the patient encounter. The electronic medical record provides a 360 degree real-time view 152 of medical, billing, insurance and other information collected and generated from the patient encounter (e.g., FIG. 15).

In one exemplary embodiment, FIG. 5 illustrates an exemplary data flow and FIG. 15 illustrates an exemplary real-time 360 degree view for the patient encounter described for Method 182 of FIG. 16. However, the present invention is not limited to these exemplary embodiments and other embodiments can also be used to practice the invention.

FIG. 17 is a block diagram of a screen shot 194 of a first portion 196 of an exemplary electronic medical information template.

Figure 18:
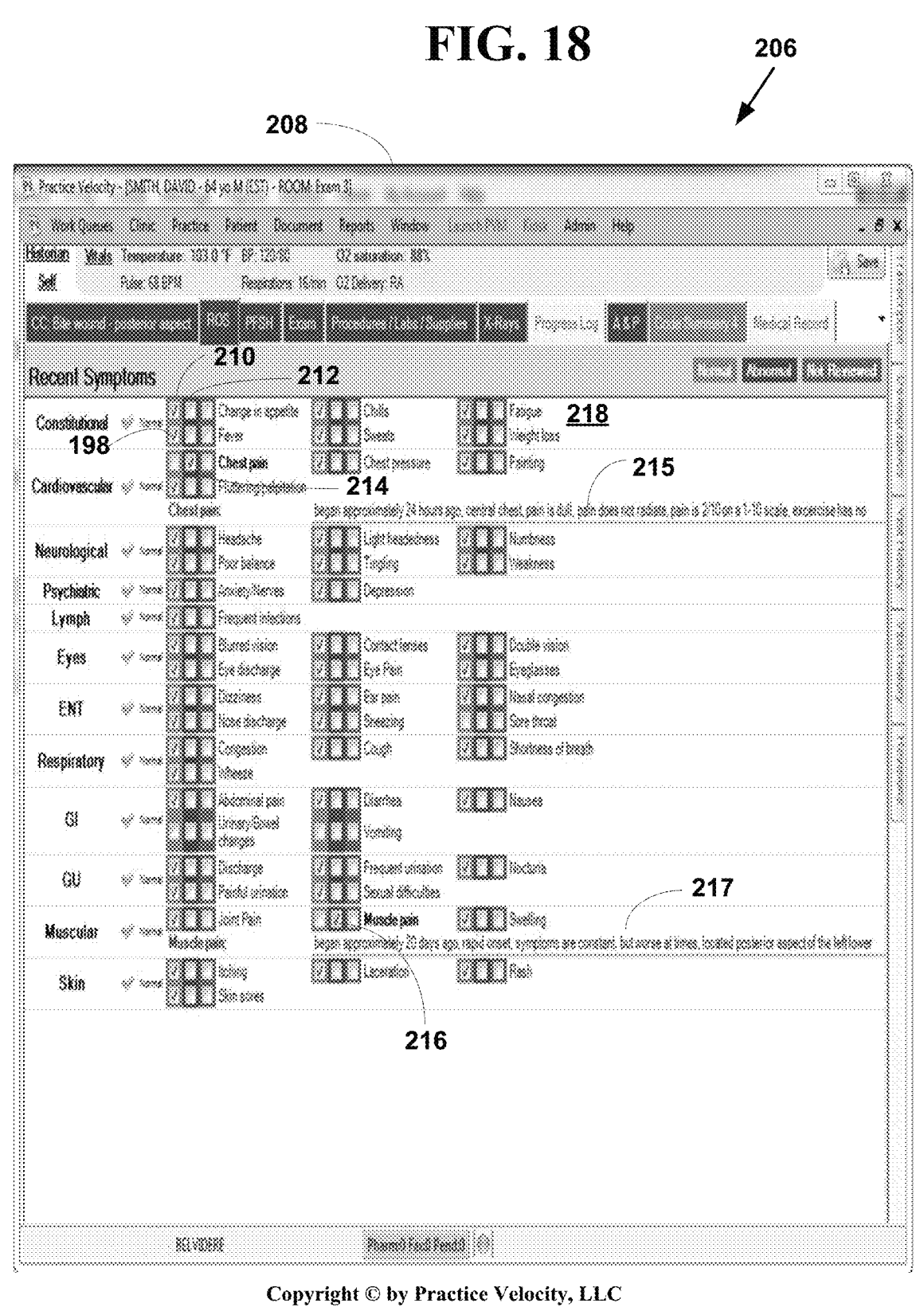
Figure 19:
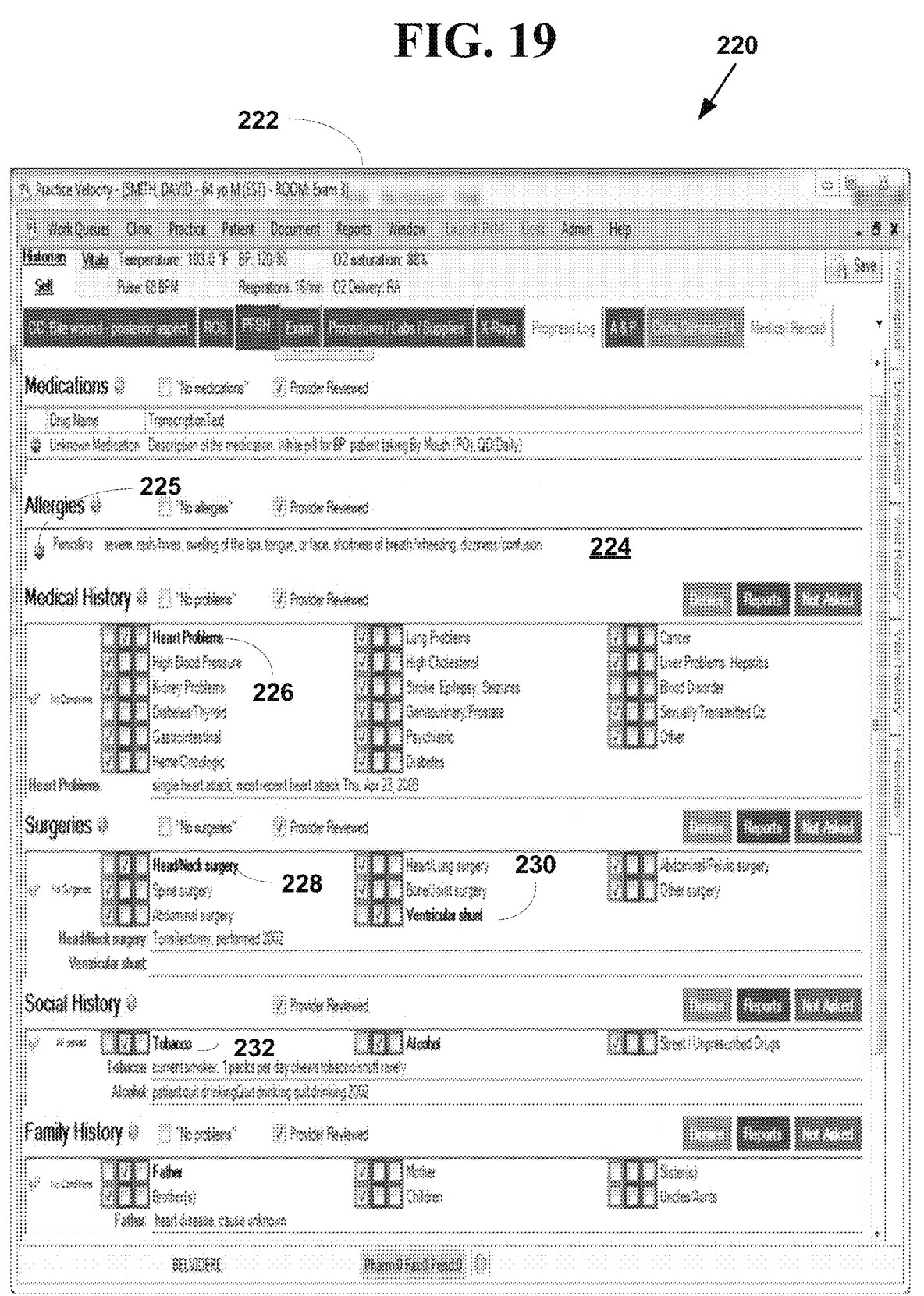

FIG. 18 is a block diagram of a screen shot 206 of a second portion 208 of an exemplary electronic medical information template, FIG. 19 is a block diagram of a screen shot 220 of a third portion 222 of an exemplary electronic medical information template.

Figure 20:
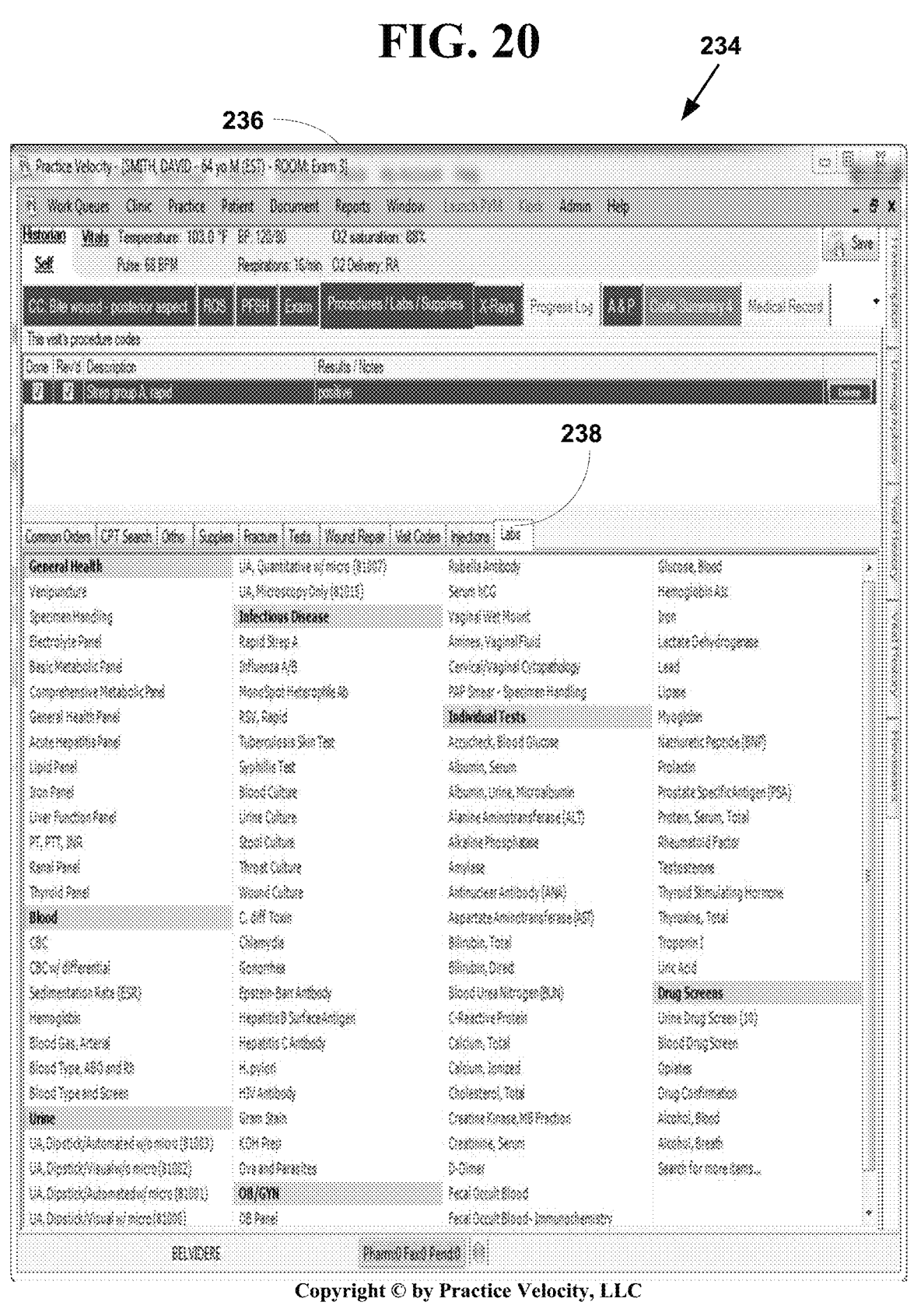

FIG. 20 is a block diagram of a screen shot 234 of a fourth portion 236 of an exemplary electronic medical information template.

Figure 21:
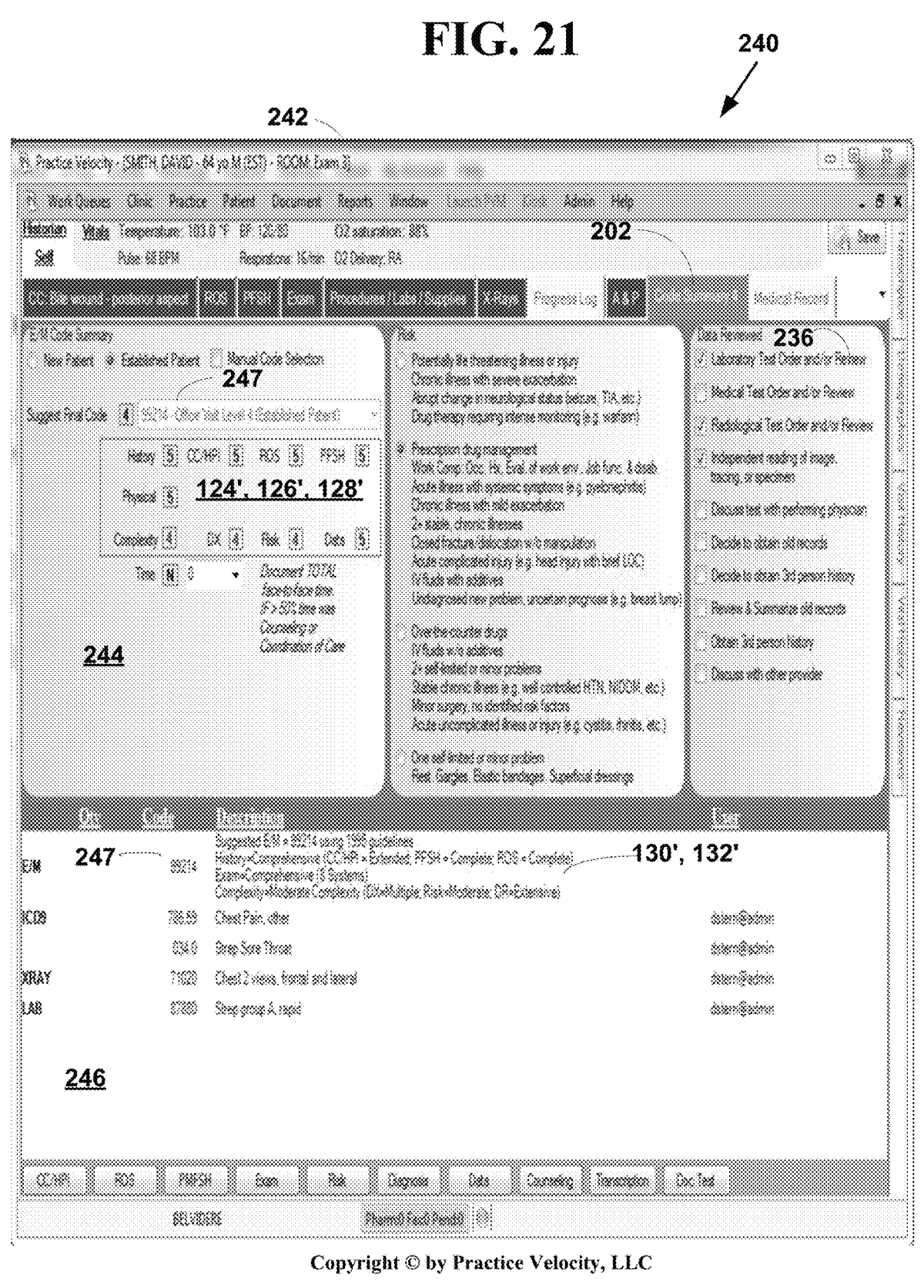

FIG. 21 is a block diagram of a screen shot 228 of a fifth portion 230 of an exemplary electronic medical information template.

Figure 22:
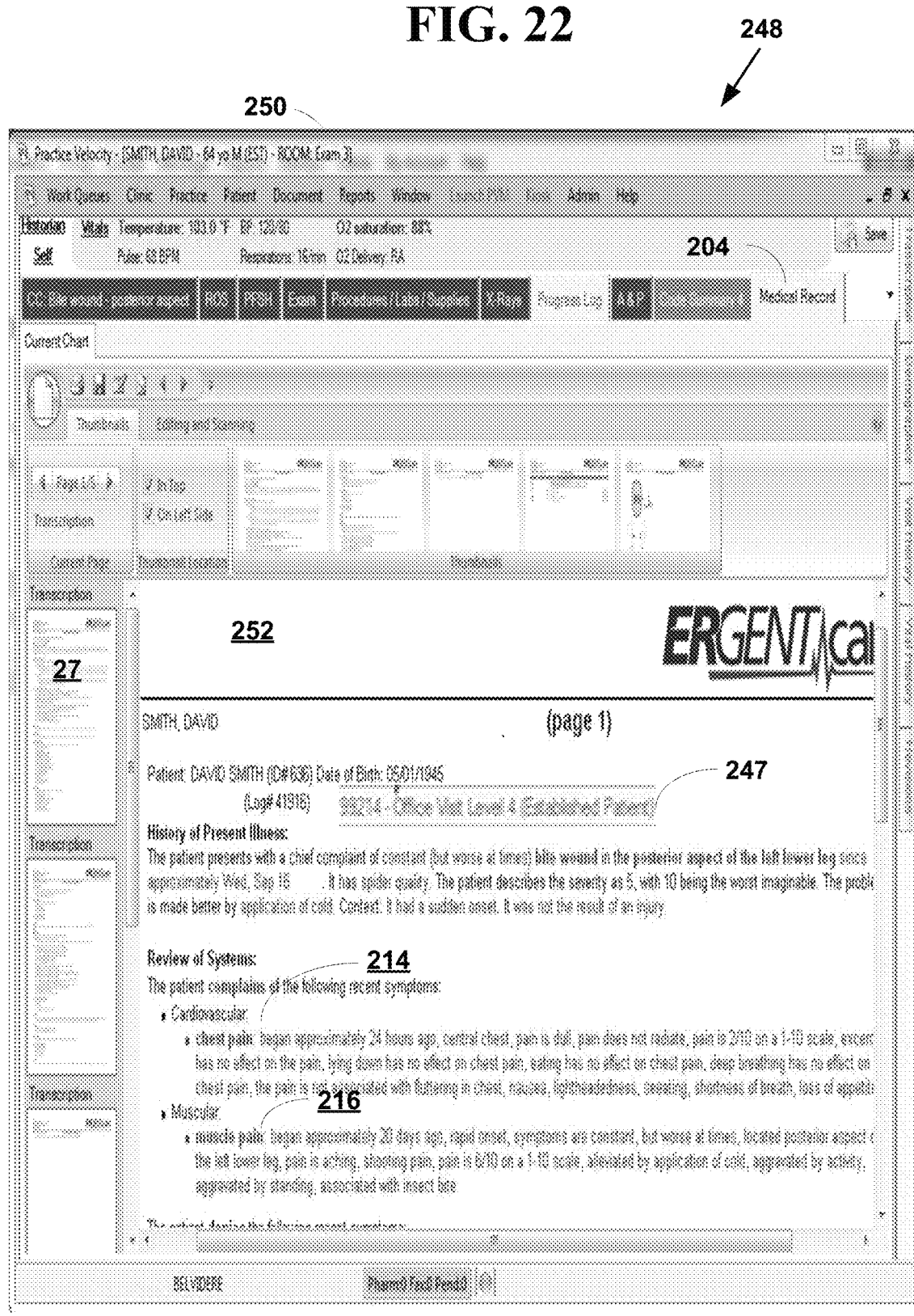

FIG. 22 is a block diagram of a screen shot 248 of a sixth portion 250 of an exemplary electronic medical information template.

FIGS. 17-23 are copyright © by Practice Velocity, LLC. All rights reserved.

FIGS. 17-23 illustrate portions of exemplary electronic medical information templates 12' displayed on a client network device 18. However, these portions are exemplary only and many more and different portions for the electronic medical information templates 12' are displayed on the client network device 18. The portions of the medical information templates 12' are stored in data structures in the computer readable medium of the client network devices 18.

FIGS. 17-23 illustrate plural portions of electronic medical records templates 12' generated for an exemplary fictional patient that enters an urgent care clinic as an existing patient that has visited this urgent care clinic before.

The exemplary fictional patient is a 64 year old male named David Smith and is in Exam Room 3. He has a bite wound from an unknown organism (e.g., a spider?, etc.) in the knee area. His application of ice made the bite area feel better. His temperature is 103° F., his blood pressure is 120/80. His pulse is 68 beats-per-minute. His in moderate pain and experiencing chest pain and muscle pain. He has heart problems, has a ventricular stunt installed, has had recent head and/or neck surgery. He is allergic to Penicillins.

FIG. 17 illustrates a first portion 196 of an exemplary electronic medical information template 12'. The first portion 196 is automatically and specifically sized to be displayed on a selected client network device 18. FIG. 17 illustrates two exemplary check boxes in a checked position 198. FIG. 17 illustrates a first portion of a medical information template to collect information about a new chief complaint (CC). In this example, the CC is a bite wound to the knee area.

FIGS. 17-23 illustrate a selection bar 200 that is selected to display various other portions of the electronic medical information template 12'. In embodiment, the graphical selection bar 200 includes graphical tabs to select portions corresponding directly to information collected for the HX, PX and CX matrixes 124, 126, 128 described above. However, the present invention is not limited to this embodiment and the graphical selection bar 200 can include other graphical tabs and other graphical selection bars can also be used to practice the invention. For example, in another embodiment, the selection bar 200 may not make any direct reference to any the monikers used in the matrixes.

The graphical selection bar 200 also includes graphical tabs to display the generated medical and billing codes 202 and the generated electronic medical record 204.

FIG. 18 illustrates a second portion 208 of the exemplary electronic medical information template 12' including a Review Of Systems (ROS) portion. ROS was described above (e.g., Table 1b for the HX matrix 124, etc.). The second portion 208 is automatically and specifically sized to be displayed on a selected client network device 18.

The second portion 208 illustrates plural columns of green check boxes 210 (leftmost column) and plural columns of red of check boxes 212 (middle column). As was described above the green check box indicates the provider examined the patient, but the patient does not have any abnormality in the indicated body area or system. The red check box indicates the provider examined the patient, but the patient does have one or more abnormalities in the indicated body area or system. Plural green and red check boxes in the checked position are illustrated in FIG. 18.

FIG. 18 also illustrates a third column of gray check boxes to the right the red check boxes. The display order on FIG. 18 is green, red, gray. In one embodiment, the gray check boxes are used to collect data for medical research studies and/or for statistical purposes, etc. The data collected by the grey check boxes is identified by a patient identifier that can be mapped back to the patient the data is collected from during the patient encounter. However, the data is stored just with a numeric patient identifier, so of the data is comprised, it does not violate any patient privacy rights under HIPAA.

In another embodiment, the third column of gray check boxes is used for specific practice types to provide additional data inputs to the HX, PX, CX and E/M matrixes 124, 126, 128, 130, 132 stored in the computer readable medium on the client network device 18.

However the present invention is not limited to the number or color or purpose of check boxes described and more, fewer and other types of numbers, purposes and colors of check boxes can also be used to practice the invention. In addition, the check boxes can be replaced with other graphical features (e.g., radio buttons, bullet buttons, etc.) that can be displayed in an on and off position by selecting and/or deselecting the graphical feature. Check boxes were used on the electronic medical information templates 12' since they were created and in some embodiments are identical to the paper medical information templates 12 used and described above.

For example, as is illustrated in FIG. 18, the exemplary patient with the bite wound to the knee has chest pain 214 and muscle pain 216 illustrated by a check mark in the red boxes for those recent symptoms. Additional text is entered 215, 217 by the provider via the client network device 18 to further describe the chest pain 214 and the muscle pain 216. The physician may also dictate additional details about the patient encounter into the dictation interface 27.

The exemplary patient does not have any of the other symptoms illustrated by the check mark in the green boxes for the other recent symptoms in the Constitutional box 218 such as no change in appetite, no fever, no chills, no sweats, no chest pressure, no fatigue, no weight loss, etc.

FIG. 19 illustrates a third portion 222 of the exemplary electronic medical information template 12' including a Personal Family and Social History (PFSH) portion. PFSH was described above (e.g., Table 1b for the HX matrix, etc.). The third portion 222 is automatically and specifically sized to be displayed on a selected client network device 18. The third portion 222 illustrates the patient is allergic to Penicillins 224, and plural red check boxes are checked for the exemplary patient including heart problems 226, head/neck surgery 228, ventricular stunt 230, and a smoker 232. When the red check boxes are checked, the font on the electronic medical information template 12' is changed to a bold font to make it easier for a viewer to visually determine a symptom from the patient encounter. Also, colored warning symbols (e.g., 225) are used (e.g., in box 224 for the allergy to Penicillins, etc.) indicate additional warnings to the physician. Box 224 illustrates one type of medical information for an established patient that may be queried and obtained from server computer 20a, 20b, 20c and added to the electronic medical information template 12' for the patient encounter.

FIG. 20 illustrates a fourth portion 236 of the exemplary electronic medical information template 12' including a medical and/or diagnostic procedures ordered 160 portion 236. The fourth portion 236 is automatically and specifically sized to be displayed on a selected client network device 18. The fourth portion 236 currently illustrates a lab test tab 238 selected. The lab test tab 238 displays available lab and diagnostic tests that can be selected for the patient.

FIG. 21 is a block diagram of a screen shot 240 of a fifth portion 242 of an exemplary electronic medical information template. The fifth portion 242 illustrates a summary of the information collected via the HX, PX, CX and E/M matrixes and displayed under the Code Summary 4 tab 202 (FIG. 17). FIG. 22 illustrates a first box 244 for displaying a count of matrixes values 124, 126, 128 determined by check boxes checked on the various portions of the electronic medical information template 12'. Box 244 illustrates History, CC/HPI, ROS, PFSH, Physical and Data with a number five. Complexity, DX and Risk with number four. It also illustrates a suggested Final Code of a number four and a final E/M code of 99214 (132, FIG. 12) for an established patient.

FIG. 21 also illustrates a second box 246 that includes a coding summary of the one or more medical and billing codes generated by Method 182 (and other methods described herein) from the exemplary electronic medical information template 12' portions illustrated in FIGS. 17-23. Table 8 illustrates the coding summary displayed in Box 246 (e.g., 99214, etc.) determined from E/M matrix 132 (FIG. 12).

The final E/M code 247 generated for this patient is 99214 (see FIG. 12) based on the values determined from the checked boxes and applied to matrixes HX, PX, and CX illustrated in FIGS. 8-10. The final ICD9 codes generated include 786.59 and 034.0.

TABLE 8

CODING SUMMARY OUTPUT FROM PROCESSING OF EXEMPLARY ELECTRONIC MEDICAL INFORMATION TEMPLATE 12' PORTIONS ILLUSTRATED IN FIGS. 17-23 and displayed in Box 246 on FIG. 21

Suggested E/M = 99214 (using 1995 guidelines...) (item 247 FIG. 21)
History=Comprehensive (CC/HPI = Extended; PFSH = Complete; ROS = Complete)
Exam=Comprehensive (8 systems)
Complexity=Moderate Complexity (DX=Multiple, Risk=Moderate; DR=Extensive)

| | |
|---|---|
| ICD9 | 786.59 - Chest Pain |
| | 034.0 - Sore Throat |
| XRAY | 71020 - Chest 2 views, frontal and lateral |
| LAB | 87880 - Strep Group A |

FIG. 22 is a block diagram of a screen shot 248 of a sixth portion 250 of an exemplary electronic medical information template 12'. The sixth portion 250 illustrates an exemplary electronic medical record 252 automatically generated in real-time from the patient encounter as the result of Method 182 (and other methods described herein). In one embodiment, the exemplary medical record is displayed by selected and displayed by selecting the Medical Record tab 202 (FIG. 17). Any symptoms that the patient is encountering and were collected during the patient encounter are displayed in a different font color (e.g., red and bold) for easy viewing on the medical record 252. For example, the chest pain 214 and muscle pain 216 collected from the red check boxes on FIG. 18 are displayed in the different color fonts on the medical record 252 in FIG. 22. In one embodiment, the electronic medical record 252 also displays the coding summary including the final E/M code 247. In another embodiment, the final E/M code 247 is not displayed on the electronic medical record 252. However, the present invention is not limited to this embodiment and other embodiments can also be used to practice the invention.

As is illustrated in FIGS. 17-23, plural portions of the electronic medical information templates 12' are automatically and successively displayed and automatically and specifically sized to be displayed on a selected client network device 18.

Figure 23:
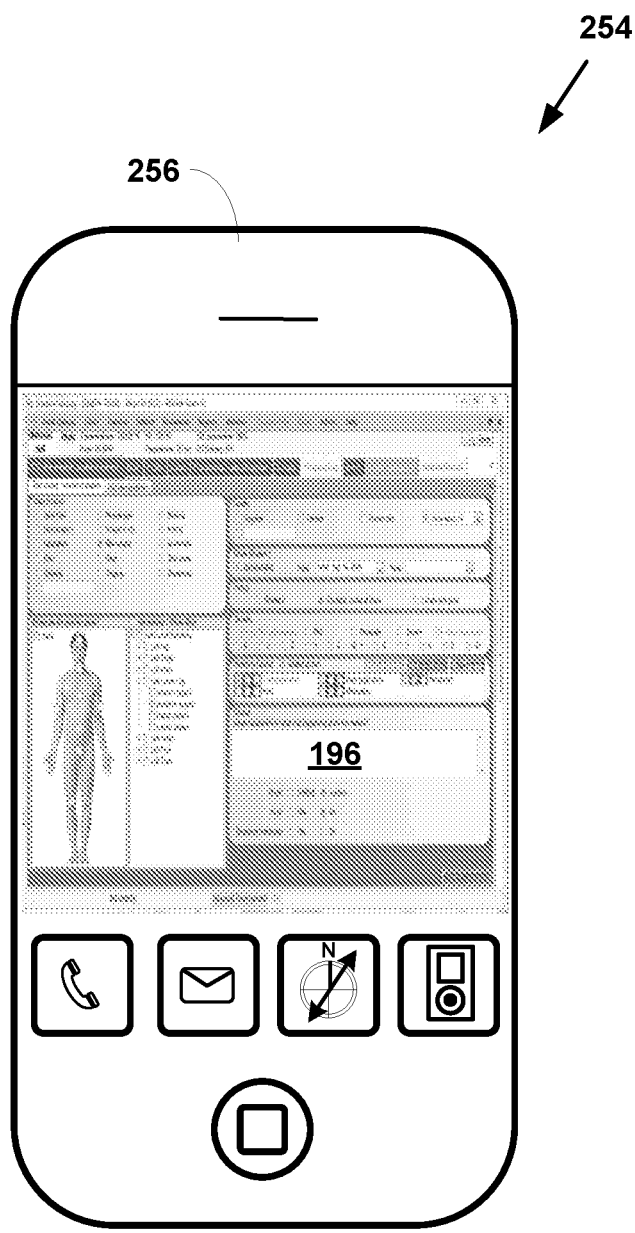

FIG. 23 is a block diagram of screen 254 shot illustrating an exemplary first portion 196 of a medical information template on a smart phone 256. In one exemplary embodiment, the application 26 (28, 29, 30, 32, 33) is an application for an iPhone, by Apple, Inc. as illustrated in FIG. 23. However, the present invention is not limited to such an embodiments and other embodiments, can also be used to practice the invention.

In one embodiment, the portions of the electronic medical information templates 12' displayed are identical to portions of the paper medical information templates 12. In another embodiment, the portions of the electronic information templates 12' are not identical to portions of the paper medical information template 12. In such an embodiment, the portions of the electronic information templates 12' displayed by the client network device 18 may appear in different orders, different sequences, different groups, etc. However, the methods described herein to automatically process medical information from the electronic medical information templates 12' are used no matter how the electronic templates 12' are portioned and/or displayed on the client network device.

Processing Electronic Medical Records with Cloud Computing Networks

FIG. 24 is a block diagram 258 illustrating an exemplary cloud computing network 24. The cloud computing network 24 is also referred to as a "cloud communications network" 24. However, the present invention is not limited to this cloud computing model and other cloud computing models can also be used to practice the invention. The exemplary cloud communications network includes both wired and/or wireless components of public and private networks.

In one embodiment, the cloud computing network 24 includes a cloud communications network 24 comprising plural different cloud component networks 272, 274, 276, 278. "Cloud computing" is a model for enabling, on-demand network access to a shared pool of configurable computing resources (e.g., public and private networks, servers, storage, applications, and services) that are shared, rapidly provisioned and released with minimal management effort or service provider interaction.

This exemplary cloud computing model for electronic information retrieval promotes availability for shared resources and comprises: (1) cloud computing essential characteristics; (2) cloud computing service models; and (3) cloud computing deployment models. However, the present invention is not limited to this cloud computing model and other cloud computing models can also be used to practice the invention.

Exemplary cloud computing essential characteristics appear in Table 9. However, the present invention is not limited to these essential characteristics and more, fewer or other characteristics can also be used to practice the invention.

TABLE 9

1. On-demand electronic content storage and retrieval services. Electronic medical records processors can unilaterally provision computing capabilities, such as server time and network storage, as needed automatically without requiring human interaction with each network server on the cloud communications network 24.
2. Broadband network access. Electronic medical records processing capabilities are available over plural broadband communications networks and accessed through standard mechanisms that promote use by heterogeneous thin or thick client platforms (e.g., mobile phones, smart phones, tablet computers, laptops, PDAs, etc.). The broadband network access includes high speed network access such as 3G and/or 4G wireless and/or wired and broadband and/or ultra-broad band (e.g., WiMAX, etc.) network access.
3. Resource pooling. Electronic medical records processing computing resources are pooled to serve multiple requesters using a multi-tenant model, with different physical and virtual resources dynamically assigned and reassigned according to electronic medical records TABLE 9-continued processing demand. There is location independence in that an requester of electronic medical records processing has no control and/or knowledge over the exact location of the provided by the electronic medical records processing resources but may be able to specify a location at a higher level of abstraction (e.g., country, state, or data center). Examples of pooled resources include storage, processing, memory, network bandwidth, virtual server network device and virtual target network devices.
4. Rapid elasticity. Capabilities can be rapidly and elastically provisioned, in some cases automatically, to quickly scale out and rapidly released to quickly scale for electronic medical records processing. To the electronic medical records processing storage and retrievers, the electronic medical records storage and retrieval capabilities available for provisioning appear to be unlimited and can be used in any quantity at any time.
5. Measured Services. Cloud computing systems automatically control and optimize resource use by leveraging a metering capability at some level of abstraction appropriate to the type of electronic medial records processing services (e.g., storage, processing, bandwidth, custom electronic content retrieval applications, etc.). Electronic medical records processing usage is monitored, controlled, and reported providing transparency for both the electronic content provider and the electronic medical records processor requester of the utilized electronic medical records processor service.

Exemplary cloud computing service models illustrated in FIG. 24 appear in Table 10. However, the present invention is not limited to these service models and more, fewer or other service models can also be used to practice the invention.

TABLE 10

1. Cloud Computing Software Applications 260 for an Electronic Medical Records Processing Service (CCSA 262). The capability to use the provider's applications 26, 28, 30, 32, 33 running on a cloud infrastructure 268. The cloud computing applications 262, are accessible from the server network device 20 from various client devices 18 through a thin client interface such as a web browser, etc. The user does not manage or control the underlying cloud infrastructure 264 including network, servers, operating systems, storage, or even individual application 26, 28, 30, 32, 33 capabilities, with the possible exception of limited user-specific application configuration settings.
2. Cloud Computing Infrastructure 264 for the an Electronic Medical Records Processing Service (CCI 266). The capability provided to the user is to provision processing, storage and retrieval, networks 24, 272, 274, 276, 278 and other fundamental computing resources where the consumer is able to deploy and run arbitrary software, which can include operating systems and applications 26, 28, 30, 32. 33 The user does not manage or control the underlying cloud infrastructure 264 but has control over operating systems, storage, deployed applications, and possibly limited control of select networking components (e.g., host firewalls, etc.).
3. Cloud Computing Platform 268 for the an Electronic Content Storage and Retrieval Service (CCP 2701). The capability provided to the user to deploy onto the cloud infrastructure 264 created or acquired applications created using programming languages and tools supported servers 20a, 20b, 20c, etc. The user not manage or control the underlying cloud infrastructure 264 including network, servers, operating systems, or storage, but has control over the deployed applications 26, 28, 30, 32, 33 and possibly application hosting environment configurations.

Exemplary cloud computing deployment models appear in Table 11. However, the present invention is not limited to these deployment models and more, fewer or other deployment models can also be used to practice the invention.

TABLE 11

1. Private cloud network 274. The cloud network infrastructure 264 is operated solely for an electronic medical records processing. It may be managed by the electronic content retrieval or a third party and may exist on premise or off premise.

TABLE 11-continued

2. Community cloud network 276. The cloud network infrastructure 264 is shared by several different organizations and supports a specific electronic content storage and retrieval community that has shared concerns (e.g., mission, security requirements, policy, compliance considerations, etc.). It may be managed by the different organizations or a third party and may exist on premise or off premise.
3. Public cloud network 278. The cloud network infrastructure 264 such as the Internet, PSTN, SATV, CATV, Internet TV, etc. is made available to the general public or a large industry group and is owned by one or more organizations selling cloud services.
4. Hybrid cloud network 272. The cloud network infrastructure 264 is a composition of two and/or more cloud networks 24 (e.g., private 274, community 276, and/or public 278, etc.) and/or other types of public and/or private networks (e.g., intranets, etc.) that remain unique entities but are bound together by standardized or proprietary technology that enables data and application portability (e.g., cloud bursting for load-balancing between clouds, etc.)

Cloud software 262 for electronic content retrieval takes full advantage of the cloud paradigm by being service oriented with a focus on statelessness, low coupling, modularity, and semantic interoperability for electronic content retrieval. However, cloud software services 264 can include various states.

Cloud storage of desired electronic content on a cloud computing network 24 includes agility, scalability, elasticity and multi-tenancy. Although a storage foundation may be comprised of block storage or file storage such as that exists on conventional networks, cloud storage is typically exposed to requesters of desired electronic content as cloud objects.

In one exemplary embodiment, the applications 26, 28, 30, 32, 33 offers cloud services for electronic content storage and retrieval. The applications 28, 30, 32 offers the cloud computing Infrastructure 264, 266 as a Service 62 (IaaS), including a cloud software infrastructure service 266, the cloud Platform 268 as a Service 270 (PaaS) including a cloud software platform service 270 and/or offers specific cloud software services as a Service 262 (SaaS) including a specific cloud software service 262 for electronic medical records processing. The IaaS, PaaS and SaaS include one or more of cloud services 262 comprising networking, storage, server network device, virtualization, operating system, middleware, run-time, data and/or application services, or plural combinations thereof, on the cloud communications network 24.

Figure 25:
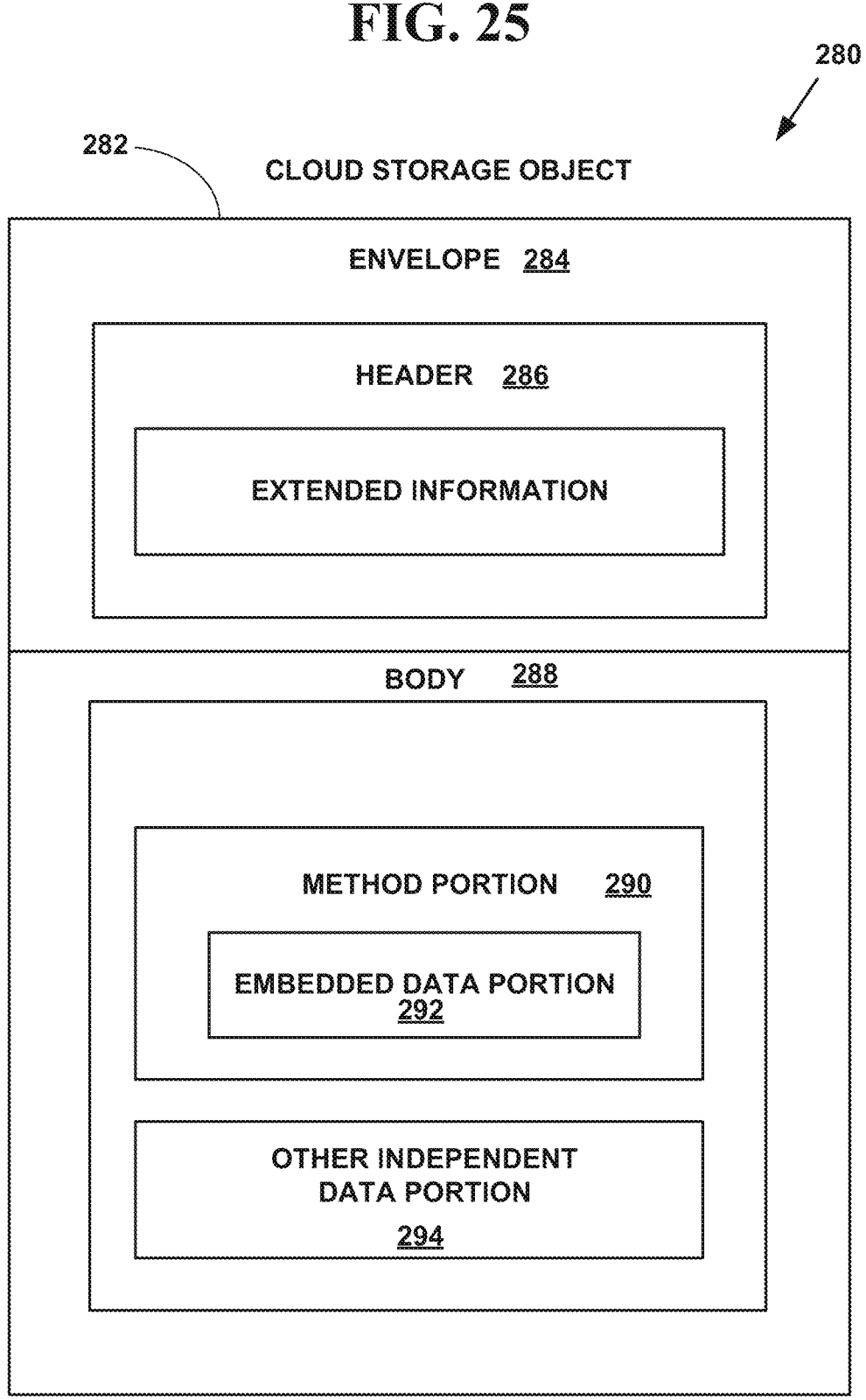
FIG. 25 is a block diagram illustrating an exemplary cloud storage object.

FIG. 25 is a block diagram 280 illustrating an exemplary cloud storage object 282.

The cloud storage object 282 includes an envelope portion 284, with a header portion 286, and a body portion 288. However, the present invention is not limited to such a cloud storage object 282 and other cloud storage objects and other cloud storage objects with more, fewer or other portions can also be used to practice the invention.

The envelope portion 284 uses unique namespace Uniform Resource Identifiers (URIs) and/or Uniform Resource Names (URNs), and/or Uniform Resource Locators (URLs) unique across the cloud communications network 24 to uniquely specify, location and version information and encoding rules used by the cloud storage object 282 across the whole cloud communications network 24. For more information, see IETF RFC-3305, Uniform Resource Identifiers (URIs), URLs, and Uniform Resource Names (URNs), the contents of which are incorporated by reference.

The envelope portion 284 of the cloud storage object 282 is followed by a header portion 86. The header portion 286 includes extended information about the cloud storage objects such as authorization and/or transaction information, etc.

The body portion 288 includes methods 290 (i.e., a sequence of instructions, etc.) for using embedded application-specific data in data elements 292. The body portion 288 typically includes only one portion of plural portions of application-specific data 292 and independent data 294 so the cloud storage object 282 can provide distributed, redundant fault tolerant, security and privacy features described herein.

Cloud storage objects 282 have proven experimentally to be a highly scalable, available and reliable layer of abstraction that also minimizes the limitations of common file systems. Cloud storage objects 282 also provide low latency and low storage and transmission costs.

Cloud storage objects 282 are comprised of many distributed resources, but function as a single storage object, are highly fault tolerant through redundancy and provide distribution of desired electronic content across public communication networks 278, and one or more private networks 274, community networks 276 and hybrid networks 272 of the cloud communications network 24. Cloud storage objects 282 are also highly durable because of creation of copies of portions of desired electronic content across such networks 272, 274, 276, 278 of the cloud communications network 24. Cloud storage objects 282 includes one or more portions of desired electronic content and can be stored on any of the 272, 274, 276, 278 networks of the cloud communications network 24. Cloud storage objects 82 are transparent to a requester of desired electronic content and are managed by cloud applications 26, 28, 30, 32, 33.

In one embodiment, cloud storage objects 282 are configurable arbitrary objects with a size up to hundreds of terabytes, each accompanied by with a few kilobytes of metadata. Cloud objects are organized into and identified by a unique identifier unique across the whole cloud communications network 24. However, the present invention is not limited to the cloud storage objects described, and more fewer and other types of cloud storage objects can be used to practice the invention.

Cloud storage objects 282 present a single unified namespace or object-space and manages desired electronic content by user or administrator-defined policies storage and retrieval policies. Cloud storage objects includes Representational state transfer (REST), Simple Object Access Protocol (SOAP), Lightweight Directory Access Protocol (LDAP) and/or Application Programming Interface (API) objects and/or other types of cloud storage objects. However, the present invention is not limited to the cloud storage objects described, and more fewer and other types of cloud storage objects can be used to practice the invention.

REST is a protocol specification that characterizes and constrains macro-interactions storage objects of the four components of a cloud communications network 24, namely origin servers, gateways, proxies and clients, without imposing limitations on the individual participants.

SOAP is a protocol specification for exchanging structured information in the implementation of cloud services with storage objects. SOAP has at least three major characteristics: (1) Extensibility (including security/encryption, routing, etc.); (2) Neutrality (SOAP can be used over any transport protocol such as HTTP, SMTP or even TCP, etc.), and (3) Independence (SOAP allows for almost any programming model to be used, etc.)

LDAP is a software protocol for enabling storage and retrieval of electronic content and other resources such as files and devices on the cloud communications network 24. LDAP is a "lightweight" version of Directory Access Protocol (DAP), which is part of X.500, a standard for directory services in a network. LDAP may be used with X.509 security and other security methods for secure storage and retrieval. X.509 is public key digital certificate standard developed as part of the X.500 directory specification. X.509 is used for secure management and distribution of digitally signed certificates across networks.

An API is a particular set of rules and specifications that software programs can follow to communicate with each other. It serves as an interface between different software programs and facilitates their interaction.

Automated Processing of Electronic Medical Records with Cloud Computing

Figure 26B:
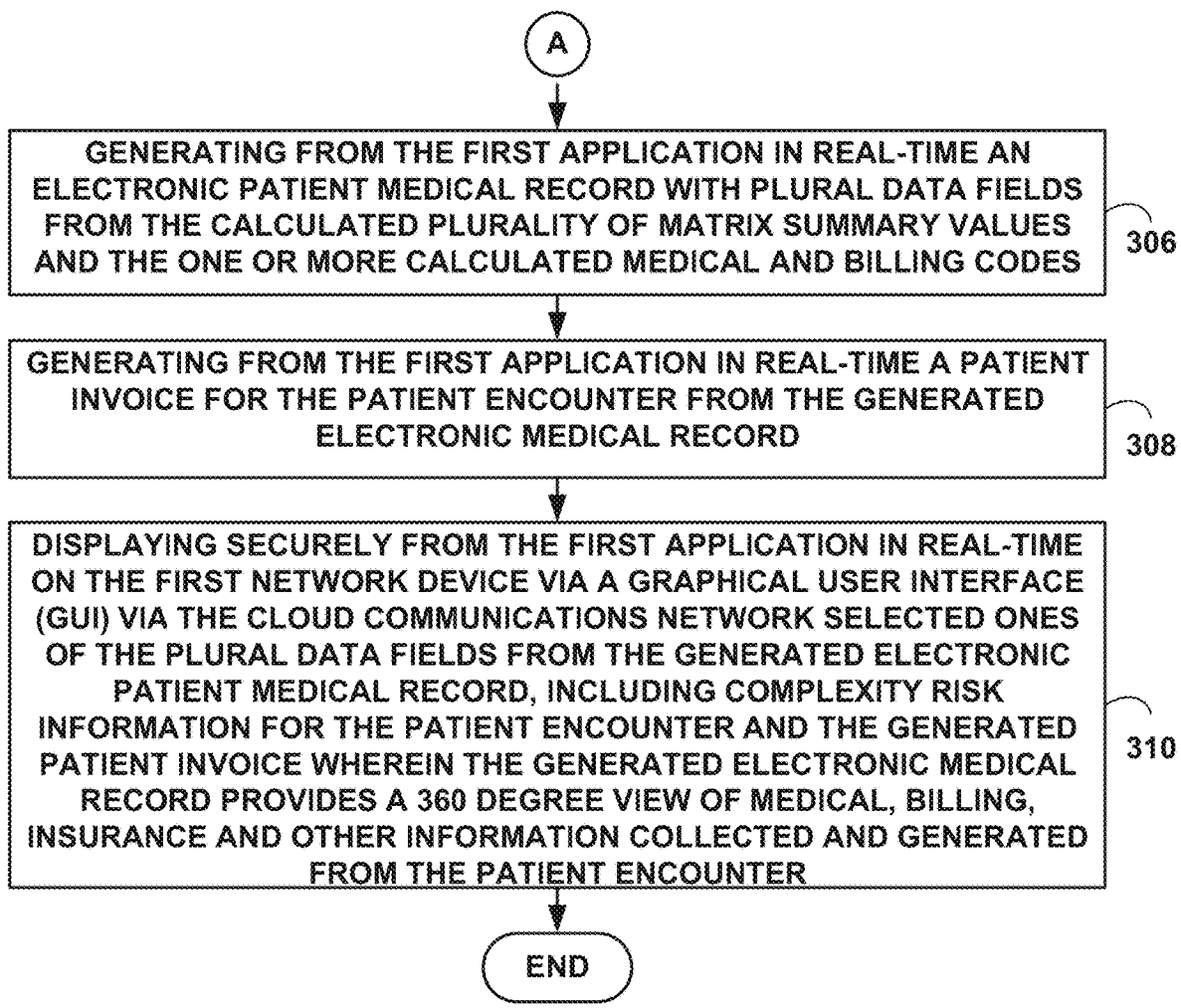

FIGS. 26A and 26B are a flow diagram illustrating a Method 298 for automated processing of electronic medical records with cloud computing. In FIG. 26A at Step 300 data from a patient encounter is collected into a plural data fields on one or more different electronic medical templates on a first application on a first network device with one or more processors via a cloud communications network comprising: one or more public communication networks, one or more private networks, one or more community networks and one or more hybrid networks. At Step 302, the first application aggregates in real-time the collected patient encounter data into a plural information matrixes stored in one or more cloud storage objects. The plural information matrixes include: a patient tracking matrix (PT), historical information (HX) matrix, patient examination (PX) matrix, complexity risk (CX) information matrix and an Evaluation and Management (E/M) summary information matrix, each with a plurality of matrix information fields. The plural information matrixes help eliminate an amount and complexity of patient encounter data collected and reduce a number of diagnostic options to be considered during the patient encounter, thereby reducing a medical risk associated with making a complex medical decision for the patient encounter and limiting an amount and complexity of patient data to be processed and reviewed. At Step 304, the first application calculates in real-time plural matrix summary values from the plural information matrixes. At Step 306, the first application calculates in real-time one or more medical and billing codes using the calculated plural matrix summary values. In FIG. 26B at Step 308, the first application generates in real-time an electronic patient medical record with plural data fields from the calculated plural matrix summary values and the one or more calculated medical and billing codes. At Step 310, the first application generates in real-time a patient invoice for the patient encounter from the generated electronic medical record. At Step 312, the first application displays in real-time on the first network device via a graphical user interface (GUI) via the cloud communications network selected ones of the plural data fields from the generated electronic patient medical record, including complexity risk information for the patient encounter and the generated patient invoice wherein the generated electronic medical record provides a three hundred sixty degree view of medical, billing, insurance and other information collected and generated from the patient encounter.

Method 298 is illustrated with one exemplary embodiment. However, the present invention is not limited to this embodiment and other embodiments can be used to practice the invention.

In such an exemplary embodiment at in FIG. 26A at Step 300 data from a patient encounter 27 is collected into a plural data fields 40, 41, 198-217 on one or more different electronic medical templates 12', 196, 208, 222, 236, 242 on a first application 26, 28, 30, 32, 33 on a first network device 18 with one or more processors via a cloud communications network 24 comprising: one or more public communication networks 278, one or more private networks 274, one or more community networks 276 and one or more hybrid networks 272.

At Step 302, the first application 26, 28, 30, 32, 33 aggregates in real-time the collected patient encounter data into a plural information matrixes stored one or more cloud storage objects 282. The plural information matrixes include: a patient tracking matrix (PT) 374, historical information (HX) matrix 124, patient examination (PX) 126 matrix, complexity risk (CX) 128 information matrix and an Evaluation and Management (E/M) summary information matrix 130, 132, each with a plurality of matrix information fields. The plural information matrixes 124, 126, 128, 130, 132 help eliminate an amount and complexity of patient encounter data collected and reduce a number of diagnostic options to be considered during the patient encounter, thereby reducing a medical risk associated with making a complex medical decision for the patient encounter and limiting an amount and complexity of patient data to be processed and reviewed.

In one embodiment, the first application 26, 28, 30, 32, 33 offers a cloud computing Infrastructure 264 as a Service (IaaS) 266, a cloud Platform 268 as a Service (PaaS) 270 and offers an electronic medical records processing Specific cloud software service 260 as a Service (SaaS) 262 including one or more different software services 26, 28, 30, 32, 33 for automated processing of medical records information. However, the present invention is not limited to such an embodiment and more fewer and other types of cloud and non-cloud services can be used to practice the invention.

In one embodiment, Step 302 further includes automatically making one or more queries to a second application 26, 28, 30, 32, 32 on a second network device 20*a*, 20*b*, 20*c* with one or more processors via the cloud communications network 24 to obtain existing electronic medical records 252 or electronic medical insurance records for the patient, if any are available. However, the present invention is not limited to such an embodiment and the present invention can be practiced with and/or without this additional query.

At Step 304, the first application 26, 28, 29, 30, 32 calculates in real-time plural matrix summary values 124', 126', 128', 130', 132' (FIGS. 8-10) from the plural information matrixes 124, 126, 128, 130, 132.

At Step 306, the first application calculates 26, 28, 30, 32 in real-time one or more medical and billing codes 247 (FIGS. 11, 12, 21, Tables 4 and 5, etc.) using the calculated plural matrix summary values 124', 126', 128', 130', 132'.

In FIG. 26B at Step 308, the first application 26, 28, 29, 30, 32 generates in real-time an electronic patient medical record 252 with plural data fields from the calculated plural matrix summary values 124', 126', 128', 130', 132' and the one or more calculated medical and billing codes 247.

At Step 310, the first application 26, 28, 39, 30, 32 generates in real-time a patient invoice 75 for the patient encounter from the generated electronic medical record 252.

At Step 312, the first application 26, 28, 30, 32 securely displays in real-time on the first network device 18 via a graphical user interface (GUI) via the cloud communications network 24 selected ones of the plural data fields from the generated electronic patient medical record 252, including complexity risk information 247 for the patient encounter and the generated patient invoice 75 wherein the generated electronic medical record 252 provides a three hundred sixty degree view 77, 99 of medical, billing, insurance and other information collected and generated from the patient encounter.

In one embodiment, the secure display includes using the security and/or encryption methods (e.g., WEP, DES, 3DES, AES, MD5, SSL TLS, etc.) described herein to securely display information from the patient encounter.

In all methods and systems described herein, secure sending, receiving, storage and viewing of patient information on the cloud communications network 24 and/or non-cloud communications network 24 is necessary and is used as required under the Health Insurance Portability and Accountability Act ("HIPAA"), 42 U.S.C. 1320d, et. seq. and other Federal and state laws enacted in the United States to protect patient privacy.

Figure 27:
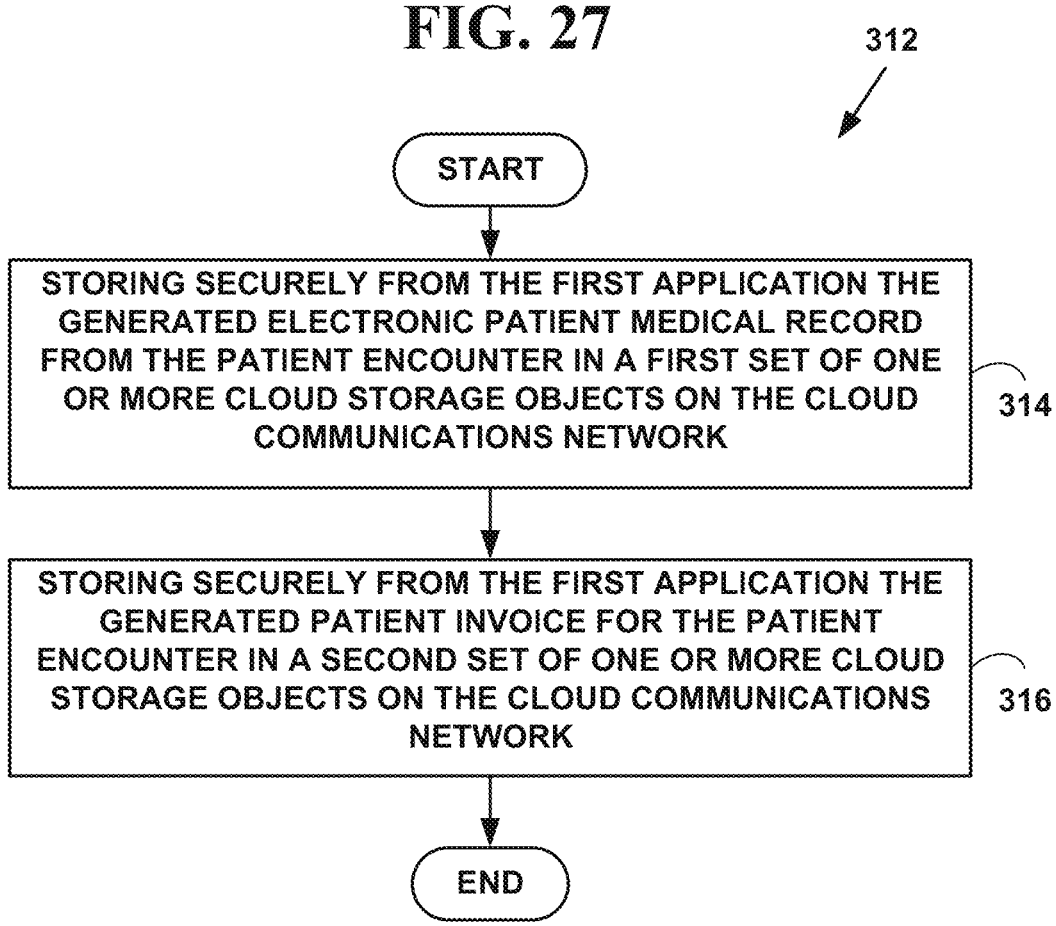
FIG. 27 is a flow diagram illustrating a method for automated processing of electronic medical records with cloud computing.

FIG. 27 is a flow diagram illustrating a Method 312 for automated processing of electronic medical records with cloud computing. At Step 314, the first application securely stores the generated electronic patient medical record from the patient encounter in a first set of one or more cloud storage objects on the cloud communications network. At Step 316, the first application securely stores the generated patient invoice for the patient encounter in a second set of one or more cloud storage objects on the cloud communications network.

Method 312 is illustrated with one exemplary embodiment. However, the present invention is not limited to this embodiment and other embodiments can be used to practice the invention.

In such an exemplary embodiment at Step 314 the first application 26, 28, 30, 32, 33 securely stores the generated electronic patient medical record 252 from the patient encounter in a first set of one or more cloud storage objects 282 on the cloud communications network 24.

At Step 316, the first application 26, 28, 30, 32, 33 securely stores the generated patient invoice 75 for the patient encounter in a second set of one or more cloud storage objects 282' on the cloud communications network 24.

Figure 28:
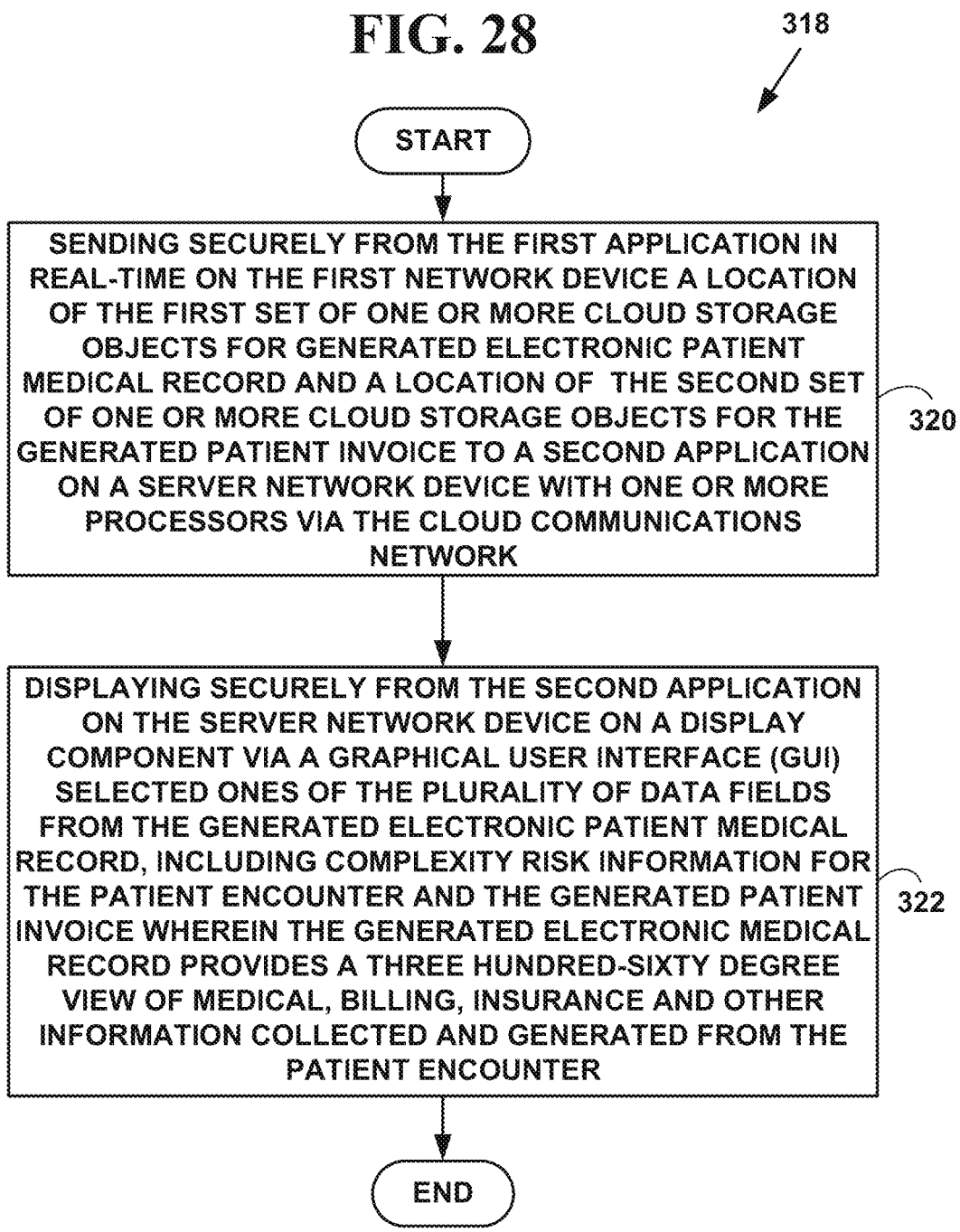
FIG. 28 is a flow diagram illustrating a method for automated processing of electronic medical records with cloud computing.

FIG. 28 is a flow diagram illustrating a Method 318 for automated processing of electronic medical records with cloud computing. At Step 320, the first application securely sends in real-time on the first network device a location of the first set of one or more cloud storage objects for generated electronic patient medical record and a location of the second set of one or more cloud storage objects for the generated patient invoice to a second application on a server network device with one or more processors via the cloud communications network. At Step 322, the second application on the server network device securely displays on a display component via a graphical user interface (GUI) selected ones of the plurality of data fields from the generated electronic patient medical record, including complexity risk information for the patient encounter and the generated patient invoice wherein the generated electronic medical record provides a three hundred-sixty degree view of medical, billing, insurance and other information collected and generated from the patient encounter.

Method 318 is illustrated with one exemplary embodiment. However, the present invention is not limited to this embodiment and other embodiments can be used to practice the invention.

In such an exemplary embodiment at Step 320, the first application 26, 28, 29, 30, 32, 33, securely sends in real-time on the first network device 18 a location of the first set of one or more cloud storage objects 282 for generated electronic patient medical record 252 and a location of the second set of one or more cloud storage objects 282' for the generated patient invoice 75 to a second application 26', 28', 29', 30', 32', 33' on a server network device 20a, 20b, 20c with one or more processors via the cloud communications network 24.

At Step 322, the second application 26', 28', 29', 30', 32', 33' on the server network device 20a, 20b, 20c securely displays on a display component via a graphical user interface (GUI) selected ones of the plural data fields from the generated electronic patient medical record 252, including complexity risk information 247 for the patient encounter and the generated patient invoice 75 wherein the generated electronic medical record 252 provides a three hundred sixty degree view 77, 99 of medical, billing, insurance and other information collected and generated from the patient encounter.

In one embodiment, the one or more electronic medical templates include a medical practice template, electronic invoice template, electronic medical record template, a current compliant template, a diagnosis template, a nurse template, a review template, and/or an insurance provider template. However, the present invention is not limited to the electronic medical templates described and more, fewer or other electronic medical templates can be used to practice the invention.

In one embodiment, the plural medical practice templates used with Method 298 include an electronic medical template for pediatrics, obstetrics and gynecology, cardiology, neurology, family practice medicine, emergency room medicine, walk-in clinics and/or or urgent care clinics. However, the present invention is not limited to the medical practice templates described and more, fewer or other electronic medical practice templates can be used to practice the invention.

In one embodiment, one or more of the medical practice templates include, but are not limited to the following additional features and/or data entry fields in addition to those describe herein above and illustrated in the figures: (1) Menopause Documentation: to enter a date of a last menses; (2) Pregnancy Electronic Due Date Calculator (EDC): After entering the last menses in the menopause documentation field, the Pregnancy EDC calculator automatically calculates the Due Date along with the number of weeks into the pregnancy; (3) Clinical decision support bar: that includes a first color (e.g., green, yellow, etc.) that changes into a second color (e.g., red, black, etc.) when any vital signs (e.g., blood pressure, temperature, etc.) are out of normal ranges; (4) Clinical decision support alert and action plan: (e.g., Body Mass Index out of range launching the user into plans to order specific interventions for the patient); (5) Pharyngitis Alert: This alert is set off when a diagnosis of Pharyngitis is recorded for a patient, but a Strep Screen has not been ordered for the patient; (6) History Not Completed: In the event the patient is experiencing a medical emergency, this documentation field is located on both the PFSH and ROS screens 124, and checking the box will provide automatic E/M coding for exam elements; (7) New Condition, Workup Planned: If this field is selected, the provider is given a pop up that allows documentation of a Differential Diagnosis; (8) Provider to Provider Notes section: Enables provider to record written communication note to another provider for subsequent visits; (9) Preformatted Discharge Notes: The provider can select user-specific preformatted discharge notes for the patient; (10) Visit Summary: Allows the provider to select the number of prior visits that the provider desires to view within the visit history tab by selecting the number of visits in the "Show Last visit _____ summaries;" (11) Summary Notes: will show the disposition and the medications dispensed on the visits including a viewing link for any radiographic images obtained, that will then open the patient chart and allow documentation of the diagnostic images; (12) Third Party Primary Historian: If a user selects someone other than the patient as the "Primary Historian", a practice may disable coding credit towards "Data Reviewed" in complexity of medical decision making. This option can be disabled at the practice level; (13) Electronic Signature Collection: Allows the clinic staff to check that a patient has been given the discharge documents to the patient/guardian, and for the patient/guardian to sign they have received them. Allows audits that the documents were given and the signature was received; (14) Document Multiple Protocols: Clinics that need to document a patient visit using the pre-set protocols that they have set up for an employer paid service, can pull in up to four protocols and can document each of them in one charting session. As each protocol has been completed, with orders being entered, the protocol header tab turns green. As soon as all the protocols have been completed, the Header "Protocol" tab turns from Red to Green; (15) Integration with Laboratory Services: Users are able to order labs electronically and receive the results electronically via Lab Corp and Quest Services; (16) Virtual Phone Encounters: This feature allows Users to log an encounter where a patient is not physically in the clinic but receives a service via telephone or Internet. The Provider will be able to use ePrescribe functionality in a virtual encounter. A User can enter notes for a Virtual Encounter. Once the patient is registered, the user will see the patient's name listed on the Virtual Encounter row of a "Tracking Boards", and the User will have the ability to enter in the notes of what transpired during the telephone encounter; (17) X-ray Interface: supports sending patient information and x-ray orders to Radlink. A link is displayed that reads "View Image" which will launch an x-ray viewer; (18) Date of Birth Notification: A patient that visits a clinic who has either had a birthday the day prior to a visit, or if the patient has a birthday within two weeks of a visit, will have a notification screen appear to notify the user of the date of birth so the health care provider can wish the patient a Happy Birthday; (19) Clinical Quality Measures (CQM) and National Framework of Qualifications (NQF) Reports: For each of the Centers for Medicare and Medicaid meaningful use objectives with a percentage-based measure are used. Users have the ability to report the numerators and denominators of each meaningful use measure and automatically calculate the resultant percentage-based meaningful use measures for which CMS requires an eligible professional to submit at the end of an Electronic Health Records (HER) reporting period; (20) Plots of Vitals Charts: When the patient's vitals have been entered the user will see that the current days vitals are immediately displayed. The vitals can then be graphed in several formats including line, bar, pie chart and/or other types of graphing; (21) Medication Reconciliation: All medications entered by the clinic staff, as well as the E-Rx prescribed medications in the patient history are displayed to check for harmful interactions; (22) Public Health Surveillance Queries and Peports: In compliance with Certified Commission for Healthcare Information Technology (CCHIT), users can electronically record, modify, retrieve, and submit syndrome-based public health surveillance information in accordance with the standard (and applicable implementation specifications) specified in CCHIT guidelines; (23) Matrix calcuation and coding results reports: for a one-screen view of matrix scoring details, including E/M, diagnosis codes, procedures codes, etc.; (24) Multi-Colored Patient, Billing and Insurance Alerts: A pop-up alert icon appears when a patient alert and/or a note have been entered. The types of alerts are color coordinated: (a) Yellow—patient related notes, (b) Red—patient related alert type notes, (c) Green—billing related notes, (d) Aqua—unknown altert, and (e) Dark Blue—clinical notes and/or (25) Referrals—Referral Management is completed via a referral template and offers administrative users an effective management tool to follow up, update, review, schedule, and manage referral orders for medical services to be performed by a provider other than the rendering provider. A Referral Management page is displayed on the GUI and displays a single page view of all referral orders a practice and/or clinic has completed.

However, the present invention is not limited to the medical practice template features and/or data entry fields described and more, fewer or other electronic medical practice template features and/or data entry fields can be used to practice the invention.

Figure 29:
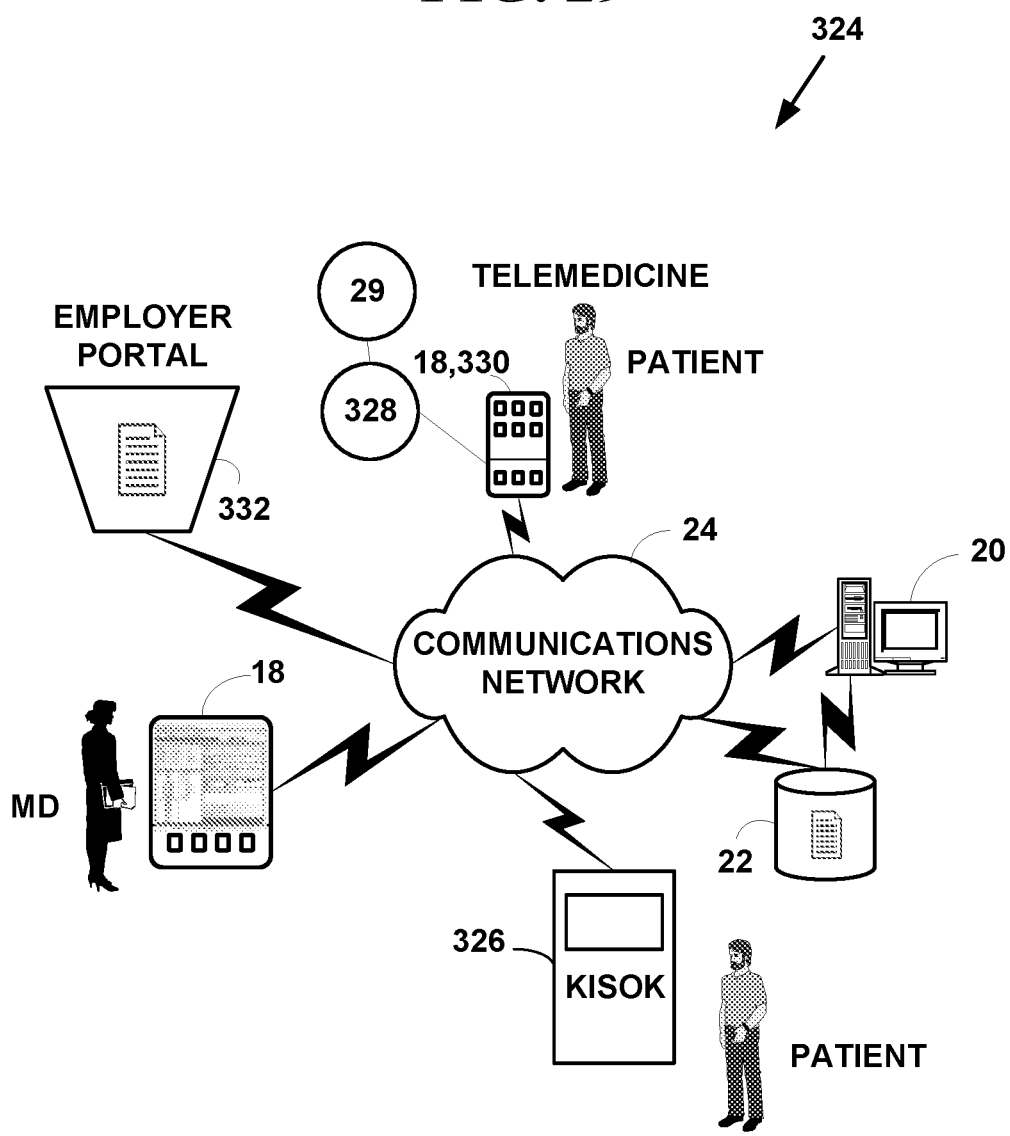
FIG. 29 is a block diagram illustrating additional components of the medical records system of FIG. 1.

FIG. 29 is a block diagram 324 illustrating additional components of the medical records system of FIG. 1. A secure electronic kiosk 326 is provided to allow a patient to enter patient appointment and registration information and preliminary patient encounter information. A secure patient encounter application 328 and/or telemedicine application 29 is provided to a client network device 330 to allow a patient to enter patient appointment and registration information and preliminary patient encounter information via a network device 18 such as a smart phone, tablet, etc. A secure employer portal 332 is provided to view services billed to an employer for employer provided health insurance or for the workman's compensation visits by a patient.

Figure 30:
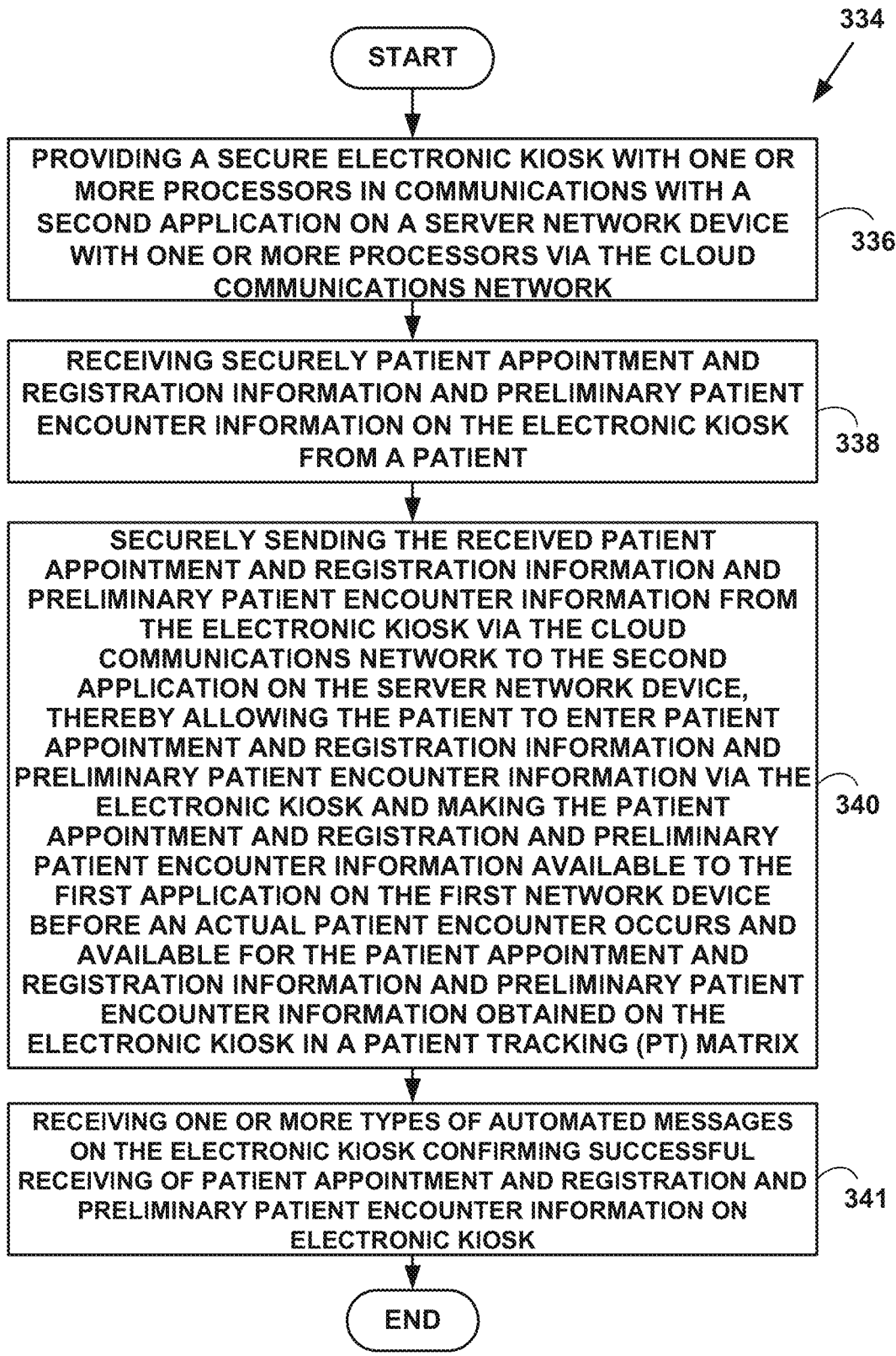
FIG. 30 is a flow diagram illustrating a method for automated processing of electronic medical records with cloud computing.

FIG. 30 is a flow diagram illustrating a Method 334 for automated processing of electronic medical records with cloud computing. At Step 336, secure electronic kiosk with one or more processors is provided in communications with a second application on a server network device with one or more processors via the cloud communications network. At Step 338, patient appointment and registration information and preliminary patient encounter information is securely received on the electronic kiosk from a patient. At Step 340, the received patient appointment and registration information and preliminary patient encounter information is securely sent from the electronic kiosk via the cloud communications network to the second application on the server network device, thereby allowing the patient to enter patient appointment and registration information and preliminary patient encounter information via the electronic kiosk and making the patient appointment and registration and preliminary patient encounter information available to the first application on the first network device before an actual patient encounter occurs. At Step 341, one or more types of automated messages are received on the electronic kiosk confirming successful receiving of patient appointment and registration and preliminary patient encounter information on electronic kiosk.

Method 334 is illustrated with one exemplary embodiment. However, the present invention is not limited to this embodiment and other embodiments can be used to practice the invention.

In such an exemplary embodiment at Step 336, a secure electronic kiosk 326 with one or more processors is provided in communications with a second application 26', 28', 29', 30', 32', 33' on a server network device 20a, 20b, 20c with one or more processors via the cloud communications network 24.

At Step 338, patient appointment and registration information and preliminary patient encounter information is securely received on the electronic kiosk 326 from a patient.

At Step 340, the received patient appointment and registration information and preliminary patient encounter information is securely sent from the electronic kiosk 326 via the cloud communications network 24 to the second application 26', 28' 29', 30', 32', 33' on the server network device 20a, 20b, 20c, thereby allowing the patient to enter patient appointment and registration information and preliminary patient encounter information via the electronic kiosk 326 and making the patient appointment and registration and preliminary patient encounter information available to the first application 26, 28, 29 30, 32, 33 on the first network device before 18 an actual patient encounter occurs.

At Step 341, one or more types of automated messages are received on the electronic kiosk 326 confirming successful receiving of patient appointment and registration and preliminary patient encounter information on electronic kiosk 326

Figure 31:
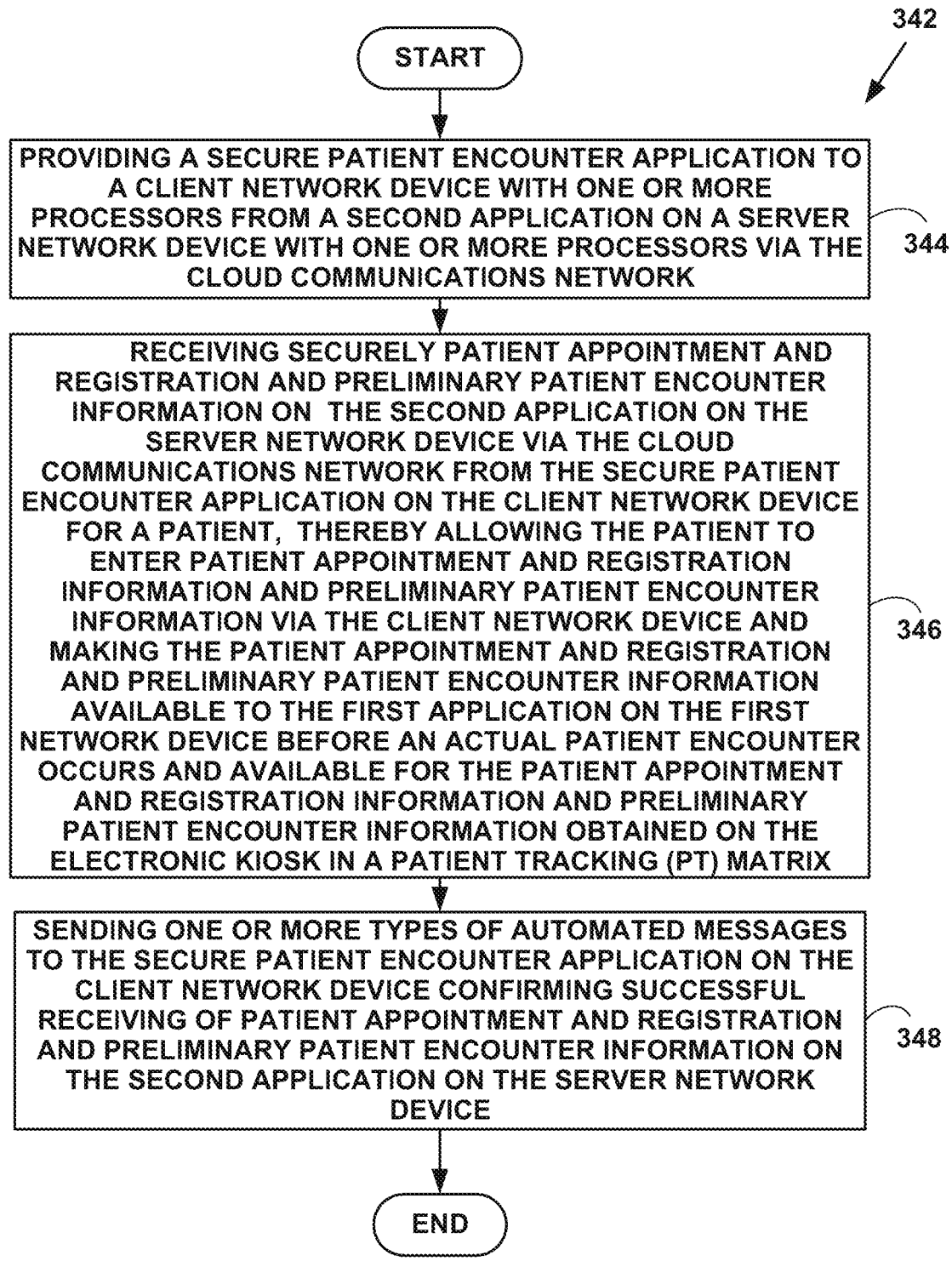
FIG. 31 is a flow diagram illustrating a method for automated processing of electronic medical records with cloud computing.

FIG. 31 is a flow diagram illustrating a Method 342 for automated processing of electronic medical records with cloud computing. At Step 344, a secure patient encounter application is provided to a client network device with one or more processors from a second application on a server network device with one or more processors via the cloud communications network. At Step 346, patient appointment and registration and preliminary patient encounter information is securely received on the second application on the server network device via the cloud communications network from the secure patient encounter application on the client network device for a patient, thereby allowing the patient to enter patient appointment and registration and preliminary patient encounter information via the secure patient encounter application on the client network device and making the patient appointment and registration and preliminary patient encounter information available to the first application on the first network device before an actual patient encounter occurs. At Step 348, one or more types of automated messages are sent to the secure patient encounter application on the client network device confirming successful receiving of patient appointment and registration and preliminary patient encounter information on the second application on the server network device.

Method 342 is illustrated with one exemplary embodiment. However, the present invention is not limited to this embodiment and other embodiments can be used to practice the invention.

In such an exemplary embodiment at Step 344, a secure patient encounter application 328 is provided to a client network device 330 (also, 18, wearable network devices, etc.) with one or more processors from a second application 26', 28', 29', 30', 32', 33' on a server network device 20a, 20b, 20c, with one or more processors via the cloud communications network 24.

At Step 346, patient appointment and registration and preliminary patient encounter information is securely received on the second application 26', 28', 29', 30', 32', 33' on the server network device 20a, 20b, 20c, via the cloud communications network 24 from the secure patient encounter application 238 on the client network device 330 for a patient, thereby allowing the patient to enter patient appointment and registration and preliminary patient encounter information via the secure patient encounter application 238 on the client network device 330 and making the patient appointment and registration and preliminary patient encounter information available to the first application 26, 28, 29, 30, 32, 33 on the first network device 18 before an actual patient encounter occurs. Thus, any patient can enter patient appointment and registration and preliminary patient encounter information from any location anywhere on the cloud communications network 24.

At Step 348, one or more types of automated messages are sent to the secure patient encounter application 328 on the client network device 330 confirming successful receiving of patient appointment and registration and preliminary patient encounter information on the second application 26', 29', 28', 30', 32', 33' on the server network device 20a, 20b, 20c. The automated messages include automated text messages, instant messages, voice messages, e-mail messages, audio messages, video messages, and/or other types of messages. However, the present invention is not limited to such an embodiment and more, fewer or other types of messages can be used to practice the invention.

Figure 32:
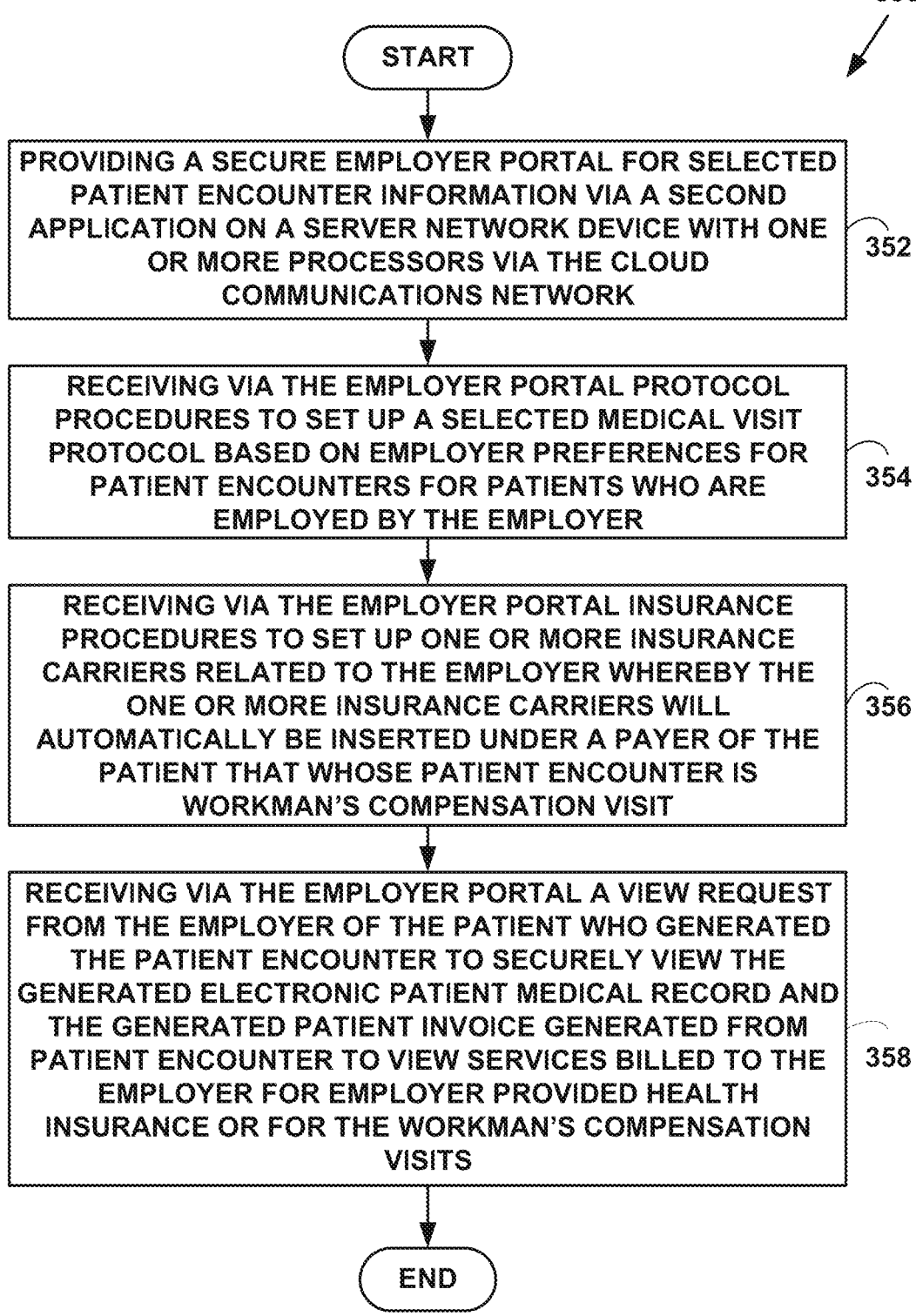
FIG. 32 is a flow diagram illustrating a method for automated processing of electronic medical records with cloud computing.

FIG. 32 is a flow diagram illustrating a Method 350 for automated processing of electronic medical records with cloud computing. At Step 352, a secure employer portal is provided for selected patient encounter information via a second application on a server network device with one or more processors via the cloud communications network. At Step 354, protocol procedures are received via the employer portal to set up a selected medical visit protocol based on employer preferences for patient encounters for patients who are employed by the employer. At Step 356, insurance procedures are received via the employer portal procedures to set up one or more insurance carriers related to the employer whereby the one or more insurance carriers will automatically be inserted under a payer of the patient that whose patient encounter is workman's compensation visit. At Step 358, a view request is received via the employer portal from the employer of the patient who generated the patient encounter a request to securely view the generated electronic patient medical record and the generated patient invoice generated from patient encounters to view services billed to the employer for employer provided health insurance or for the workman's compensation visits.

Method 350 is illustrated with one exemplary embodiment. However, the present invention is not limited to this embodiment and other embodiments can be used to practice the invention.

In such an exemplary embodiment at Step 352 a secure employer portal 332 is provided for selected patient encounter information via a second application 26', 28', 29', 30', 32', 33' on a server network device 20a, 20b, 20c with one or more processors via the cloud communications network 24.

At Step 354, protocol procedures are received via the employer portal 332 to set up a selected medical visit protocol based on employer preferences for patient encounters for patients who are employed by the employer.

At Step 356, insurance procedures are received via the employer portal 332 procedures to set up one or more insurance carriers related to the employer whereby the one or more insurance carriers will automatically be inserted under a payer of the patient that whose patient encounter is workman's compensation visit.

At Step 358, a view request is received via the employer portal 332 from the employer of the patient who generated the patient encounter a request to securely view the generated electronic patient medical record 252 and the generated patient invoice 75 generated from patient encounters to view services billed to the employer for employer provided health insurance or for the workman's compensation visits.

Wearable Network Devices

"Wearable mobile technology" and/or "wearable devices" are clothing and accessories incorporating computer and advanced electronic technologies. Wearable mobile network devices provide several advantages including, but not limited to: (1) Quicker access to notifications. Important and/or summary notifications are sent to alert a user to view a whole new message. (2) Heads-up information. Digital eye wear allows users to display relevant information like directions without having to constantly glance down; (3) Always-on Searches. Wearable devices provide always-on, hands-free searches; and (4) Recorded data and feedback. Wearable devices also take telemetric data recordings and providing useful feedback for users for exercise, health, fitness, activities etc.

Figure 33:
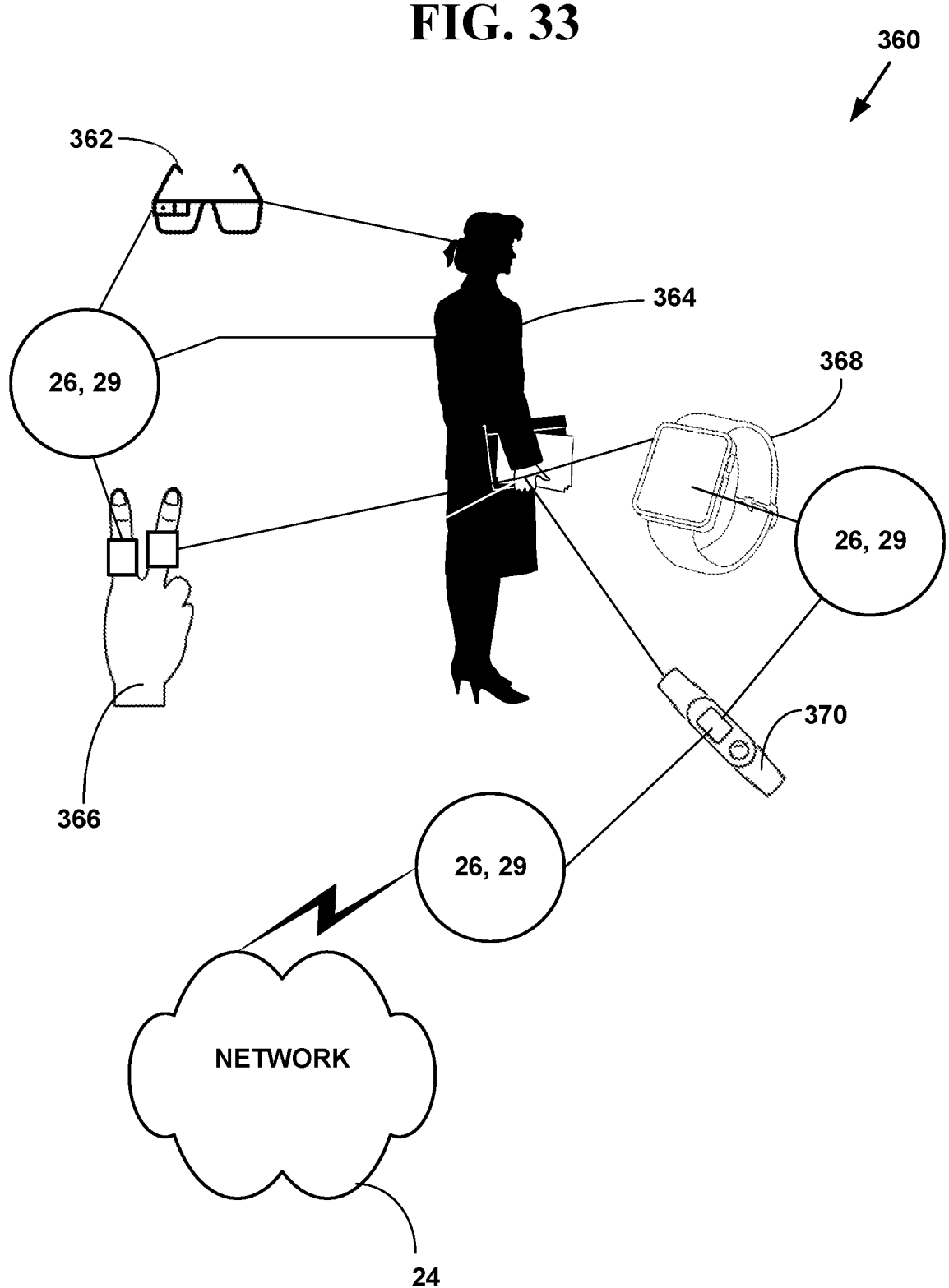
FIG. 33 is a block diagram illustrating wearable network devices.

FIG. 33 is a block diagram 360 illustrating wearable network devices used with the medical records system 10.

The wearable network devices include, but are not limited to, wearable digital glasses 362 (e.g., GOOGLE Glass, etc.), clothing 364 (e.g., smart headwear, smart lab coats, coats, tops and bottoms, shoes, etc.), jewelry 366 (e.g., smart rings, smart earrings, etc.), watches 368 (e.g., SONY, NIKE, SAMSUNG, NIKE, GARMIN, etc.) and/or wrist bands or fitness bands 370 (e.g. GARMIN, FITBIT, POLAR, NIKE, JAWBONE, LG, etc.). The wearable mobile devices includes an application 26 to communicate with the component of the medical records system 10 during a patient encounter and thereafter. All of the wearable devices 362, 364, 366, 368 and 370 have one or more processors, a non-transitory computer readable medium and/or selected ones have other components including, but not limited to, accelerometers, altimeters, music control, phone compatibility, etc. Both medical professionals and patients use such wearable devices to practice the invention. However, the present invention is not limited to such wearable devices and more, fewer and other types of wearable devices can also be used to practice the invention.

In one embodiment, the digital glasses 362 include a Heads Up Display (HUD) to display electronic information provided by the medical records system 10 including, but not limited to, the medical templates in FIGS. 2A-2B, FIGS. 17-22 and 35-37. However, the present invention is not limited to digital glasses 362 with a HUD or displaying medical templates, and other embodiments can be used to practice the invention.

Wearable devices and other network devices are becoming more popular and are also capable of displaying three dimensional (3D) electronic content for viewing. Most 3D displays create the illusion of depth by presenting a different image to each eye through 3D glasses such as "filtered lenses" and "active shutter glasses."

"Filtered lenses" 3D viewing creates an image where part goes to one eye and part to another, and part to both on a display on a network device 18.

"Autostereoscopic display" is another 3D method with one pixel or group of pixels has its light directed to one eye, and another group to the other on a network device 18.

Patient Tracking to Further Lower Patient Encounter Risks

As was described by Methods 334 and 342, a patient can schedule an appointment with and/or check into a medical facility via an electronic kiosk 326 or with a secure application 328 on a client network device 330. A patient can also schedule a virtual encounter with medical personnel at the medical facility via a communications network 24 and not actually physically enter the medical facility.

When a patient arrives at a medical facility or begins a new virtual encounter, it is important to track a patient's physical location in the medical facility and/or on-line location, a time a patient has arrived at the medial facility and/or has initiated the virtual encounter and/or other patient data that is collected and stored as patient tracking data. Tracking patients also helps to reduce additional medical risk factors associated with a patient encounter.

For example, if a patient entered a medical facility feeling dizzy, the patient may be having a stroke and/or heart attack or other serious medical issue and become incapacitated and/or may pass out somewhere in the medical facility and need immediate assistance. It is important to know when the patient has arrived at the medical facility, how long the patient has been waiting and a physical location of the patent in the medical facility or on-line during the actual patient encounter or virtual patient encounter. Such patient encounter information is stored in a Patient Tracking (PT) matrix. The PT matrix is used to create one or more additional patent tracking risk values that are integrated with the CX matrix and E/M matrix to further reduce complexities and risks associated with the actual or virtual patient encounter.

Figure 34:
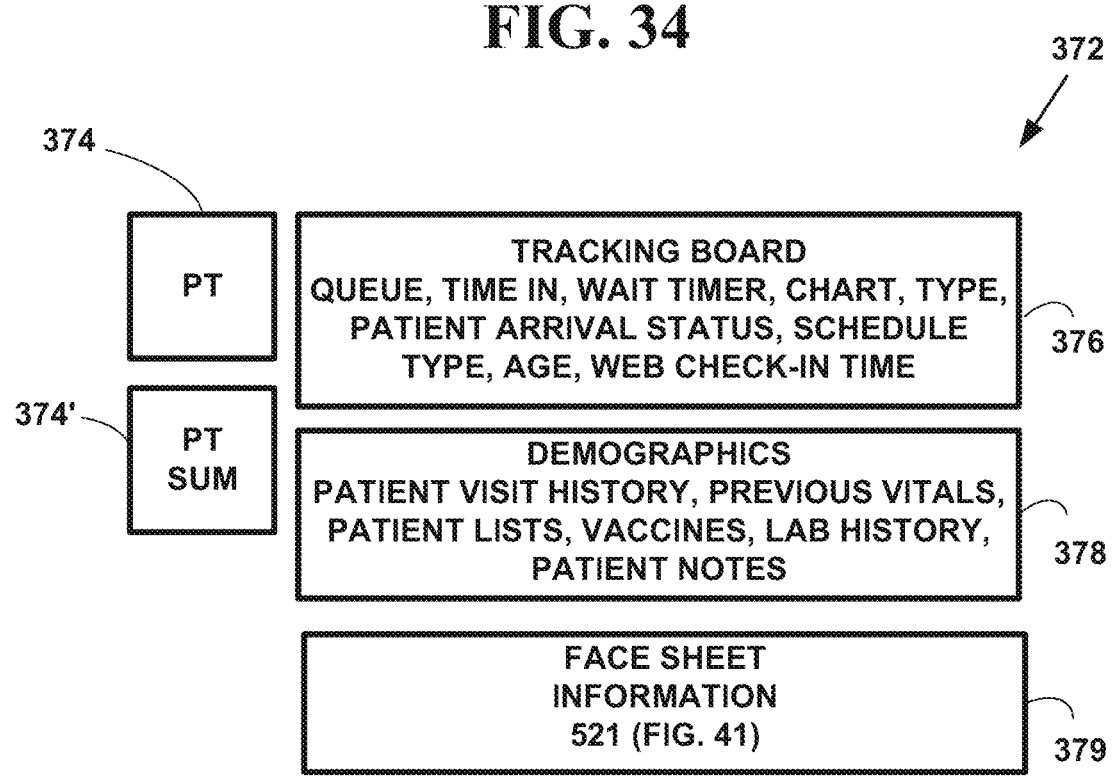
FIG. 34 is a block diagram illustrating a Patient Tracking (PT) matrix.

FIG. 34 is a block diagram illustrating an exemplary Patient Tracking (PT) Matrix 372. The PT matrix includes a Tracking Board component 376 a Patient Demographics component 378, and Face Sheet Information 379 (521, FIG. 41) each with unique plural fields.

Figure 35A:
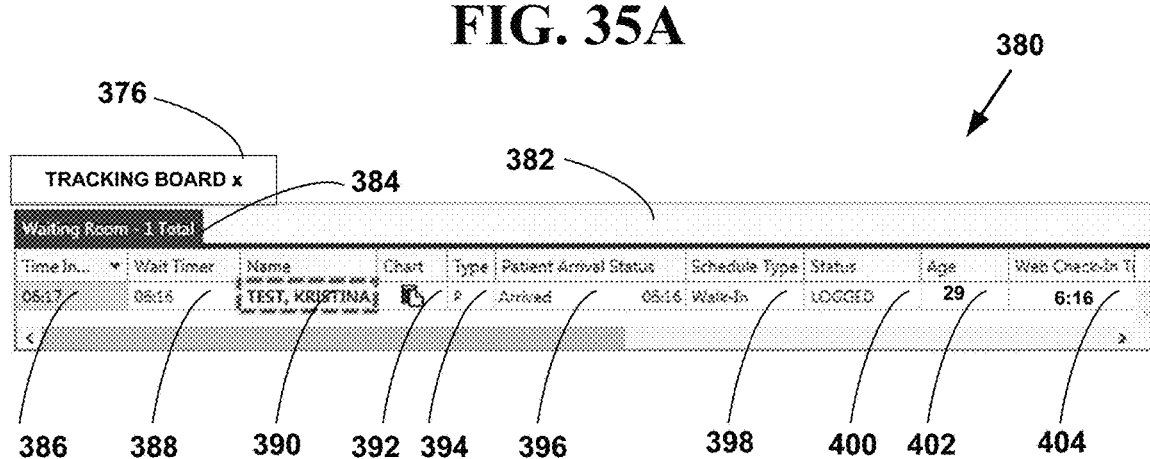
FIG. 35A is block diagram illustrating a Track Board component of the PT matrix.

FIG. 35A is block diagram 378 illustrating the Track Board component 376 of the PT matrix 372.

In one embodiment, the Tracking Board component 374 includes a graphical component 380 of the PT matrix 372, that includes, but is not limited to, plural fields including a Queue name 384, Time In 386, Wait Timer 388, Name 390, Chart 392, Type 394, Patient Arrival Status 396, Schedule Type 398, Status 400, Age 402, and/or Web/Kiosk Check-In Time 404 field. However, the present invention is not limited to the graphical component 380 described and more, fewer or other components and/or fields can be included on the Tracking Board 374 that is used to practice the invention.

Figure 37:
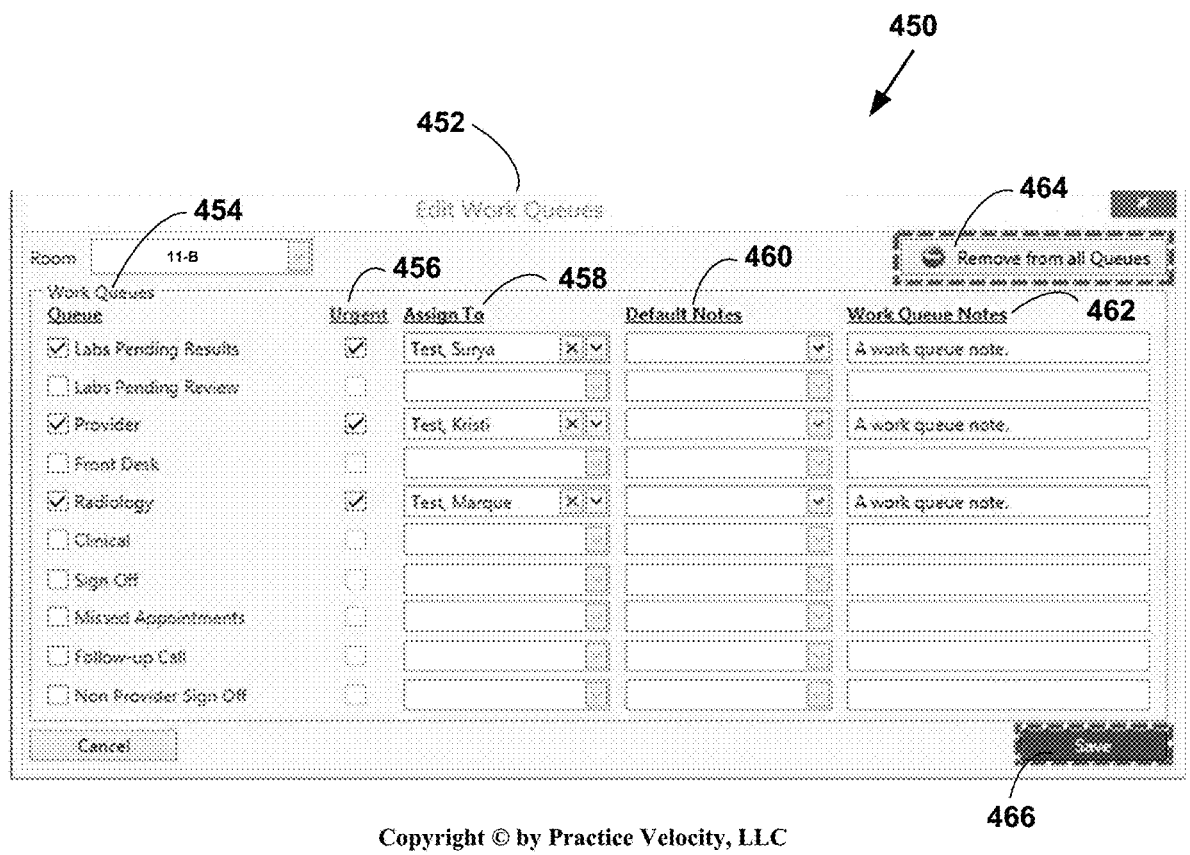

The Queue name field 384 includes where the patient is waiting or is physically located including, but not limited to, front desk, waiting room, lab, radiology, labs pending results, lab pending review, provider, clinical, sign out, follow up call, missed appointments, and/or non-provider sign off (see e.g., 454, FIG. 37, etc.) However, the present invention is not limited to such an embodiment and more, fewer and/or other Queue names can be used to practice the invention.

The Time In field 386 includes a clock time the patient has been waiting in the Queue 384 (e.g., 1 minute 6:17–6:16=1 minute, etc.)

The Wait Timer field 388 includes a clock time when the Wait Timer 388 was started (e.g., 6:16, etc.).

The Name field 390 includes the patent name (e.g., Kristina Test, etc.).

The Chart field 392 includes a graphical icon of chart with an electronic link to the patient's chart.

The Type field 394 includes a type of visit such as Private, Workmen's Comp, Occupational Medicine, etc. (e.g., P=Private, etc.).

The Patient Arrival Status field 396 includes an indication of whether the patient has arrive or not and the patient time of arrival (e.g., Arrived 6:16, etc.).

The Schedule Type field 398 includes, a type of visit such as walk in, scheduled appointment, etc. (e.g., Walk In, etc.).

The Status filed 400 includes an indication that a new patient encounter has been recorded on the medical records system 10 (e.g., Logged, etc.).

The Age field 402 includes the age of the patient (e.g., 29, etc.).

The Web/Kiosk Check-In Time 404 field includes a clock time the patient checked in via an application 378 on a client network device 380 via a network such as the Internet 24 or via an electronic kiosk 330.

In FIG. 35A, the patient checked in via the application 378 on the client network device 380 or via an electronic kiosk 330 instead of checking in at the front desk, etc.

Figure 35B:
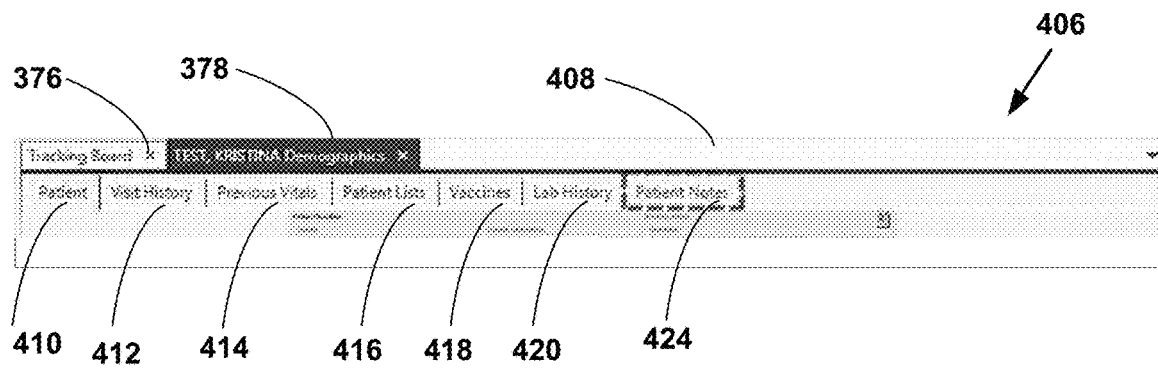
FIG. 35B is a block diagram illustrating a Patient Demographics component of the PT matrix.

FIG. 35B is a block diagram 406 a Patient Demographics 376 component of the PT matrix 374.

In one embodiment, the Patient Demographics 376 component includes a graphical component 408 of the PT matrix 372, that includes, but is not limited to, plural fields including a Patent Name field 410, Visit History field 412, Previous Vitals field 414, Patient Lists field 416, Vaccines field 418, Lab History field 420 and Patients Notes field 422. However, the present invention is not limited to the graphical component 408 described and more, fewer or other components and/or fields can be included on the Patient Demographics 376 component that is used to practice the invention.

The Patient Name field 410 includes a name of a patient (e.g., Kristina Test, etc.).

The Visit History field 412 includes previous visits by the patient to this medical facility and/or other related medical facility.

The Previous Vitals field 414 includes previous vital signs (e.g., temperature, blood pressure, pulse rate, respiration, etc.).

The Patient Lists field 416 includes a summary of all lists created for the patient during the current and previous patent encounter(s).

The Patient Vaccines field 418 includes a list of any vaccines previously given to the patient (e.g., flu, tetanus, etc.)

Lab History field 420 includes a list of all lab tests previously conducted on the patient (e.g., blood tests, urine tests, etc.)

Patients Notes field 422 includes a list of plurality of types of information collected and stored for the patient during the patient encounter.

Figure 36:
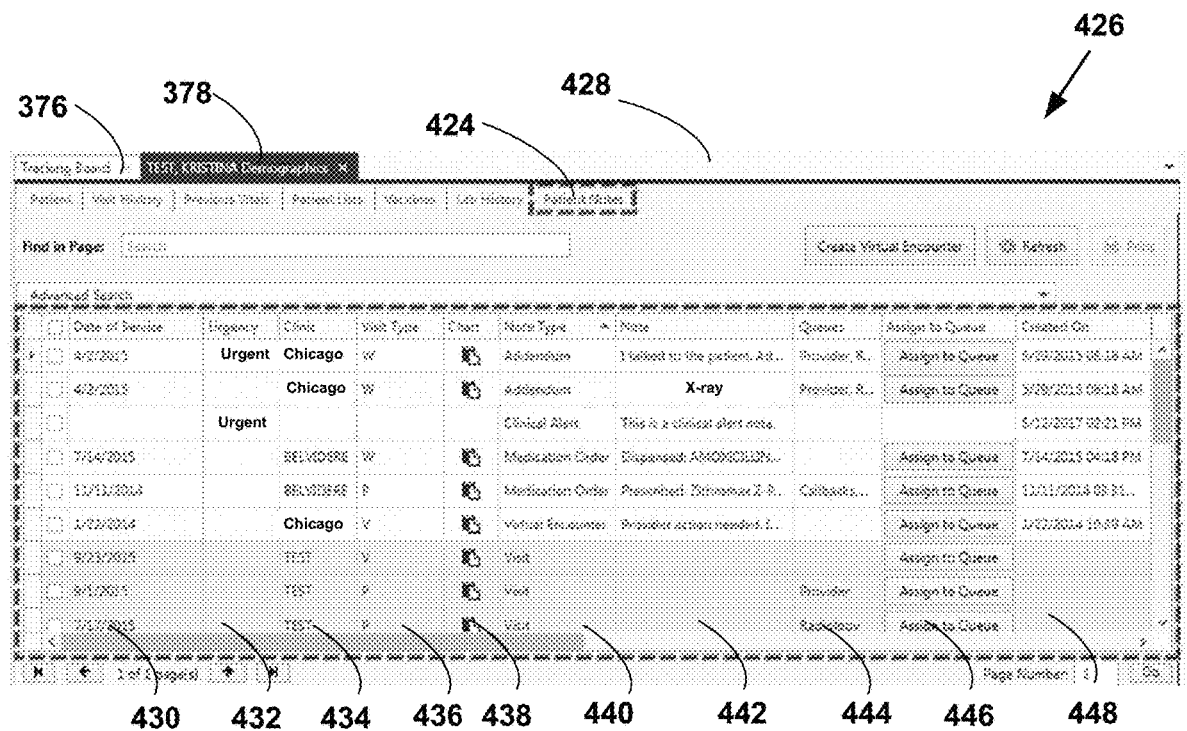

FIG. 36 is a block diagram illustrating a Patients Note field 422 from the Patient Demographics component 376 of the PT matrix 374.

In one embodiment, Patients Note field 422 component includes a graphical component 428, that includes, but is not limited to, plural sub-fields, including, but not limited to, Date of Service 430, Clinic 432, Visit Type 434, Chart 436, Note 438, Note Type 440, Note 442, Queues 444, Assigned to Queues 446 and/or Created On 448, sub-fields. However, the present invention is not limited to the sub-fields listed, and more fewer or other sub-fields can be used to practice the invention.

Exemplary Patients Note field 422 plural sub-fields 430-446 are illustrated in Table 12a. However, the present invention is not limited to these fields or sub-fields and more, fewer or other fields and sub-fields can be used to practice the invention. Selected ones of the plural sub-fields may not be visible on the graphical component 428 on the GUI (e.g., Created by User ID to Last Updated by User Description, etc.).

TABLE 12

| Name Of Sub-Field | Information in Sub-Field |
| --- | --- |
| Date of Service 430 | Date of the service for the patient note and/or visit entry. |

TABLE 12-continued

| Name Of Sub-Field | Information in Sub-Field |
| --- | --- |
| Urgency 432 | The note and/or visit urgency set in the Work Queue and/or Edit Work Queue pop-up window. |
| Clinic 434 | The clinic associated to the entry of the note and/or visit entry. |
| Visit Type 436 | Type of visit (Private (P), Workmen's Comp (WC), Emergency Physician Service (EPS), Virtual Encounter (VE), etc.). |
| Chart 438 | The chart icon to open a patient chart. |
| Note Type 440 | The type of patient note and/or visit entry (e.g., Account Note, Addendum, Billing Alert, Clinical Alert, Medication Order, Missed Appointment, System Log/Stamp, Virtual Encounter, Visit and/or Work Queue note). |
| Note 442 | The actual text transcription of the note and/or visit entry. |
| Queues 444 | The Work Queues assigned to the note and/or visit entry. |
| Assigned to Queue 446 | A button to display the Edit Work Queues pop-up window. |
| Created On 448 | The date of creation for the note and/or visit entry. |
| Created by User ID | The User ID who created the note and/or visit entry. |
| Created by User Description | The user description who create the note and/or visit entry. |
| Last Updated On | The date the note and/or visit entry was last updated. |
| Last Updated User Id | The user ID who last updated the note and/or visit entry. |
| Last Updated by User Description | The user description who last updated the note and/or visit entry. |

The Patient Notes feature that provides an historical account of all internal patient communications on a new Patient Notes tab 424 on the Patient Demographics page 378,428 on the GUI. The Patient Notes 424 feature provides users access to a single location to review all notes and visits associated to a patient.

To access patient notes and/or visits, the user clicks the Patient Notes 424 tab on the GUI. A chronological list of all notes and/or visits associated to a patient that have been documented in display in a Patient Notes graphical table 428.

The Patient Notes 424 tab highlights rows in a gray color if the Note Type is set to Visit to ensure awareness of visits that occurred in between patient notes. Details for actuals visits are not in the Patient Notes 424 tab but are visible in the Visit History 412 tab. Other types of notes such as Account Notes, Billing Alert, and Clinical Alerts do not display any information in the Date of Service and Visit Type columns via the Patient Notes 424 tab.

The Patient Notes 424 provides dynamic sorting, grouping, and filtering to allow users to customize the display of patients notes and/or visits information. The user right clicks the header of a column in the Patient Notes table and the following customization options display: (1) Sort Ascending, (2) Sort Descending, (3) Group By This Column, (4) Show Group Panel, (5) Show Column Chooser, (6) Best Fit, (7) Best Fit (all columns), and (8) Filter Editor. However, the present invention is not limited to these sorting, grouping, and filtering commands and more, fewer or other sorting, grouping, and filtering commands can be used to practice the invention.

FIG. 37 is a block diagram 450 illustrating an Edit Work Queues component 452.

The Assign to Queue 446 in the Patient Notes 424 allows users to assign and/or edit work queues directly from the Patient Notes 424. The user clicks the Assign to Queue 424 to display an Edit Work Queues 452 pop-up window.

Available user actions in the Edit Work Queues 452 pop-up window are illustrated in Table 12b. However, the present invention is not limited to such an embodiment and more, fewer or other user actions can be used to practice the inventions.

TABLE 12b

Queue 454: Assign a chart to a Work Queue(s) by clicking a Work Queue check box.
Urgent 456: Mark a chart as Urgent by clicking an Urgent check box.
Assign To 458: Assign a user to a chart by clicking the Assign To drop down menu.
Default Notes 460: Apply a default note to a chart by clicking the Default Notes drop down menu.
Work Queue Notes 462: Input a note for a chart by entering text in the Work Queue Notes text field.
Remove from all Queues 464: allows users to remove a chart 438 from all work queues 444, 454 assigned,
Save 466: The user clicks the green Save button to save changes performed in the Edit Work Queues 452 pop-up window.

Figure 38:
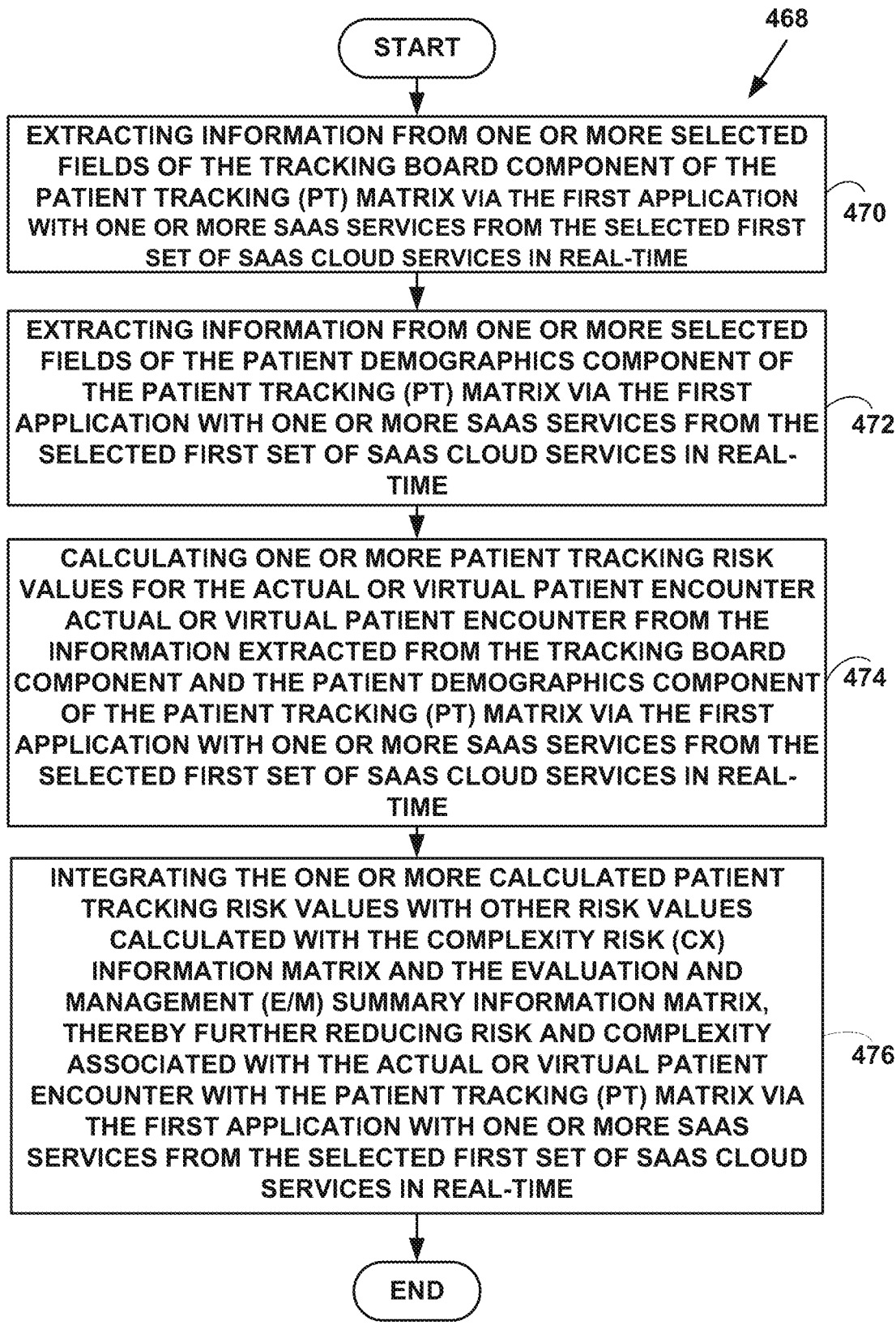
FIG. 38 is a flow diagram illustrating a method for automated processing of electronic medical records with cloud computing.

FIG. 38 is a flow diagram illustrating a Method 468 for automated processing of electronic medical records with cloud computing.

In FIG. 38 at Step 470, information is extracted from one or more selected fields of the Tracking Board component of the Patient Tracking (PT) matrix first application with one or more SaaS services from the selected first set of SaaS cloud services in real-time. At Step 472, information is extracted from one or more selected fields of the Patient Demographics component of the Patient Tracking (PT) matrix via the first application with one or more SaaS services from the selected first set of SaaS cloud services in real-time. At Step 474, one or more patient tracking risk values are calculated for the actual or virtual patient encounter from the information extracted from the Tracking Board component and the Patient Demographics component of the Patient Tracking (PT) matrix via the first application with one or more SaaS services from the selected first set of SaaS cloud services in real-time. At Step 476, the one or more calculated patient tracking risk values are integrated with other risk values calculated with the complexity risk (CX) information matrix and the Evaluation and Management (E/M) summary information matrix via the first application with one or more SaaS services from the selected first set of SaaS cloud services in real-time, thereby further reducing risk and complexity from the actual or virtual patient encounter.

Method 468 is illustrated with one exemplary embodiment. However, the present invention is not limited to this embodiment and other embodiments can be used to practice the invention.

In such an exemplary embodiment at Step 470, information is extracted from one or more selected fields of the Tracking Board component 376 of the Patient Tracking (PT) matrix 374 via the first application 26 with one or more SaaS services from the selected first set of SaaS cloud services 262 in real-time.

At Step 472, information is extracted from one or more selected fields of the Patient Demographics component 378 of the Patient Tracking (PT) matrix 374 via the first application 26 with one or more SaaS services from the selected first set of SaaS cloud services 262 in real-time.

At Step 474, one or more patient tracking risk values are calculated for the actual or virtual patient encounter from the information extracted from the Tracking Board component 376 and the Patient Demographics 378 component of the Patient Tracking (PT) matrix 374 via the first application 26 with one or more SaaS services from the selected first set of SaaS cloud services 262 in real-time.

At Step 476, the one or more calculated patient tracking risk value are integrated with other risk values calculated with the complexity risk (CX) information matrix 128 and the Evaluation and Management (E/M) summary information matrix 130, 132, via the first application 26 with one or more SaaS services from the selected first set of SaaS cloud services 262 in real-time, thereby further reducing risk and complexity from the actual or virtual patient encounter.

Method 468 and the Patient Tracking (PT) matrix 374 further reduce the risks and complexity associated with actual or virtual patient encounter.

The methods and system described herein help automate and reduce the risk and complexity of collecting patient encounter information electronically on client network devices and allow easy collection, processing and recording of medical information codes such as diagnosis codes, billing codes, insurance codes, etc. with cloud computing.

However, the present invention is not limited to cloud computing environments and the invention can also be practiced in a non-cloud computing environment. For example, the cloud storage objects can be replaced with non-transitory computer readable mediums, etc. The cloud services can be replaced with calls to APIs, processes running in a memory controlled by one or more processors, etc.

Medical Records Processing During Telemedicine Sessions

With the recent events including a global pandemic caused by the Covid-19 virus, telemedicine is becoming increasingly important.

"Telemedicine" includes remote virtual clinical medical services, such as diagnosis and monitoring. When a global pandemic, rural and urban settings, lack of transport, lack of mobility, decreased funding, increase in technology bandwidth (e.g., 5G bandwidth speeds etc.) and/or a lack of medical staff restrict access to care, telemedicine bridges the patient care gap as well as providing patient distance-learning, audio and video meetings, supervision, online information and health data management and healthcare system integration.

FIGS. 39A, 39B, 39C, 39D, 39E and 39F are a flow diagram illustrating a Method 478 for automated processing of electronic medical records with telemedicine.

In FIG. 39A and Method 478 at Step 480, plural cloud server network devices each with a telemedicine application and one or more processors on a cloud communications network, create plural pooled cloud hardware resources comprising: (1) automatic provisioning of plural pooled cloud hardware resources usable in any amount at any time as needed and available via plural cloud broadband network access components on the plural cloud server network devices; (2) automatic scaling of the plural pooled cloud hardware resources to obtain and release one or more of the plural pooled cloud hardware resources as required; (3) automatic controlling and optimizing the plural pooled cloud hardware resources with a metering method; (4) plural cloud software services for automated processing of medical information including a cloud Platform as a Service (PaaS), a cloud computing Infrastructure as a Service (IaaS), and plural available cloud Software services as a Service (SaaS) including a plural different software services for automated risk reduction in processing of medical records information after virtual patient encounters via telemedicine visits, the plural cloud software services for automated processing of medical information comprising: cloud networking services, storage services, virtualization services, operating system services, run-time services, data services and application services executed with the plural pooled cloud hardware resources. At Step 482, a first telemedicine application on a first cloud network device with one or more processor receives a request for a telemedicine visit and virtual patient encounter from a client telemedicine application on a client network device with one or more client network device processors. In FIG. 39B at Step 484, one or more balancing methods are applied in real-time on the first telemedicine application on the first cloud server network device creating a balancing selection including: (1) balancing telemedicine visit workflow across the plural other telemedicine applications on the plural cloud server network devices and across the plural pooled cloud hardware resources and the plural cloud software services, and (2) balancing telemedicine patient load across plural medical facilities including an availability of plural medical personnel at the plural medical facilities and a current actual patient load and current telemedicine patient load at the plural medical facilities. At Step 486, the first telemedicine application on the first cloud server network device selects with the balancing selection from the one or more balancing methods a selected telemedicine application on a selected cloud server network device to accept the request for the telemedicine visit and the virtual patient encounter. At Step 488, a selection message is sent from the first telemedicine application on the first cloud server network device via the cloud communications network to the selected telemedicine application on the selected cloud server network device indicating the selected telemedicine application on the selected cloud server network device has been selected to accept the telemedicine visit and the virtual patient encounter. In FIG. 39C at Step 490, the selected telemedicine application on the selected cloud server network device selects a PaaS and an IaaS provided by the plural pooled cloud hardware resources on the cloud communications network. At Step 492, the selected telemedicine application on the selected cloud server network device selects via the cloud communications network a first set of SaaS cloud services from the plural available cloud SaaS services for automated electronic medical records processing including reducing risk and reducing a number of possible diagnostic decisions when processing medical records from the virtual patient encounter via the telemedicine visit. At Step 494, the selected telemedicine application on the selected cloud server network device selects via the cloud communications network, one or more SaaS services from the selected first set of SaaS cloud services, plural individual data structures comprising a plural medical information matrixes including a patient tracking (PT) matrix, historical information (HX) matrix, patient examination (PX) matrix, complexity risk (CX) information matrix and an Evaluation and Management (E/M) summary information matrix, each with plural unique matrix information fields, the plural individual data structures stored in one or more cloud storage objects on the cloud communications network and available to first set of SaaS cloud services selected by the selected telemedicine application on the selected cloud server network device. In FIG. 39D Step 496, data is securely collected on the selected telemedicine application on the selected cloud server network device via the cloud communications network from the client telemedicine application on the client network device for the virtual patient encounter during the telemedicine visit into plural of data fields on one or more different electronic medical templates with one or more SaaS services from the selected first set of SaaS cloud services. At Step 498, the selected telemedicine application on the selected cloud server network device aggregates with one or more SaaS services from the selected first set of SaaS cloud services in real-time only selected ones of data items from the plural data fields from the one or more different electronic medical templates storing the collected virtual patient encounter data from the telemedicine visit into the plural information matrixes stored in the one or more cloud storage objects, the plural information matrixes including: the patient tracking (PT) matrix, historical information (HX) matrix, patient examination (PX) matrix, complexity risk (CX) information matrix and the Evaluation and Management (E/M) summary information matrix, each with the plural unique matrix information data fields. At Step 500, the selected telemedicine application on the selected cloud server network device via the cloud communications network eliminates with one or more SaaS services from the selected first set of SaaS cloud services with the only selected ones of data items aggregated into the plural information matrixes an amount and complexity of the virtual patient encounter data from the telemedicine visit collected to be reviewed during the virtual patient encounter from the telemedicine visit. In FIG. 29E at Step 502, the selected telemedicine application on the selected cloud server network device via the cloud communications network with one or more SaaS services from the selected first set of SaaS cloud services with the selected data items aggregated into the plural information matrixes reduces a number of diagnostic options to be considered during the virtual patient encounter via the telemedicine visit, thereby reducing a medical risk associated with making a complex medical decision for the virtual patient encounter via the telemedicine visit and limiting an amount and complexity of patient data to be processed and reviewed after the virtual patient encounter via the telemedicine visit. At Step 504, the selected telemedicine application on the selected cloud server network device via the cloud communications network with one or more SaaS services from the selected first set of SaaS cloud services calculates in real-time plural matrix summary values from the plural information matrixes. At Step 506, the selected telemedicine application on the selected cloud server network device via the cloud communications network with one or more SaaS services from the selected first set of SaaS cloud services calculates in real-time one or more medical and billing codes using the calculated plural matrix summary values. In FIG. 39F at Step 508, the selected telemedicine application on the selected cloud server network device via the cloud communications network with one or more SaaS services from the selected first set of SaaS cloud services generates automatically in real-time an electronic patient medical record with a plural data fields from the calculated plural matrix summary values and the one or more calculated medical and billing codes. At Step 510, the selected telemedicine application on the selected cloud server network device via the cloud communications network with one or more SaaS services from the selected first set of SaaS cloud services generates automatically in real-time a patient invoice for the virtual patient encounter via the telemedicine visit from the generated electronic medical record. At Step 512, the selected telemedicine application on the selected cloud server network device via the cloud communications network with one or more SaaS services from the selected first set of SaaS cloud services displays securely in real-time on the selected cloud server network device on a display component via a graphical user interface (GUI) selected ones of the plural data fields from the generated electronic patient medical record, including complexity risk information for the virtual patient encounter via the telemedicine visit and the generated patient invoice. The generated electronic medical record provides a three hundred-sixty degree view of medical, billing, insurance and other information collected and generated from the virtual patient encounter via the telemedicine visit. Displaying the three hundred sixty degree view comprises displaying medical, billing, insurance and other information on the GUI surrounding a patient avatar for the virtual patient encounter via the telemedicine visit.

Method 478 is illustrated with one exemplary embodiment. However, the present invention is not limited to this embodiment and other embodiments can be used to practice the invention.

In such an exemplary embodiment in FIG. 39A at Step 480, plural cloud server network devices 20a, 20b, 20c each with a telemedicine application 29' and one or more processors on a cloud communications network 24, create plural pooled cloud hardware resources comprising: (1) automatic provisioning of plural pooled cloud hardware resources usable in any amount at any time as needed and available via plural cloud broadband network access components on the plural cloud server network devices 20a, 20b, 20c; (2) automatic scaling of the plural pooled cloud hardware resources to obtain and release one or more of the plural pooled cloud hardware resources as required; (3) automatic controlling and optimizing the plural pooled cloud hardware resources with a metering method; (4) plural cloud software services 262 (FIG. 24) for automated processing of medical information including a cloud Platform as a Service (PaaS) 270, a cloud computing Infrastructure as a Service (IaaS) 266, and plural available cloud Software services as a Service (SaaS) 262 including a plural different software services for automated risk reduction in processing of medical records information after virtual patient encounters via telemedicine visits, the plural cloud software services 262 for automated processing of medical information comprising: cloud networking services, storage services, virtualization services, operating system services, run-time services, data services and application services executed with the plural pooled cloud hardware resources.

At Step 482, a first telemedicine application 29' on a first cloud network device 20a with one or more processor receives a request for a telemedicine visit and virtual patient encounter from a client telemedicine application 29 on a client network device 18 with one or more client network device processors.

In FIG. 39B at Step 484, one or more balancing methods are applied in real-time on the first telemedicine application 29'a on the first cloud server network device 20a creating a balancing selection including: (1) balancing telemedicine visit workflow across the plural other 29'b, 29'c telemedicine applications on the plural other cloud server network devices 20b, 20c and across the plural pooled cloud hardware resources 266, 270 and the plural cloud software services 262, and (2) balancing telemedicine patient load across plural medical facilities including an availability of plural medical personnel at the plural medical facilities and a current actual patient load and current telemedicine patient load at the plural medical facilities.

For example, one exemplary balancing method at Step 484 (1) will balance, available cloud bandwidth, processing time, storage capacity, etc. across the plural other 29'b, 29'c telemedicine applications on the plural other cloud server network devices 20b, 20c and across the plural pooled cloud hardware resources 266, 270 and the plural cloud software services 262. Cloud bursting is used to balance loads between clouds. However, the present invention is not limited to such cloud resource balancing methods and other methods can be used to practice the invention.

In one exemplary embodiment at Step 484, an Artificial Intelligence (AI) application on the SaaS 262 balances in real-time cloud resources and/or telemedicine patient load across plural medical facilities by analyzing via one or more AI methods on an AI application, with a dynamic Big Data set collected and stored in one or more cloud storage objects 282 and with plural Big Data set analytic methods. In one embodiment, SaaS 262 includes an AI application. In another embodiment, the AI application is a standalone application. However, the present invention is not limited to such an embodiment, and the AI application can be provided in other than the SaaS 262.

"Artificial intelligence" (AI), also known as machine intelligence (MI), is intelligence demonstrated by machines, in contrast to the natural intelligence (NI) displayed by humans and other animals. AI research is defined as the study of "intelligent agents." Intelligent agents are any software application or hardware device that perceives its environment and takes actions that maximize its chance of successfully achieving its goals. Colloquially, the term "artificial intelligence" is applied when a machine mimics "cognitive" functions that humans associate with human brains, such as learning, problem solving and comparing large number of data points.

"Big Data" refers to the use of predictive analytic methods that extract value from data, and to a particular size of a data set. The quantities of data used are very large and typically 500,000 to 1 Million+ data points. Analysis of Big Data sets are used to find new correlations and to spot trends.

In one embodiment, the one or more AI methods include, but are not limited to knowledge-based systems for time series analyses, in particular AI methods for eliminating variations in telemedicine patient load used to collect telemedicine patient load in statistical studies, and for multivariate tabular analysis. However, the present invention is not limited to such embodiments and more, fewer and/or other AI methods and/or other non-AI methods for balancing can be used to practice the invention.

Multivariate tabular analysis (MVA) involves observation and analysis of more than one statistical outcome variable at a time using tables of data. In design and analysis, the technique is used to perform studies across multiple dimensions while taking into account the effects of all variables on the responses of interest.

In one embodiment, telemedicine patient load created by the SaaS 262 and/or the AI application on the SaaS 262 include "weighted" and "normalized" telemedicine patient load values. The weighting and normalizing techniques applied to the data provide telemedicine patient load values that are more accurate and less subject to data anomalies. The weighting and normalizing also provide in part, device-independent and medical facility-independent telemedicine patient load values. However, the present invention is not limited to this embodiment and other types of telemedicine patient load values can be used to practice the invention.

A "weighted" variable provides a value (i.e., the weight, etc.) for each observation in a data set. The $i^{th}$ weight value, $w_i$, is a weight for the $i^{th}$ observation. For most applications, a valid weight is nonnegative. A zero weight usually indicates the observation is excluded from the analysis. Observations that have relatively large weights have more influence in the data analysis than observations that have smaller weights. An unweighted analysis is the same as a weighted analysis in which all weights are equal to one.

A "normalization" of data refers to the creation of shifted and scaled versions of data values, where the intention is that these normalized data values allow the comparison of corresponding normalized values for different datasets in a way that eliminates effects of certain gross influences, such as those created by anomalies. An "anomaly" is a deviation in a quantity from an expected value (e.g., a difference between a measurement and a mean and/or a model prediction). Similarly, a standardized anomaly equals an anomaly divided by a standard deviation.

However, the present invention is not limited to these embodiments and other balancing methods with and/or without AI and/or with and/or without Big Data can be used to practice the invention.

For example, one exemplary AI balancing method at Step 484 (2) will balance urgent care clinic 1 has ten actual patients and five telemedicine patients and have availability for three more telemedicine patients, urgent care clinic 2 has one actual patients and zero telemedicine patients and have availability for fifteen more telemedicine patients, hospital emergency room 1 has seven actual patients, seven telemedicine patients and have ability for twenty-five more telemedicine patients, etc. to select a medical facility, etc. The medical personnel include, but are not limited to, doctors, nurses, physician assistants, nurse practitioners, etc.

At Step 486, the first telemedicine application 29'a on the first cloud server network device 20a selects with the balancing selection from the one or more balancing methods a selected telemedicine application 29'b on a selected cloud server network device 20b to accept the request for the telemedicine visit and the virtual patient encounter.

At Step 488, a selection message is sent from the first telemedicine application 29'a on the first cloud server network device 20a via the cloud communications network 24 to the selected telemedicine application 29'b on the selected cloud server network device 20b indicating the selected telemedicine application 29'b on the selected cloud server network device 20b has been selected to accept the telemedicine visit and the virtual patient encounter.

In FIG. 39C at Step 490, the selected telemedicine application 29'b on the selected cloud server network device 20b selects a PaaS 270 and an IaaS 266 provided by the plural pooled cloud hardware resources on the cloud communications network 24.

At Step 492, the selected telemedicine application 29'b on the selected cloud server network device 20b selects via the cloud communications network 24 a first set of SaaS cloud services 262 from the plural available cloud SaaS services 262 for automated electronic medical records processing including reducing risk and reducing a number of possible diagnostic decisions when processing medical records from the virtual patient encounter via the telemedicine visit.

At Step 494, the selected telemedicine application 29'b on the selected cloud server network device 20b selects via the cloud communications network 24, one or more SaaS services 262' from the selected first set of SaaS cloud services 262, plural individual data structures comprising a plural medical information matrixes including a patient tracking (PT) matrix 374, historical information (HX) matrix 124, patient examination (PX) matrix 126, complexity risk (CX) information matrix 128 and an Evaluation and Management (E/M) summary information matrix 130, 132, each with plural unique matrix information fields, the plural individual data structures stored in one or more cloud storage objects 282 on the cloud communications network 24 and available to first set of SaaS cloud services 262' selected by the selected telemedicine application 29'*b* on the selected cloud server network device 29*b*.

In FIG. 39D Step 496, data is securely collected on the selected telemedicine application 29'*b* on the selected cloud server network device 20*b* via the cloud communications network 24 from the client telemedicine application on the client network device for the virtual patient encounter during the telemedicine visit into plural of data fields on one or more different electronic medical templates 124, 126, 128, 130, 132, 374 with one or more SaaS services 262' from the selected first set of SaaS cloud services 262. The data is securely collected using any the encryption and/or security methods described herein.

In on embodiment, the data is securely collected on the selected telemedicine application 29'*b* with proprietary, PRACTICE VELOCITY, EXPERITY, etc. or publically available audio-visual program such as ZOOM, SKYPE, GOOGLE MEET, MICROSOFT TEAMS, etc. The data is securely collected and then securely stored to comply with HIPAA patient privacy rules and regulations.

At Step 498, the selected telemedicine application 29'*b* on the selected cloud server network device 20*b* aggregates with one or more SaaS services 262' from the selected first set of SaaS cloud services 262 in real-time only selected ones of data items from the plural data fields from the one or more different electronic medical templates storing the collected virtual patient encounter data from the telemedicine visit into the plural information matrixes stored in the one or more cloud storage objects 282 (FIG. 25) the plural information matrixes including: the patient tracking (PT) matrix 374, historical information (HX) matrix 124, patient examination (PX) matrix 126, complexity risk (CX) information matrix 128 and the Evaluation and Management (E/M) summary information matrix 130, 132, each with the plural unique matrix information data fields (FIG. 8-12).

At Step 500, the selected telemedicine application 29'*b* on the selected cloud server network device 20*b* via the cloud communications network 24 eliminates with one or more SaaS services 262' from the selected first set of SaaS cloud services 262 with the only selected ones of data items aggregated into the plural information matrixes 124, 126, 128, 130, 132, 374 an amount and complexity of the virtual patient encounter data from the telemedicine visit collected to be reviewed during the virtual patient encounter from the telemedicine visit.

In FIG. 39E at Step 502, the selected telemedicine application 29*b*' on the selected cloud server network device 20*b* via the cloud communications network 24 with one or more SaaS services 262' from the selected first set of SaaS cloud services 262 with the selected data items aggregated into the plural information matrixes 124, 126, 128, 130, 132, 374 reduces a number of diagnostic options to be considered during the virtual patient encounter via the telemedicine visit, thereby reducing a medical risk associated with making a complex medical decision for the virtual patient encounter via the telemedicine visit and limiting an amount and complexity of patient data to be processed and reviewed after the virtual patient encounter via the telemedicine visit.

At Step 504, the selected telemedicine application 29'*b* on the selected cloud server network device 20*b* via the cloud communications network 24 with one or more SaaS services 262' from the selected first set of SaaS cloud services 262 calculates in real-time plural matrix summary values 124', 126', 128', 130', 132' (FIG. 21) 374' (FIG. 34) from the plural information matrixes 124, 126, 128, 130, 132, 374 (FIG. 34).

Step 506, the selected telemedicine application 29'*b* on the selected cloud server network device 20*b* via the cloud communications network 24 with one or more SaaS services 262' from the selected first set of SaaS cloud services 262 calculates in real-time one or more medical and billing codes 247 using the calculated plural matrix summary values 124', 126', 128', 130', 132', 374'.

In FIG. 39F at Step 508, the selected telemedicine application 29'*b* on the selected cloud server network device 20*b* via the cloud communications network 24 with one or more SaaS services 262' from the selected first set of SaaS cloud services 262 generates automatically in real-time an electronic patient medical record 252 (FIG. 22) with a plural data fields from the calculated plural matrix summary values 124', 126', 128', 130', 132', 372' and the one or more calculated medical and billing codes 247.

At Step 510, the selected telemedicine application 29*b*' on the selected cloud server network device 20*b* via the cloud communications network 24 with one or more SaaS services 262' from the selected first set of SaaS cloud services 262 generates automatically in real-time a patient invoice 75 (FIG. 4) for the virtual patient encounter via the telemedicine visit from the generated electronic medical record 252.

At Step 512, the selected telemedicine application 29'*b* on the selected cloud server network device 20*b* via the cloud communications network 24 with one or more SaaS services 262' from the selected first set of SaaS cloud services 262 displays securely in real-time on the selected cloud server network device 20*b* on a display component via a graphical user interface (GUI) 77,99 (FIG. 15) selected ones of the plural data fields from the generated electronic patient medical record 252, including complexity risk information for the virtual patient encounter via the telemedicine visit and the generated patient invoice 75. The generated electronic medical record 252 provides a three hundred-sixty degree view of medical, billing, insurance and other information collected and generated from the virtual patient encounter via the telemedicine visit. Displaying the three hundred sixty degree view comprises displaying medical, billing, insurance and other information on the GUI surrounding a patient avatar 199 for the virtual patient encounter via the telemedicine visit. The information is securely displayed using any the encryption and/or security methods described herein.

Figure 40:
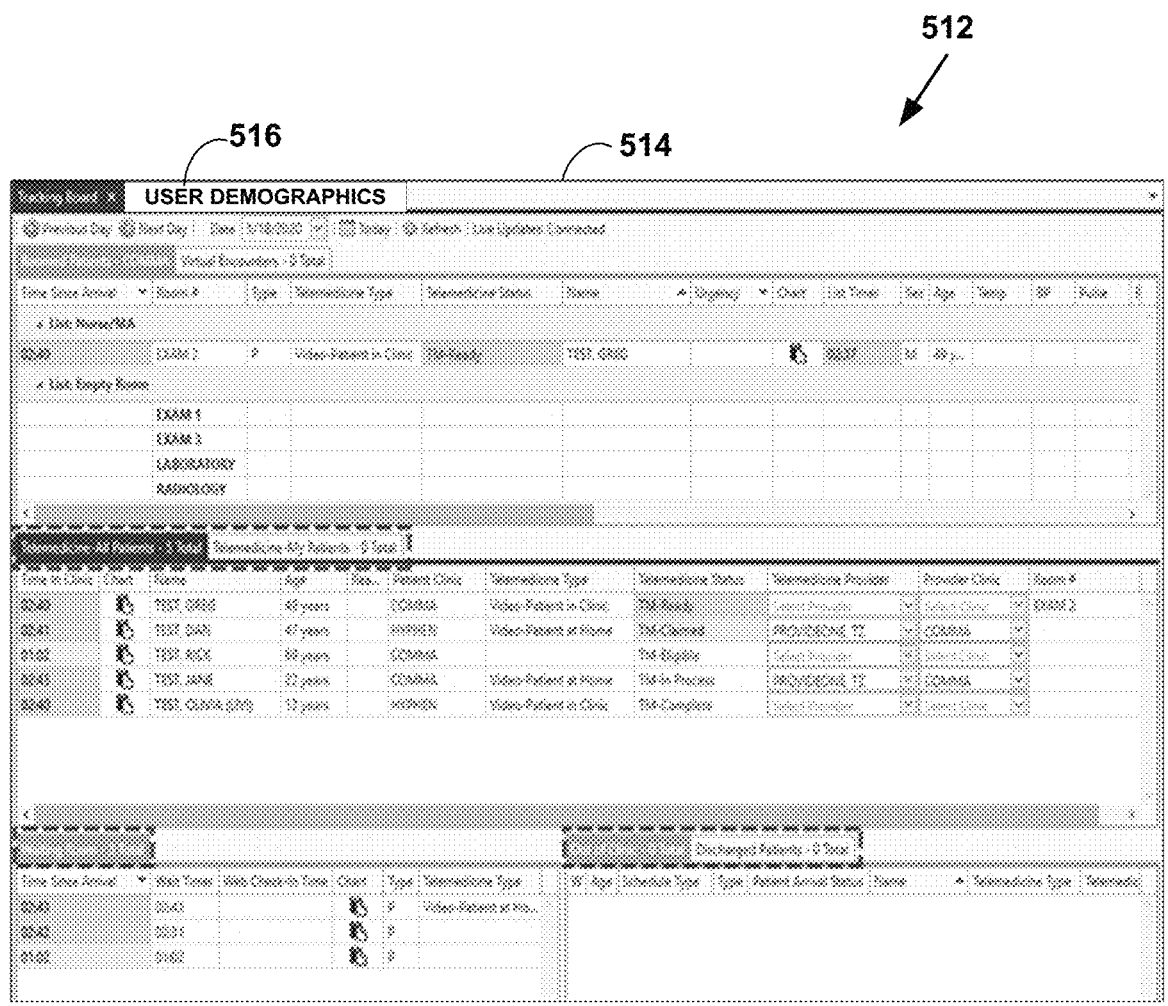
FIGS. 40 and 42 are copyright © by Practice Velocity, LLC. All rights reserved.

FIG. 40 is a block diagram 512 illustrating an exemplary telemedicine patient tracking board 376, 514 generated by the telemedicine applications 29'*a*, 29'*b*, 29'*c* on the cloud server network device 20*a*, 20*b*, 20*c*. However, the present invention is not limited to such an embodiment and other tracking boards with other display screen layouts can be used to practice the invention.

In one embodiment, information on the exemplary telemedicine patient tracking board 376, 514 is displayed on a cloud server network devices 20*a*, 20*b*, 20*c* only after the balancing method at Step 494 is applied. However, the present invention is not limited to such an embodiment and other embodiments with other types of telemedicine patient tracking boards that do not use a balancing method can be used to practice the invention.

Figure 41:
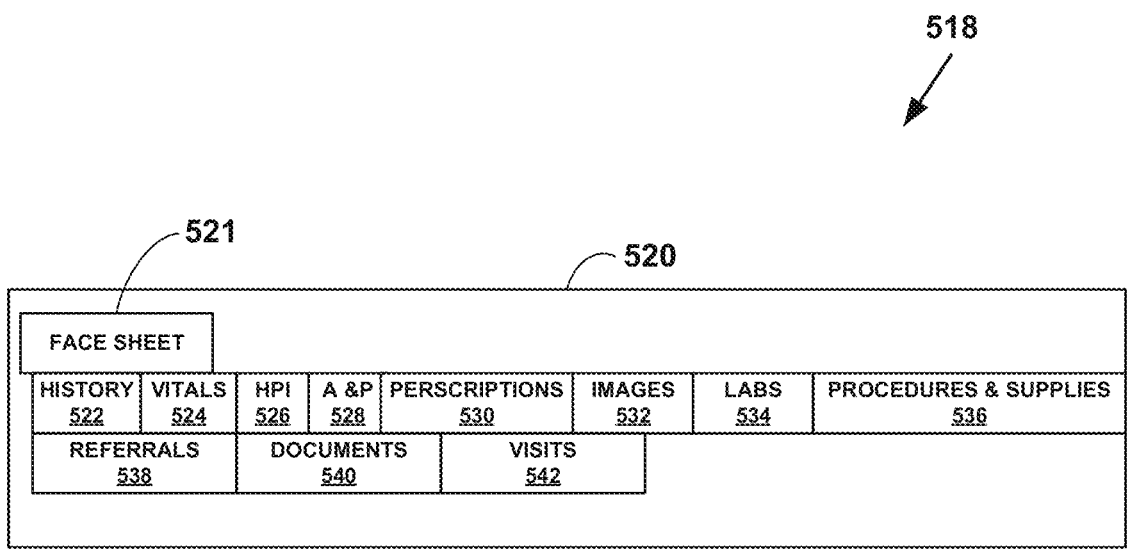
FIG. 41 is a block diagram illustrating an exemplary telemedicine Face tab screen with graphical Face Sheet tab selectable by a user.

FIG. 41 is a block diagram 518 illustrating an exemplary telemedicine Face Sheet tab 521 screen with graphical Face Sheet tab 522 selectable by a user. However, the present invention is not limited to such an embodiment and other digital information sheets with other display screen layouts can be used to practice the invention.

In one embodiment, the patient tracking board 376, 514 further includes a Demographics component tab 516. When a user navigates to the Patient Demographics tab 516, a new Face Sheet tab 521 is displayed.

When the Face Sheet tab 521 is activated, plural additional graphical screens displays, information including but not limited to: (1) a telemedicine patient's visit history section 522; (2) the patient's medical vitals section 524 (e.g., temperature, blood pressure, pulse, height, weight, etc.) information for each of the patient's visits. In addition, additional vitals are recorded specific to female patients including but not limited to, menses, menopause, pregnancy, and/or breastfeeding and for children additional vitals include, but are not limited to, head and chest circumference; (3) the patient's History of the Present Illness (HPI) section 526 that includes the telemedicine visit's complaint information. Details from the visit and follow up complaints are displayed in a bulleted list. Any related abnormal symptoms documented are also displayed. The HPI includes a Chronic Problem Management feature, the HPI panel displays the summary narrative that includes the patient's first name, last name, age, sex, and active chronic problems. If the Wellness Visit indicator is selected in the chart, information displays in a Wellness Visit section. Details from the visit and follow up complaints display in a bulleted list in a Complaint section; (4) a Plan section 528 displays plan information from an Anatomy & Physiology (A&P) tab of the telemedicine visit's chart. A Disposition, Additional Notes, and Referral Information are displayed in a bulleted list; (5) a Prescriptions section 530 display indicates a number of medications prescribed during the telemedicine visit; (6) an Imaging section 532 indicates a number and type of x-rays and other scans such as an ultra sound, Magnetic Resonance Imaging (MRI), etc. the patient may have had during a previous visit. Links to the x-rays and scans allow displays of the x-rays and scans; (7) a Labs section 534 displays previous laboratory tests (e.g., complete blood count (CBC), liver function test (LFT), basic metabolic panel (e.g., CHEM-7. etc.), kidney tests such as CR (Albumin to Creatinine Ratio) and GFR (glomerular filtration rate), etc. completed on the patient; (8) a Procedures and Supplies section 536 displays the procedures or supplies ordered during the telemedicine visit; (8) a Referrals 538 section 538 lists referrals ordered during the telemedicine visit, including but not limited to referral category (e.g., obstetrics and gynecology, etc.), sub category (e.g., pregnancy), facility (e.g., office, clinic, hospital, etc.) or provider, and phone number for a referral; (9) A Documents 540 section includes all documents generated for the telemedicine visit; (10) A Visits section 542 allows filtering the patients visits from the Last 6 Months, Last 12 Months, Last 18 Months or All visits. The Visits tab includes the patient's date of service (DOS), type of visit, provider who signed the chart, diagnosis description, orders (e.g., (medication, labs, imaging, supplies, procedures, vaccines, etc.), diagnosis codes (e.g. ICD9, ICD10, SNOMED, etc.) that correspond to the diagnosis, CPT codes that corresponds to the orders and/or a clinic, a medical facility that provided the telemedicine visit. However, the present invention is not limited to this embodiment and more, fewer or other information can be used on the Face Sheet.

The Face Sheet tab 520 information is described herein as being use for telemedicine visits. However, the Face Sheet tab 520 information is also used for actual in-person visits to a medical facility wherein fields such as the Prescriptions 530 information, includes new actual prescriptions given directly to the user, the Images 532 information includes new images order for the patient, the Procedures 534 information including new procedures actually performed on the patient (e.g., stitches, casts, surgeries, etc.).

The order of the fields in generated when the Face Sheet tab 520 is activated as is illustrated in FIG. 41 and is exemplary only. However other display screen orders and more fewer and other information fields can be displayed to practice the invention.

Figure 42:
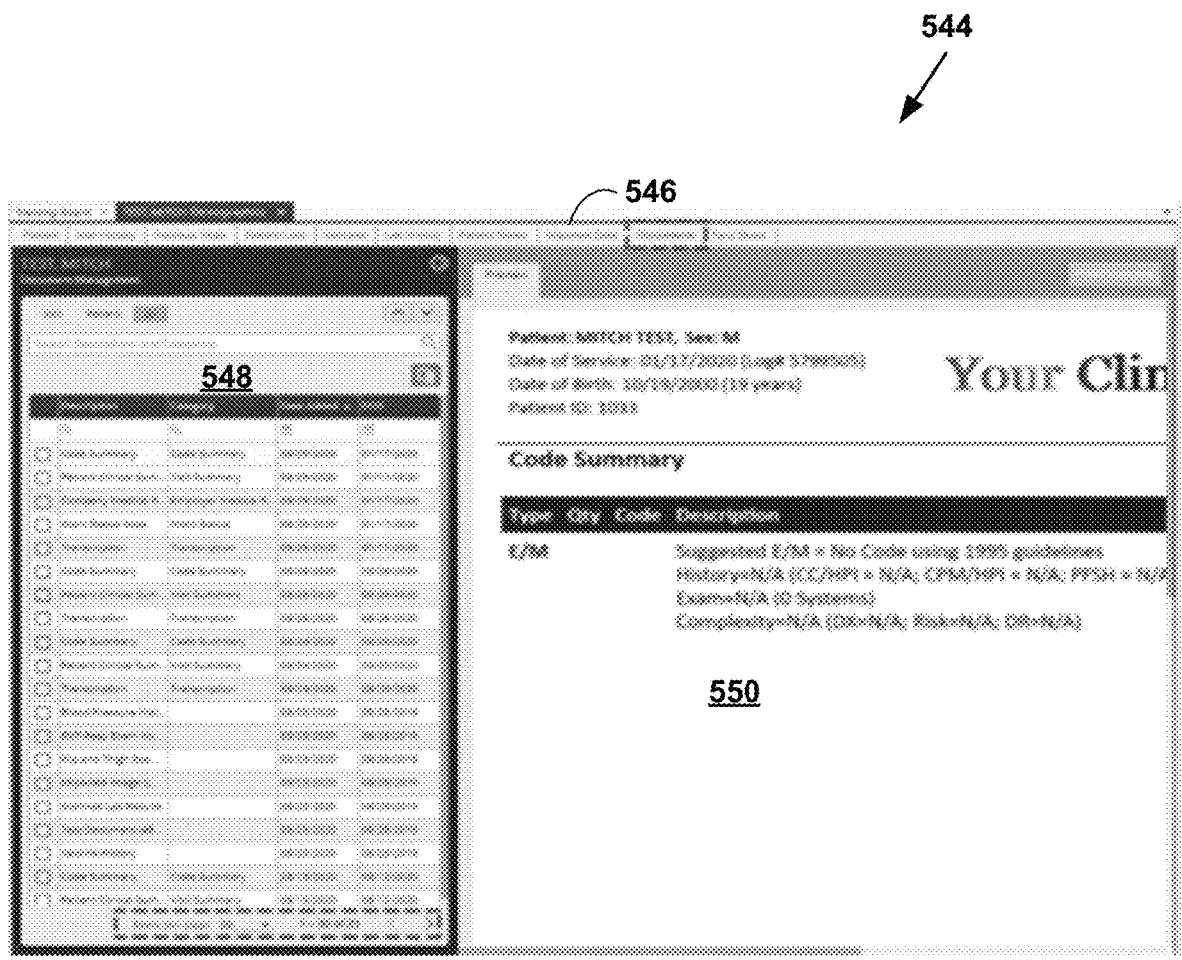

FIG. 42 is a block diagram 544 illustrating an exemplary telemedicine Documents screen 546. This exemplary Documents screen is displayed when the Documents tab 540 is activated on the Face Sheet tab 521 (FIG. 41). However, the present invention is not limited to such an embodiment and other display screen orders and more fewer and other information fields can be displayed to practice the invention.

A consolidated view of all telemedicine (and actual in-person medicine) patient documents, created uploaded and/or scanned for a patient during a telemedicine (or actual) visit are accessed from the Documents tab 540. Documents display in a selectable table 548 on the left side of the tab with a document preview pane 550 on the right side of the display screen 546. However, the present invention is not limited to such an embodiment and other layout and other embodiments can be used to practice the invention. All patient documents are consolidated on one display page are accessible with minimal selection inputs (e.g., mouse clicks).

The Documents tab 540 allows documents to be easily searched for, displayed and filtered for desired terms. The Documents tab 540 also allows documents to be edited, updated, printed and/or shared.

A method and system for automated medical records processing with telemedicine is presented herein. The method and system includes plural electronic medical templates specifically designed such that they reduce the complexity and risk associated with collecting virtual patient encounter information, creating a medical diagnosis, tracking the patient through the medical processes during a telemedicine session and generate the appropriate number and type medical codes for a specific type of medical practice when processed. The medical codes and other types of processed virtual patient encounter information are displayed in real-time on electronic medical records and invoices immediately after a virtual patient encounter from a telemedicine visit. The present invention is described for use with virtual telemedicine visits. However, the present invention is not limited to telemedicine visits and can also be used with actual patient visits for which a patient actually enters a medical facility.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more fewer or equivalent elements may be used in the block diagrams.

The claims should not be read as limited to the described order or elements unless stated to that effect. In addition, use of the term "means" in any claim is intended to invoke 35 U.S.C. § 112, paragraph 6, and any claim without the word "means" is not so intended.

Therefore, all embodiments that come within the scope and spirit of the following claims and equivalents thereto are claimed as the invention.

I claim:

1. A method for automated processing of medical information with telemedicine, comprising:

creating on a plurality of cloud server network devices each with a telemedicine application and one or more processors on a cloud communications network, a plurality of pooled cloud hardware resources comprising: (1) automatic provisioning of a plurality of pooled cloud hardware resources usable in any amount at any time as needed and available via a plurality of cloud broadband network access components on the plurality of cloud server network devices; (2) automatic scaling of the plurality of pooled cloud hardware resources to obtain and release one or more of the plurality of pooled cloud hardware resources as required; (3) automatic controlling and optimizing the plurality of pooled cloud hardware resources with a metering method; (4) a plurality of cloud software services for automated processing of medical information including a cloud Platform as a Service (PaaS), a cloud computing Infrastructure as a Service (IaaS), and plurality of available cloud Software services as a Service (SaaS) including a plurality of different software services for automated risk reduction in processing of medical records information after virtual patient encounters via a telemedicine visit, the plurality of cloud software services for automated processing of medical information comprising: cloud networking services, storage services, virtualization services, operating system services, run-time services, data services and application services executed with the plurality of pooled cloud hardware resources;

receiving on a first telemedicine application on a first cloud network device with one or more processor a request for a telemedicine visit and virtual patient encounter from a client telemedicine application on a client network device with one or more client network device processors;

applying one or more balancing methods in real-time on the first telemedicine application on the first cloud server network device creating a balancing selection including: (1) balancing telemedicine visit workflow across the plurality of other telemedicine applications on the plurality of other cloud server network devices and across the plurality of pooled cloud hardware resources and the plurality of cloud software services, and (2) balancing telemedicine patient load across a plurality of medical facilities including an availability of plurality of medical personnel at the plurality of medical facilities and a current actual patient load and current telemedicine patient load at the plurality of medical facilities;

selecting from the first telemedicine application on the first cloud server network device with the balancing selection from the one or more balancing methods a selected telemedicine application on a selected cloud server network device to accept the request for the telemedicine visit and the virtual patient encounter;

sending a selection message from the first telemedicine application on the first cloud server network device via the cloud communications network to the selected telemedicine application on the selected cloud server network device indicating the selected telemedicine application on the selected cloud server network device has been selected to accept the telemedicine visit and the virtual patient encounter;

selecting from the selected telemedicine application on the selected cloud server network device a PaaS and an IaaS provided by the plurality of pooled cloud hardware resources on the cloud communications network;

selecting from the selected telemedicine application on the selected cloud server network device via the on the cloud communications network, a first set of SaaS cloud services from the plurality of available cloud SaaS services for automated electronic medical records processing including reducing risk and reducing a number of possible diagnostic decisions when processing medical records from the virtual patient encounter via the telemedicine visit;

selecting from the selected telemedicine application on the selected cloud server network device, one or more SaaS services from the selected first set of SaaS cloud services a plurality of individual data structures comprising a plurality of medical information matrixes including a patient tracking (PT) matrix, historical information (HX) matrix, patient examination (PX) matrix, complexity risk (CX) information matrix and an Evaluation and Management (E/M) summary information matrix, each with a plurality of unique matrix information fields, the plurality of individual data structures stored in one or more cloud storage objects on the cloud communications network and available to the first set of SaaS cloud services selected by the selected telemedicine application on the selected cloud server network device;

collecting data securely on the selected telemedicine application on the selected cloud server network device via the cloud communications network from the client telemedicine application on the client network device for virtual patient encounter during the telemedicine visit, into a plurality of data fields on one or more different electronic medical templates with the one or more SaaS services from the selected first set of SaaS cloud services;

aggregating from the selected telemedicine application on the selected cloud server network device via the cloud communications network with the one or more SaaS services from the selected first set of SaaS cloud services in real-time only selected ones of data items from the plurality of data fields from the one or more different electronic medical templates storing the collected virtual patient encounter data from the telemedicine visit into the plurality of information matrixes stored in the one or more cloud storage objects, the plurality of information matrixes including: the patient tracking (PT) matrix, historical information (HX) matrix, patient examination (PX) matrix, complexity risk (CX) information matrix and the Evaluation and Management (E/M) summary information matrix, each with the plurality of unique matrix information data fields;

eliminating from the selected telemedicine application on the selected cloud server network device via the cloud communications network with the one or more SaaS services from the selected first set of SaaS cloud services with the only selected ones of data items aggregated into the plurality of information matrixes an amount and complexity of the virtual patient encounter data from the telemedicine visit collected to be reviewed during the virtual patient encounter from the telemedicine visit;

reducing from the selected telemedicine application on the selected cloud server network device via the cloud communications network with the one or more SaaS services from the selected first set of SaaS cloud services with the selected data items aggregated into the plurality of information matrixes a number of diagnostic options to be considered during the virtual patient encounter via the telemedicine visit, thereby reducing a medical risk associated with making a complex medical decision for the virtual patient encounter via the telemedicine visit and limiting an amount and complexity of patient data to be processed and reviewed after the virtual patient encounter via the telemedicine visit;

calculating from the selected telemedicine application on the selected cloud server network device via the cloud communications network with the one or more SaaS services from the selected first set of SaaS cloud services in real-time a plurality of matrix summary values from the plurality of information matrixes;

calculating from the selected telemedicine application on the selected cloud server network device via the cloud communications network with the one or more SaaS services from the selected first set of SaaS cloud services in real-time one or more medical and billing codes using the calculated plurality of matrix summary values;

generating automatically from the selected telemedicine application on the selected cloud server network device via the cloud communications network with the one or more SaaS services from the selected first set of SaaS cloud services in real-time an electronic patient medical record with a plurality of data fields from the calculated plurality of matrix summary values and the one or more calculated medical and billing codes;

generating automatically from the selected telemedicine application on the selected cloud server network device via the cloud communications network with the one or more SaaS services from the selected first set of SaaS cloud services in real-time a patient invoice for the virtual patient encounter via the telemedicine visit from the generated electronic medical record; and displaying securely from the selected telemedicine application on the selected cloud server network device via the cloud communications network with the one or more SaaS services from the selected first set of SaaS cloud services in real-time on the selected cloud server network device on a display component via a graphical user interface (GUI) selected ones of the plural data fields from the generated electronic patient medical record, including complexity risk information for the virtual patient encounter via the telemedicine visit and the generated patient invoice, wherein the generated electronic medical record provides a three hundred-sixty degree view of medical, billing, insurance and other information collected and generated from the virtual patient encounter via the telemedicine visit, wherein displaying the three hundred sixty degree view comprises displaying medical, billing, insurance and other information on the GUI surrounding a patient avatar for the virtual patient encounter via the telemedicine visit.

2. A non-transitory computer readable medium in including a plurality of instructions causing one or more processors on one or more network devices to execute the steps of:

creating on a plurality of cloud server network devices each with a telemedicine application and one or more processors on a cloud communications network, a plurality of pooled cloud hardware resources comprising: (1) automatic provisioning of a plurality of pooled cloud hardware resources usable in any amount at any time as needed and available via a plurality of cloud broadband network access components on the plurality of cloud server network devices; (2) automatic scaling of the plurality of pooled cloud hardware resources to obtain and release one or more of the plurality of pooled cloud hardware resources as required; (3) automatic controlling and optimizing the plurality of pooled cloud hardware resources with a metering method; (4) a plurality of cloud software services for automated processing of medical information including a cloud Platform as a Service (PaaS), a cloud computing Infrastructure as a Service (IaaS), and plurality of available cloud Software services as a Service (SaaS) including a plurality of different software services for automated risk reduction in processing of medical records information after virtual patient encounters via a telemedicine visit, the plurality of cloud software services for automated processing of medical information comprising: cloud networking services, storage services, virtualization services, operating system services, run-time services, data services and application services executed with the plurality of pooled cloud hardware resources;

receiving on a first telemedicine application on a first cloud network device with one or more processor a request for a telemedicine visit and virtual patient encounter from a client telemedicine application on a client network device with one or more client network device processors;

applying one or more balancing methods in real-time on the first telemedicine application on the first cloud server network device creating a balancing selection including: (1) balancing telemedicine visit workflow across the plurality of other telemedicine applications on the plurality of other cloud server network devices and across the plurality of pooled cloud hardware resources and the plurality of cloud software services, and (2) balancing telemedicine patient load across a plurality of medical facilities including an availability of plurality of medical personnel at the plurality of medical facilities and a current actual patient load and current telemedicine patient load at the plurality of medical facilities;

selecting from the first telemedicine application on the first cloud server network device with the balancing selection from the one or more balancing methods a selected telemedicine application on a selected cloud server network device to accept the request for the telemedicine visit and the virtual patient encounter;

sending a selection message from the first telemedicine application on the first cloud server network device via the cloud communications network to the selected telemedicine application on the selected cloud server network device indicating the selected telemedicine application on the selected cloud server network device has been selected to accept the telemedicine visit and the virtual patient encounter;

selecting from the selected telemedicine application on the selected cloud server network device a PaaS and an IaaS provided by the plurality of pooled cloud hardware resources on the cloud communications network;

selecting from the selected telemedicine application on the selected cloud server network device via the on the cloud communications network, a first set of SaaS cloud services from the plurality of available cloud SaaS services for automated electronic medical records processing including reducing risk and reducing a number of possible diagnostic decisions when processing medical records from the virtual patient encounter via the telemedicine visit;

selecting from the selected telemedicine application on the selected cloud server network device, one or more SaaS services from the selected first set of SaaS cloud services a plurality of individual data structures comprising a plurality of medical information matrixes including a patient tracking (PT) matrix, historical information (HX) matrix, patient examination (PX) matrix, complexity risk (CX) information matrix and an Evaluation and Management (E/M) summary information matrix, each with a plurality of unique matrix information fields, the plurality of individual data structures stored in one or more cloud storage objects on the cloud communications network and available to the first set of SaaS cloud services selected by the selected telemedicine application on the selected cloud server network device;

collecting data securely on the selected telemedicine application on the selected cloud server network device via the cloud communications network from the client telemedicine application on the client network device for virtual patient encounter during the telemedicine visit, into a plurality of data fields on one or more different electronic medical templates with the one or more SaaS services from the selected first set of SaaS cloud services;

aggregating from the selected telemedicine application on the selected cloud server network device via the cloud communications network with the one or more SaaS services from the selected first set of SaaS cloud services in real-time only selected ones of data items from the plurality of data fields from the one or more different electronic medical templates storing the collected virtual patient encounter data from the telemedicine visit into the plurality of information matrixes stored in the one or more cloud storage objects, the plurality of information matrixes including: the patient tracking (PT) matrix, historical information (HX) matrix, patient examination (PX) matrix, complexity risk (CX) information matrix and the Evaluation and Management (E/M) summary information matrix, each with the plurality of unique matrix information data fields;

eliminating from the selected telemedicine application on the selected cloud server network device via the cloud communications network with the one or more SaaS services from the selected first set of SaaS cloud services with the only selected ones of data items aggregated into the plurality of information matrixes an amount and complexity of the virtual patient encounter data from the telemedicine visit collected to be reviewed during the virtual patient encounter from the telemedicine visit;

reducing from the selected telemedicine application on the selected cloud server network device via the cloud communications network with the one or more SaaS services from the selected first set of SaaS cloud services with the selected data items aggregated into the plurality of information matrixes a number of diagnostic options to be considered during the virtual patient encounter via the telemedicine visit, thereby reducing a medical risk associated with making a complex medical decision for the virtual patient encounter via the telemedicine visit and limiting an amount and complexity of patient data to be processed and reviewed after the virtual patient encounter via the telemedicine visit;

calculating from the selected telemedicine application on the selected cloud server network device via the cloud communications network with the one or more SaaS services from the selected first set of SaaS cloud services in real-time a plurality of matrix summary values from the plurality of information matrixes;

calculating from the selected telemedicine application on the selected cloud server network device via the cloud communications network with the one or more SaaS services from the selected first set of SaaS cloud services in real-time one or more medical and billing codes using the calculated plurality of matrix summary values;

generating automatically from the selected telemedicine application on the selected cloud server network device via the cloud communications network with the one or more SaaS services from the selected first set of SaaS cloud services in real-time an electronic patient medical record with a plurality of data fields from the calculated plurality of matrix summary values and the one or more calculated medical and billing codes;

generating automatically from the selected telemedicine application on the selected cloud server network device via the cloud communications network with the one or more SaaS services from the selected first set of SaaS cloud services in real-time a patient invoice for the virtual patient encounter via the telemedicine visit from the generated electronic medical record; and displaying securely from the selected telemedicine application on the selected cloud server network device via the cloud communications network with the one or more SaaS services from the selected first set of SaaS cloud services in real-time on the selected cloud server network device on a display component via a graphical user interface (GUI) selected ones of the plural data fields from the generated electronic patient medical record, including complexity risk information for the virtual patient encounter via the telemedicine visit and the generated patient invoice, wherein the generated electronic medical record provides a three hundred-sixty degree view of medical, billing, insurance and other information collected and generated from the virtual patient encounter via the telemedicine visit, wherein displaying the three hundred sixty degree view comprises displaying medical, billing, insurance and other information on the GUI surrounding a patient avatar for the virtual patient encounter via the telemedicine visit.

3. The method of claim 1 wherein the Patient Tracking (PT) matrix includes a Tracking Board component, a Patient Demographics component and a Face Sheet component, each with a plurality of fields.

4. The method of claim 3 wherein the Tracking Board component includes a plurality of fields comprising: a Queue name, Time In, Wait Timer, Name, Chart, Type, Patient Arrival Status, Schedule Type, Status, Age and a Web or Kiosk Check-In Time field.

5. The method of claim 4 wherein the Queue name includes front desk, waiting room, lab, radiology, labs pending results, lab pending review, provider, clinical, sign out, follow up call, missed appointments, or non-provider sign off.

6. The method of claim 3 wherein the Patient Demographics component includes a plurality of fields comprising: a Patent Name field, Visit History field, Previous Vitals field, Patient Lists field, Vaccines field, Lab History field and a Patients Notes field.

7. The method of claim 6 wherein the Patients Notes field includes a plurality of sub-fields comprising Date of Service, Clinic, Visit Type, Chart, Note Type, Note, Queues, Assigned to Queues and Created on sub-fields.

8. The method of claim 1 wherein the Face Sheet component includes a plurality of fields comprising a History, Vitals, HPI, Plan, Prescriptions, Images, Labs, Procedures and Supplies, Referrals, Documents and Visits, fields.

9. The method of claim 1 wherein the virtual patient encounter for the telemedicine visits includes a patient encounter conducted between medical personal and a patient over a communications network, wherein the patent does not physically enter a medical facility.

10. The method of claim 3 further comprising:
extracting information from one or more selected fields of the Tracking Board component of the Patient Tracking (PT) matrix via the selected telemedicine application on the selected cloud server network device with the one or more SaaS services from the selected first set of SaaS cloud services in real-time;
extracting information from one or more selected fields of the Patient Demographics component and the Face Sheet component of the Patient Tracking (PT) matrix via the selected telemedicine application on the selected cloud server network device with the one or more SaaS services from the selected first set of SaaS cloud services in real-time;
calculating one or more patient tracking risk values for the actual or virtual patient encounter from the information extracted from the Tracking Board component, the Patient Demographics component and the Face Sheet component of the Patient Tracking (PT) matrix the with the selected telemedicine application on the selected cloud server network device with the one or more SaaS services from the selected first set of SaaS cloud services in real-time; and
integrating the calculated one or more patient tracking risk values with other risk values calculated with the complexity risk (CX) information matrix and the Evaluation and Management (E/M) summary information matrix, thereby further reducing risk and complexity associated with the actual or virtual patient encounter with the Patient Tracking (PT) matrix with the selected telemedicine application on the selected cloud server network device with the one or more SaaS services from the selected first set of SaaS cloud services in real-time.

11. The method of claim 10 wherein the extracting information from one or more selected fields of the Tracking Board component of the Patient Tracking (PT) matrix step includes extracting information from Queue Name, Time In, Wait Timer, Name and Chart fields, in the Tracking Board component.

12. The method of claim 10 wherein the extracting information from one or more selected fields of the Patient Demographics component of the Patient Tracking (PT) matrix includes extracting information from the Patent Name field, Visit History field, Previous Vitals field, Vaccines field, Lab History field and a Patients Notes fields, in the Patient Demographics component.

13. The method of claim 10 wherein the extracting information from one or more selected fields of the Face Sheet component of the Patient Tracking (PT) matrix includes extracting information from the History, Vitals, HPI, Plan, Prescriptions, Images, Labs, Procedures and Supplies, Referrals, Documents and Visits fields, in the Face Sheet component for a telemedicine patient encounter.

14. The method of claim 1 further comprising:
providing a secure telemedicine application to a selected client network device with one or more selected client network device processors from a second telemedicine application on a second cloud server network device with one or more processors via the cloud communications network;
receiving securely telemedicine visit information on the second telemedicine application on the second cloud server network device via the cloud communications network from the secure telemedicine application on the selected client network device for a patient,
receiving telemedicine appointment and registration information and preliminary telemedicine patient encounter information via the selected client network device on the second telemedicine application on the second cloud server network device and making the patient appointment and registration and preliminary patient encounter information available to the selected telemedicine application on the selected telemedicine network device before a virtual telemedicine patient encounter occurs and making available the patient appointment and registration information and preliminary patient encounter information obtained on the selected client network device in the patient tracking (PT) matrix; and
sending one or more types of automated messages from the second telemedicine application on the second cloud server network device to the secure telemedicine application on the selected client network device confirming successful receiving of patient appointment and registration and preliminary patient encounter information from the selected telemedicine application on the selected cloud server network device.

15. The method of claim 1 wherein the one or more medical codes and billing codes include one or more of Evaluation and Management codes ("E/Ms") codes, Current Procedural Terminology ("CPTs") codes, Health Care Financing Administration Common Procedural Coding System ("HCPCS") codes International Classification of Diseases $9^{th}$ Edition Clinical Modification ("ICD-9") codes, International Classification of Diseases 10th Edition Clinical Modification ("ICD-10") or SNOMED Clinical Terms ("SNOWMED CT") codes.

16. The method of claim 1 wherein the client network device includes a personal digital/data assistant (PDA), an electronic tablet, Internet appliance, mobile phone, smart phone, wearable network device, electronic gaming platform, Internet of Things (IoT) network device, three-dimensional (3D) display network device, desktop computer or laptop computer.

17. The method of claim 1 wherein the client network device includes a wireless interface for communicating with the cloud communications network, the wireless interface comprising: an IEEE 802.11a, 802.11b, 802.11g, 802.11n, 802.15.4 (ZigBee), 802.16a, 802.16g, Wireless Fidelity (Wi-Fi), Worldwide Interoperability for Microwave Access (WiMAX), ETSI High Performance Radio Metropolitan Area Network (HIPERMAN), Z-wave, Bluetooth, Infrared, Industrial, Scientific and Medical (ISM), Radio Frequency Identifier (RFID), Near field communication (NFC), Machine-2-Machine (M2M), cellular telephone or cellular telephone data wireless interface.

18. The method of claim 1 wherein the one or more different electronic medical templates include one or more of: a medical practice template, referral template, electronic invoice template, electronic medical record template, current compliant template, diagnosis template, nurse template, review template, patient tracking template, or an insurance provider template, wherein the medical practice template includes an electronic medical template for pediatrics, obstetrics and gynecology, cardiology, neurology, family practice medicine, emergency room medicine, walk-in clinics, urgent care clinics or telemedicine clinics.

19. The method of claim 18 wherein the medical practice template includes a plurality of features and data fields comprising: Menopause documentation, Pregnancy Electronic Due Date Calculator (EDC), Clinical decision support, Clinical decision alerts and action plans, Pharyngitis alerts, History not completed, New condition workup planned, Provider-to-Provider notes section, Preformatted discharge notes, Visit summary notes, Third party primary historian notes, Electronic signature collection, Document multiple health protocols, Integration with laboratory services, Virtual phone encounter motes, X-ray interface, Date of birth birthday notification, Medicare and Medicaid reports, Clinical Quality Measures (CQM) and National Framework of Qualifications (NQF) reports, Graphical plots of vital charts, Medication Reconciliation, Public Health Surveillance interface, Referral Management, Matrix calculation and coding results reports and queries and multi-colored patient, insurance and billing alerts.

20. A system for automated processing of medical information, comprising in combination:
   a cloud communications network;
   one or more network devices configured for causing one or more processors on the one or more networking devices to execute a plurality of instructions:
   for creating on a plurality of cloud server network devices each with a telemedicine application and one or more processors on a cloud communications network, a plurality of pooled cloud hardware resources comprising: (1) automatic provisioning of a plurality of pooled cloud hardware resources usable in any amount at any time as needed and available via a plurality of cloud broadband network access components on the plurality of cloud server network devices; (2) automatic scaling of the plurality of pooled cloud hardware resources to obtain and release one or more of the plurality of pooled cloud hardware resources as required; (3) automatic controlling and optimizing the plurality of pooled cloud hardware resources with a metering method; (4) a plurality of cloud software services for automated processing of medical information including a cloud Platform as a Service (PaaS), a cloud computing Infrastructure as a Service (IaaS), and plurality of available cloud Software services as a Service (SaaS) including a plurality of different software services for automated risk reduction in processing of medical records information after virtual patient encounters via a telemedicine visit, the plurality of cloud software services for automated processing of medical information comprising: cloud networking services, storage services, virtualization services, operating system services, run-time services, data services and application services executed with the plurality of pooled cloud hardware resources;

for receiving on a first telemedicine application on a first cloud network device with one or more processor a request for a telemedicine visit and virtual patient encounter from a client telemedicine application on a client network device with one or more client network device processors;

for applying one or more balancing methods in real-time on the first telemedicine application on the first cloud server network device creating a balancing selection including: (1) balancing telemedicine visit workflow across the plurality of other telemedicine applications on the plurality of other cloud server network devices and across the plurality of pooled cloud hardware resources and the plurality of cloud software services, and (2) balancing telemedicine patient load across a plurality of medical facilities including an availability of plurality of medical personnel at the plurality of medical facilities and a current actual patient load and current telemedicine patient load at the plurality of medical facilities;

for selecting from the first telemedicine application on the first cloud server network device with the balancing selection from the one or more balancing methods a selected telemedicine application on a selected cloud server network device to accept the request for the telemedicine visit and the virtual patient encounter;

for sending a selection message from the first telemedicine application on the first cloud server network device via the cloud communications network to the selected telemedicine application on the selected cloud server network device indicating the selected telemedicine application on the selected cloud server network device has been selected to accept the telemedicine visit and the virtual patient encounter;

for selecting from the selected telemedicine application on the selected cloud server network device a PaaS and an IaaS provided by the plurality of pooled cloud hardware resources on the cloud communications network;

for selecting from the selected telemedicine application on the selected cloud server network device via the on the cloud communications network, a first set of SaaS cloud services from the plurality of available cloud SaaS services for automated electronic medical records processing including reducing risk and reducing a number of possible diagnostic, decisions when processing medical records from the virtual patient encounter via the telemedicine visit;

for selecting from the selected telemedicine application on the selected cloud server network device, one or more SaaS services from the selected first set of SaaS cloud services a plurality of individual data structures comprising a plurality of medical information matrixes including a patient tracking (PT) matrix, historical information (HX) matrix, patient examination (PX) matrix, complexity risk (CX) information matrix and an Evaluation and Management (E/M) summary information matrix, each with a plurality of unique matrix information fields, the plurality of individual data structures stored in one or more cloud storage objects on the cloud communications network and available to the first set of SaaS cloud services selected by the selected telemedicine application on the selected cloud server network device;

for collecting data securely on the selected telemedicine application on the selected cloud server network device via the cloud communications network from the client telemedicine application on the client network device for virtual patient encounter during the telemedicine visit, into a plurality of data fields on one or more different electronic medical templates with the one or more SaaS services from the selected first set of SaaS cloud services;

for aggregating from the selected telemedicine application on the selected cloud server network device via the cloud communications network with the one or more SaaS services from the selected first set of SaaS cloud services in real-time only selected ones of data items from the plurality of data fields from the one or more different electronic medical templates storing the collected virtual patient encounter data from the telemedicine visit into the plurality of information matrixes stored in the one or more cloud storage objects, the plurality of information matrixes including: the patient tracking (PT) matrix, historical information (HX) matrix, patient examination (PX) matrix, complexity risk (CX) information matrix and the Evaluation and Management (E/M) summary information matrix, each with the plurality of unique matrix information data fields;

for eliminating from the selected telemedicine application on the selected cloud server network device via the cloud communications network with the one or more SaaS services from the selected first set of SaaS cloud services with the only selected ones of data items aggregated into the plurality of information matrixes an amount and complexity of the virtual patient encounter data from the telemedicine visit collected to be reviewed during the virtual patient encounter from the telemedicine visit;

for reducing from the selected telemedicine application on the selected cloud server network device via the cloud communications network with the one or more SaaS services from the selected first set of SaaS cloud services with the selected data items aggregated into the plurality of information matrixes a number of diagnostic options to be considered during the virtual patient encounter via the telemedicine visit, thereby reducing a medical risk associated with making a complex medical decision for the virtual patient encounter via the telemedicine visit and limiting an amount and complexity of patient data to be processed and reviewed after the virtual patient encounter via the telemedicine visit;

for calculating from the selected telemedicine application on the selected cloud server network device via the cloud communications network with the one or more SaaS services from the selected first set of SaaS cloud services in real-time a plurality of matrix summary values from the plurality of information matrixes;

for calculating from the selected telemedicine application on the selected cloud server network device via the cloud communications network with the one or more SaaS services from the selected first set of SaaS cloud services in real-time one or more medical and billing codes using the calculated plurality of matrix summary values;

for generating automatically from the selected telemedicine application on the selected cloud server network device via the cloud communications network with the one or more SaaS services from the selected first set of SaaS cloud services in real-time an electronic patient medical record with a plurality of data fields from the calculated plurality of matrix summary values and the one or more calculated medical and billing codes;

for generating automatically from the selected telemedicine application on the selected cloud server network device via the cloud communications network with the one or more SaaS services from the selected first set of SaaS cloud services in real-time a patient invoice for the virtual patient encounter via the telemedicine visit from the generated electronic medical record; and for displaying securely from the selected telemedicine application on the selected cloud server network device via the cloud communications network with the one or more SaaS services from the selected first set of SaaS cloud services in real-time on the selected cloud server network device on a display component via a graphical user interface (GUI) selected ones of the plural data fields from the generated electronic patient medical record, including complexity risk information for the virtual patient encounter via the telemedicine visit and the generated patient invoice, wherein the generated electronic medical record provides a three hundred-sixty degree view of medical, billing, insurance and other information collected and generated from the virtual patient encounter via the telemedicine visit, wherein displaying the three hundred sixty degree view comprises displaying medical, billing, insurance and other information on the GUI surrounding a patient avatar for the virtual patient encounter via the telemedicine visit.

* * * * *